United States Patent
Blanchette et al.

(10) Patent No.: US 12,226,529 B2
(45) Date of Patent: Feb. 18, 2025

(54) STABLE NANOLIPOPROTEIN PARTICLES AND RELATED COMPOSITIONS METHODS AND SYSTEMS

(71) Applicants: LAWRENCE LIVERMORE NATIONAL SECURITY, LLC, Livermore, CA (US); THE REGENTS OF THE UNIVERSITY OF CALIFORNIA, Oakland, CA (US)

(72) Inventors: Craig D. Blanchette, Concord, CA (US); Nicholas Fischer, Livermore, CA (US); Sean Fitzpatrick Gilmore, Oakland, CA (US); Amy Rasley, Livermore, CA (US); Paul Henderson, Dublin, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 0 days.

(21) Appl. No.: 15/755,018

(22) PCT Filed: Aug. 25, 2016

(86) PCT No.: PCT/US2016/048632
§ 371 (c)(1),
(2) Date: Feb. 23, 2018

(87) PCT Pub. No.: WO2017/035326
PCT Pub. Date: Mar. 2, 2017

(65) Prior Publication Data
US 2019/0142752 A1    May 16, 2019

Related U.S. Application Data

(60) Provisional application No. 62/209,784, filed on Aug. 25, 2015.

(51) Int. Cl.
*A61K 9/127* (2006.01)
*A61K 47/69* (2017.01)
*A61K 49/00* (2006.01)
*C07F 9/10* (2006.01)
*C07K 14/705* (2006.01)
*C07K 14/775* (2006.01)
*B82Y 5/00* (2011.01)

(52) U.S. Cl.
CPC .......... *A61K 9/1273* (2013.01); *A61K 9/1278* (2013.01); *A61K 47/6915* (2017.08); *A61K 49/0086* (2013.01); *C07F 9/106* (2013.01); *C07K 14/705* (2013.01); *C07K 14/775* (2013.01); *B82Y 5/00* (2013.01)

(58) Field of Classification Search
CPC .............. A61K 9/1273; A61K 47/6915; A61K 49/0086; C07K 14/775
See application file for complete search history.

(56) References Cited

U.S. PATENT DOCUMENTS

| | | |
|---|---|---|
| 4,317,771 A | 3/1982 | Shiba et al. |
| 5,374,715 A | 12/1994 | Kanno et al. |
| 5,393,530 A | 2/1995 | Schneider |
| 5,679,559 A | 10/1997 | Kim et al. |
| 6,270,649 B1 | 8/2001 | Zeikus et al. |
| 6,365,191 B1 | 4/2002 | Burman et al. |
| 6,599,527 B1 | 7/2003 | Leigh et al. |
| 7,015,471 B2 | 3/2006 | Franzen et al. |
| 7,048,949 B2 | 5/2006 | Sligar et al. |
| 7,083,958 B2 | 8/2006 | Sligar et al. |
| 7,375,234 B2 | 5/2008 | Sharpless et al. |
| 7,575,763 B2 | 8/2009 | Sligar et al. |
| 7,592,008 B2 | 9/2009 | Sligar et al. |
| 7,622,437 B2 | 11/2009 | Morrissey et al. |
| 7,662,410 B2 | 2/2010 | Sligar et al. |
| 7,691,414 B2 | 4/2010 | Sligar et al. |
| 7,824,709 B2 | 11/2010 | Ryan et al. |
| 8,183,010 B2 | 5/2012 | Swartz et al. |
| 8,268,796 B2 | 9/2012 | Ryan |
| 8,883,729 B2 | 11/2014 | Hoeprich et al. |
| 8,889,623 B2 | 11/2014 | Hoeprich et al. |
| 8,895,055 B2 | 11/2014 | Lam et al. |
| 8,907,061 B2 | 12/2014 | Chromy et al. |
| 9,303,273 B2 | 4/2016 | Hoeprich et al. |
| 9,388,232 B2 | 7/2016 | Dasseux et al. |
| 9,458,191 B2 | 10/2016 | Chromy et al. |
| 9,644,038 B2 | 5/2017 | Luo et al. |
| 9,688,718 B2 | 6/2017 | Baker et al. |

(Continued)

FOREIGN PATENT DOCUMENTS

| | | |
|---|---|---|
| EP | 3426304 A1 | 1/2019 |
| JP | 2008516605 A | 5/2008 |

(Continued)

OTHER PUBLICATIONS https://www.ebi.ac.uk/training-beta/online/courses/metabolomics-introduction/what-is/small-molecules/, printed from web Aug. 4, 2020 (Year: 2020).*
Baughman, R.H. "Solid-state polymerization of diacetylenes." *Journal of Applied Physics* 43(11), 4362-4370,(Nov. 1972). 10 pages.
Blanchette, C.D., et al. "Kinetic Analysis of His-Tagged Protein Binding to Nickel-Chelating Nanolipoprotein Particles." *Bioconjugate Chemistry* 21(7), 1321-1330, (Jun. 2010). 10 pages.
Fischer, N.O., et al. "Colocalized Delivery of Adjuvant and Antigen Using Nanolipoprotein Particles Enhances the Immune Response to Recombinant Antigens." *Journal of the American Chemical Society* 135(6), 2044-2047, (Jan. 2013). 4 pages.
Frias, J.C., et al. "Properties of a Versatile Nanoparticle Platform Contrast Agent To Image and Characterize Atherosclerotic Plaques by Magnetic Resonance Imaging." *Nano Letters* 6(10), 2220-2224, (Jul. 2006). 5 pages.

(Continued)

*Primary Examiner* — James W Rogers
(74) *Attorney, Agent, or Firm* — Steinfl + Bruno LLP

(57) ABSTRACT

Nanolipoprotein particles having at least a scaffold protein component and a membrane lipid component and related compositions, methods and systems are described. The membrane lipid component includes at least one or more membrane forming lipids, one or more polymerized lipids and/or one or more polymerizable lipids.

36 Claims, 9 Drawing Sheets

(56) References Cited

U.S. PATENT DOCUMENTS

| | | |
|---|---|---|
| 10,151,037 B2 | 12/2018 | Hoeprich, Jr. et al. |
| 10,934,628 B2 | 3/2021 | Hoeprich, Jr. et al. |
| 11,053,322 B2 | 7/2021 | Luo et al. |
| 11,207,422 B2 | 12/2021 | Coleman et al. |
| 11,279,749 B2 | 3/2022 | Hoeprich, Jr. et al. |
| 11,300,572 B2 | 4/2022 | Coleman et al. |
| 2001/0051131 A1* | 12/2001 | Unger .................. A61K 49/223 424/9.5 |
| 2002/0041898 A1 | 4/2002 | Unger et al. |
| 2003/0008014 A1* | 1/2003 | Shelness .............. A61K 9/1275 424/499 |
| 2004/0101741 A1 | 5/2004 | Minteer et al. |
| 2004/0180369 A1 | 9/2004 | Franzen et al. |
| 2004/0204354 A1 | 10/2004 | Nelson et al. |
| 2005/0182243 A1 | 8/2005 | Sligar et al. |
| 2005/0244414 A1 | 11/2005 | Mundy et al. |
| 2006/0013885 A1 | 1/2006 | Nah et al. |
| 2006/0088524 A1* | 4/2006 | Morrissey ............ A61K 9/5169 424/133.1 |
| 2006/0127310 A1 | 6/2006 | Russell-Jones et al. |
| 2006/0127467 A1 | 6/2006 | Watkin |
| 2006/0189554 A1 | 8/2006 | Mumper et al. |
| 2006/0211092 A1 | 9/2006 | Sligar et al. |
| 2007/0101448 A1 | 5/2007 | Anantharamiah et al. |
| 2007/0117179 A1 | 5/2007 | Kudlicki et al. |
| 2007/0287034 A1 | 12/2007 | Minteer et al. |
| 2008/0124350 A1 | 5/2008 | Mumper et al. |
| 2008/0188399 A1 | 8/2008 | Sinko et al. |
| 2008/0248565 A1 | 10/2008 | Katzen et al. |
| 2009/0136937 A1 | 5/2009 | Coleman et al. |
| 2009/0186393 A1 | 7/2009 | Baker et al. |
| 2009/0192299 A1 | 7/2009 | Chromy et al. |
| 2009/0203549 A1 | 8/2009 | Hoeprich, Jr. et al. |
| 2009/0203706 A1 | 8/2009 | Zhao et al. |
| 2009/0270331 A1 | 10/2009 | Remaley et al. |
| 2009/0311276 A1 | 12/2009 | Hoeprich et al. |
| 2009/0324706 A1 | 12/2009 | Mirkin et al. |
| 2010/0092567 A1 | 4/2010 | Hoeprich et al. |
| 2010/0158994 A1 | 6/2010 | Watkin |
| 2010/0203609 A1 | 8/2010 | Yacoby et al. |
| 2011/0059549 A1 | 3/2011 | Coleman et al. |
| 2011/0178029 A1 | 7/2011 | Knudsen et al. |
| 2011/0178164 A1 | 7/2011 | Cunha et al. |
| 2011/0195450 A1 | 8/2011 | Kudlicki et al. |
| 2011/0286915 A1 | 11/2011 | Lam et al. |
| 2012/0148642 A1 | 6/2012 | Remaley et al. |
| 2012/0245101 A1 | 9/2012 | Anantharamaiah et al. |
| 2013/0164369 A1 | 6/2013 | Lam et al. |
| 2013/0165636 A1 | 6/2013 | Luo et al. |
| 2014/0273142 A1 | 9/2014 | Hoeprich |
| 2014/0308341 A1 | 10/2014 | Fujii et al. |
| 2015/0140108 A1 | 5/2015 | Peer et al. |
| 2016/0083858 A1* | 3/2016 | Hoeprich, Jr. ............ C25B 1/02 205/351 |
| 2016/0235671 A1 | 8/2016 | Li et al. |
| 2016/0324923 A1 | 11/2016 | Dasseux et al. |
| 2018/0079829 A1 | 3/2018 | Luo et al. |
| 2018/0186860 A1 | 7/2018 | Hoeprich, Jr. et al. |
| 2018/0318218 A1 | 11/2018 | Kamrud et al. |
| 2019/0055658 A1 | 2/2019 | Hoeprich, Jr. et al. |
| 2019/0094230 A1 | 3/2019 | Coleman et al. |
| 2019/0307692 A1 | 10/2019 | Blanchette et al. |
| 2020/0046848 A1 | 2/2020 | Coleman et al. |
| 2021/0317234 A1 | 10/2021 | Luo |
| 2022/0283171 A1 | 9/2022 | Coleman et al. |

FOREIGN PATENT DOCUMENTS

| | | | |
|---|---|---|---|
| JP | 2015110677 A | 6/2015 | |
| WO | 99/59550 A1 | 11/1999 | |
| WO | 00/65099 A1 | 11/2000 | |
| WO | 02/40501 A2 | 5/2002 | |
| WO | 2004/094651 A2 | 11/2004 | |
| WO | 2004/112214 A2 | 12/2004 | |
| WO | 2005/070400 A1 | 8/2005 | |
| WO | 2006/073419 A2 | 7/2006 | |
| WO | 2007/038755 A1 | 4/2007 | |
| WO | 2007/050501 A2 | 5/2007 | |
| WO | 2007/053655 A2 | 5/2007 | |
| WO | 2008/028206 A2 | 3/2008 | |
| WO | 2008/106660 A2 | 9/2008 | |
| WO | 2009/100201 A2 | 8/2009 | |
| WO | 2010/039496 A2 | 4/2010 | |
| WO | 2010/040897 A1 | 4/2010 | |
| WO | WO-2014063097 A1 * | 4/2014 | .......... C07K 14/315 |
| WO | 2017/035326 A1 | 3/2017 | |
| WO | 2017/044899 A1 | 3/2017 | |
| WO | 2017/155837 A1 | 9/2017 | |
| WO | 2018/204421 A2 | 11/2018 | |

OTHER PUBLICATIONS

Georger, J.H., et al. "Helical and Tubular Microstructures Formed by Polymerizable Phosphatidylcholines." *Journal of American Chemical Society* 109(20), 6169-6175, (Sep. 1987). 7 pages.

Hayward, J.A., et al. "Biomembrane surfaces as models for polymer design: the potential for haemocompatibility." *Biomaterials* 5(3), 135-142, (May 1984). 8 pages.

Jia, J., et al. "Preparation, Characterizations, and In Vitro Metabolic Processes of Paclitaxel-Loaded Discoidal Recombinant High-Density Lipoproteins." *Journal of Pharmaceutical Sciences* 101(8), 2900-2908, (Aug. 2012). 9 pages.

Johnston, D.S., et al. "Phospholipid Polymers—Synthesis and Spectral Characteristics." *Biochimica et Biophysica Acta* 602(1), 57-69, (Oct. 1980). 13 pages.

Jonsson, M.P., et al. "Supported Lipid Bilayer Formation and Lipid-Membrane-Mediated Biorecognition Reactions Studied with a New Nanoplasmonic Sensor Template." *Nano Letters* 7(11), 3462-3468, (Sep. 2007). 7 pages.

Kim, J-M., et al. "Immobilized Polydiacetylene Vesicles on Solid Substrates for Use as Chemosensors." *Advanced Materials* 15(13), 1118-1121, (Jul. 2003). 4 pages.

Lamparski, H., et al. "Two-Dimensional Polymerization of Lipid Bilayers: Degree of Polymerization of Sorbyl Lipids." *Macromolecules* 28(6), 1786-1794, (Mar. 1995). 9 pages.

Lei, J., et al. "Two-Dimensional Polymerization of Lipid Bilayers: Rate of Polymerization of Acryloyl and Methacryloyl Lipids." *Macromolecules* 27(6), 1381-1388, (Mar. 1994). 8 pages.

Lieser, G., et al. "Structure, Phase Transitions and Polymerizability of Multilayers of some Diacetylene Monocarboxylic Acids." *Thin Solid Films* 68(1), 77-90, (May 1980). 14 pages.

Morigaki, K., et al. "Surface Functionalization of a Polymeric Lipid Bilayer for Coupling a Model Biological Membrane with Molecules, Cells, and Microstructures." *Langmuir* 29(8), 2722-2730, (Jan. 2013). 9 pages.

Ohno, H., et al. "Polymerization of Liposomes Composed of Diene-Containing Lipids by UV and Radical Initiators: Evidence for the Different Chemical Environment of Diene Groups on 1- and 2-Acyl Chains." *Macromolecules* 20(5), 929-933, (May 1987). 5 pages.

Okazaki, T., et al. "Phase Separation of Lipid Microdomains Controlled by Polymerized Lipid Bilayer Matrices." *Langmuir* 26(6), 4126-4129, (Dec. 2009). 4 pages.

Rabinovich, A.L., et al. "On the conformational, physical properties and functions of polyunsaturated acyl chains." *Biochimica et Biophysica Acta* 1085(1), 53-62, (Aug. 1991). 10 pages.

Regen, S.L., et al. "Polymerized Phophatidyl Choline Vesicles. Stabilized and Controllable Time-Release Carriers." *Biochemical and Biophysical Research Communications* 101(1), 131-136, (Jul. 1981). 6 pages.

Sadownik, A., et al. "Polymerized Liposomes Formed under Extremely Mild Conditions." *Journal of American Chemical Society* 108(24), 7789-7791, (Nov. 1986). 3 pages.

Sells, T.D., et al. "Two-Dimensional Polymerization of Lipid Bilayers: Degree of Polymerization of Acryloyl Lipids." *Macromolecules* 27(1), 226-233, (Jan. 1994). 8 pages.

(56) References Cited

OTHER PUBLICATIONS

Serrano, J., et al. "Polymerized Surfactant Vesicles. Determinations of Rates and Degrees of Polymerization in Vesicles Prepared from Styrene-Containing Surfactants." *Macromolecules* 18(10), 1999-2005, (Oct. 1985). 7 pages.

Shih, A.Y., et al. "Disassembly of Nanodiscs with Cholate." *Nano Letters* 7(6), 1692-1696, (May 2007). 5 pages.

Tsuchida, E., et al. "Polymerization of Unsaturated Phospholipids as Large Unilamellar Liposomes at Low Temperature." *Macromolecules* 25(1) 207-212, (Jan. 1992). 6 pages.

Aina O.H., et al., "From combinatorial chemistry to cancer-targeting peptides" Mol Pharm, vol. 4, No. 5, pp. 631-651 (2007).

Badamchi-Zadeh A, et al., "A multi-component prime-boost vaccination regimen with a consensus MOMP antigen enhances chlamydia trachomatis clearance." Frontiers In Immunology, vol. 7, Article 162, pp. 1-11 (Apr. 2016).

Baehr W, et al., "Mapping antigenic domains expressed by Chlamydia trachomatis major outer membrane protein genes." Proceeding of the National Academy of Sciences, vol. 85, pp. 4000-4004 (1988).

Carmichael J.R. et al., "Induction of protection against vaginal shedding and infertility by recombinant Chlamydia vaccine" *Vaccine*, 29, pp. 5276-5283(2011).

Chen et al., "Fluorescence Study of Inclusion Complexes between Star-Shaped Cholic Acid Derivatives and Polycyclic Aromatic Fluorescent Probes and the Size Effects of Host and Guest Molecules" Journal of Physical Chemistry B, vol. 112, No. 11, p. 3402-3409 (2008).

Coleman M.A, et al., "Expression and Association of the Yersinia pestis Translocon Proteins, YopB and YopD, Are Facilitated by Nanolipoprotein Particles." *PLoS One* p.e0150166 (2016). 16 pages.

Conlan J, et al., "Isolation of recombinant fragments of the major outer-membrane protein of Chlamydia trachomatis: their potential as subunit vaccines" Microbiology, 136, pp. 2013-2020 (1992).

Corrected Notice of Allowance for U.S. Appl. No. 13/719,785, filed Dec. 19, 2012 on behalf of Lawrence Livermore National Laboratory Mail Date: May 23, 2016 5 pages.

Dalkara et al., "Intracytoplasmic Delivery of Anionic Proteins" Molecular Therapy, Jun. 2004, vol. 9, No. 6, pp. 964-969.

Davidson E, et al., "A high-throughput shotgun mutagenesis approach to mapping B-cell antibody epitopes" Immunology, 143, pp. 13-20 (2014).

Duncan R., "Dawning Era of Polymer Therapeutics" Nature Review Drug Discovery vol. 2, No. 5 p. 347-360 (2003).

Farris C.M. et al., "CD4+ T cells and antibody are required for optimal major outer membrane protein vaccine-induced immunity to Chlamydia muridarum genital infection" Infection and Immunity, vol. 78, No. 10, pp. 4374-4383 (2010).

Feher V.A. et al., "A 3-dimensional trimeric B-barrel model for Chlamydia MOMP contains conserved and novel elements of Gram-negative bacterial porins." PloS one p. e68934, vol. 8, Issue 7 (2013). 11 pages.

Ferrara L.G.M. et al., "MOMP from Campylobacter jejuni Is a Trimer of 18-Stranded beta-Barrel Monomers with a Ca(2+) Ion Bound at the Constriction Zone." J Mol Biol (2016), 428(22), pp. 4528-4543. 16 pages.

Final Office Action for U.S. Appl. No. 15/499,855, filed Apr. 27, 2017 on behalf of Lawrence Livermore National Laboratory Mail Date: Aug. 8, 2019 11 pages.

Findlay H.E, et al., "Surface expression, single-channel analysis and membrane topology of recombinant Chlamydia trachomatis Major Outer Membrane Protein" *BMC Microbiol*, 5:5 (2005). 15 pages.

Ghosh M, et al., "Cationic lipid Nanodisks as an siRNA delivery vehicle" Biochem Cell Biol (2014), 92(3): 200-205. 14 pages.

Gref et al., "Biodegradable Long-Circulating Polymeric Nanospheres" Science American Association for the Advancement of Science vol. 263 No. 5153, p. 1600-1603 (1994).

Haque F, et al., "Incorporation of a viral DNA-packaging motor channel in lipid bilayers for real-time, single-molecule sensing of chemicals and double-stranded DNA." Nat Protoc, vol. 8, No. 2, pp. 373-392 (2013).

He W, et al., "Cell-free expression of functional receptor tyrosine kinases" *Sci Rep*, 5:12896 (2015). 8 pages.

He W, et al., "Producing Membrane Bound Proteins as Countermeasures to infectious Diseases" Synthetic Genomics Vaccines (2016).

Inic-Kanada A, et al., "A Probiotic Adjuvant Lactobacillus rhamnosus Enhances Specific Immune Responses after Ocular Mucosal Immunization with Chlamydial Polymorphic Membrane Protein C." PLoS One p. e015785 (2016) 14 pages.

International Preliminary Report on Patentability for International Application No. PCT/US2018/030537 filed on May 1, 2018 on behalf of Lawrence Livermore National Security. Mail Date: Nov. 14, 2019. 11 pages.

International Search Report and Written Opinion for PCT/US2009/057852, 19 pages, mailed on May 6, 2010.

International Search Report and Written Opinion for PCT/US2012/070508, 9 pages, mailed on Feb. 27, 2013.

International Search Report for International Application No. PCT/US2018/030537 filed on May 1, 2018 on behalf of Lawrence Livermore National Security Mail Date: Jan. 17, 2019 5 pages.

Johnson R.M. et al., "PmpG 303-311, a protective vaccine epitope that elicits persistent cellular immune responses in Chlamydia muridarum-immune mice." Infect Immun, vol. 80, No. 6, p. 2204-2211 (2012).

Karunakaran K.P. et al., "Immunoproteomic discovery of novel T cell antigens from the obligate intracellular pathogen Chlamydia" J Immunol p. 2459-65 (2008).

Karunakaran K.P. et al., "Outer membrane proteins preferentially load MHC class II peptides: implications for a Chlamydia trachomatis T cell vaccine." Vaccine, 33, p. 2159-2166 (2015).

Keppetipola S, et al., From gene to HSQC in under five hours: high-throughput NMR proteomics: J Am Chem Soc, 128, pp. 4508-4509 (Apr. 2006).

Kigawa T, et al., "Cell-free production and stable-isotope labeling of milligram quantities of proteins" FEBS Lett, 442, pp. 15-19 (Jan. 1999).

Klussman S, et al., "The Aptamer Handbook: Functional Oligonucleotides and Their Applications" *Wiley-VCH* (2006) 509 pages.

Koren E, et al., "Clinical validation of the "in silico" prediction of immunogenicity of a human recombinant therapeutic protein" Clinical Immunology, 124, pp. 26-32 (2007).

Lam K, et al., "A new type of synthetic peptide library for identifying ligand-binding activity" Nature, vol. 354, pp. 82-84 (1991).

Levy-Nissenbaum E. et al., "Nanotechnology and aptamers: applications in drug delivery" *Trends in Biotechnology* 26(8):442-449 (2008).

Li et al., "Antimicrobial Activities of Amine-and Guanidine-Functionalized Cholic Acid Derivatives" Antimicrobial Agents and Chemotherapy vol. 43 (6) p. 1347-1349 (Jun. 1999).

Luo et al., "Asymmetric Poly(ethylene glycol) Star Polymers with a Cholic Acid Core and Their Aggregation Properties" Biomacromolecules vol. 10 No. 4 p. 900-906 (2009).

Luo J, et al., "Well-defined, size-tunable, multifunctional micelles for efficient paclitaxel delivery for cancer treatment." Bioconjug Chem, 21, pp. 1216-1224 (Jul. 2010).

Manning D.S. et al., "Expression of the major outer membrane protein of Chlamydia trachomatis in *Escherichia coli*." Infection and Immunity, vol. 61, No. 10, pp. 4093-4098 (1993).

Mori M, et al., "Cell-free synthesis and processing of a putative precursor for mitochondrial carbamyl phosphate synthetase I of rat liver" Proc Natl Acad Sci USA, vol. 76, No. 10, pp. 5071-5075 (Oct. 1979).

Non-Final Office Action for U.S. Appl. No. 13/719,785, filed Dec. 19, 2012 on behalf of Lawrence Livermore National Laboratory Mail Date: Jun. 4, 2015 8 pages.

Non-Final Office Action for U.S. Appl. No. 15/499,855, filed Apr. 27, 2017, on behalf of Lawrence Livermore National Security LLC. Mail Date: Jan. 11, 2019. 7 pages.

(56) References Cited

OTHER PUBLICATIONS

Notice of Allowance for U.S. Appl. No. 13/719,785, filed Dec. 19, 2012 on behalf of Lawrence Livermore National Laboratory Mail Date: Feb. 17, 2016 7 pages.
Pal S, et al., "Comparison of the nine polymorphic membrane proteins of Chlamydia trachomatis for their ability to induce protective immune responses in mice against a C. muridarum challenge." Vaccine, 35, p. 2543-2549 (2017).
Pal S, et al., "Immunization with an acellular vaccine consisting of the outer membrane complex of Chlamydia trachomatis induces protection against a genital challenge" Infection and Immunity, vol. 65, No. 8, pp. 3361-3369 (1997).
Pal S, et al., "Immunization with the Chlamydia trachomatis mouse pneumonitis major outer membrane protein can elicit a protective immune response against a genital challenge" Infection and immunity, vol. 65, No. 10, pp. 6240-6247 (2001).
Pal S, et al., "Vaccination with the Chlamydia trachomatis major outer membrane protein can elicit an immune response as protective as that resulting from inoculation with live bacteria" Infection and Immunity, vol. 73, No. 12, pp. 8153-8160 (2005).
Ralli-Jain P, et al., "Enhancement of the protective efficacy of a Chlamydia trachomatis recombinant vaccine by combining systemic and mucosal routes for immunization." Vaccine, 28, pp. 7659-7666 (2010).
Rensen PC, et al., "Human recombinant apolipoprotein E-enriched liposomes can mimic low-density lipoproteins as carriers for the site-specific delivery of antitumor agents." Mol Pharmacol, 52, pp. 445-455 (Sep. 1997).
Rodriguez-Maranon M.J. et al., "Prediction of the membrane-spanning Beta-strands of the major outer membrane protein of Chlamydia" Protein Science, 11, pp. 1854-1861 (2006).
Ryan Ro, "Nanobiotechnology applications of reconstituted high density lipoprotein" J Nanobiotechnology, 8:28 (Dec. 2010) 10 pages.
Ryan Ro, "Nanodisks: hydrophobic drug delivery vehicles" Expert Opin Drug Deliv., 5(3), pp. 343-351 (Mar. 2008).
Semple et al., "Rational design of cationic lipids for siRNA delivery" Nature Biotechnology Feb. 2010, vol. 28, No. 2, pp. 172-176 + 2 additional pages.
Su H, et al., "Immunogenicity of a chimeric peptide corresponding to T helper and B cell epitopes of the Chlamydia trachomatis major outer membrane protein" Journal of Experimental Medicine, vol. 175, pp. 227-235 (1992).
Sun G, et al., "Protection against an intranasal challenge by vaccines formulated with native and recombinant preparations of the Chlamydia trachomatis major outer membrane protein" Vaccine, 27, pp. 5020-5025 (2009).
Sun G, et al., "Structural and functional analyses of the major outer membrane protein of Chlamydia trachomatis" J Bacteriol, vol. 189, No. 17, pp. 6222-6235 (2007).
Sunahara H, et al., "Design and synthesis of a library of BODIPY-based environmental polarity sensors utilizing photoinduced electron-transfer-controlled fluorescence ON/OFF switching" J Am Chem Soc., 129, pp. 5597-5604 (May 2007).
Tang G, et al., "EMAN2: an extensible image processing suite for electron microscopy" J Struct Biol, 157, pp. 38-46 (2007).
Tifrea D.F. et al., "Amphipols stabilize the Chlamydia major outer membrane protein and enhance its protective ability as a vaccine" Vaccine, 29, pp. 4623-4631 (2011).
Tifrea D.F. et al., "Increased immunoaccessibility of MOMP epitopes in a vaccine formulated with amphipols may account for the very robust protection elicited against a vaginal challenge with Chlamydia muridarum" The Journal of Immunology, 192, pp. 5201-5213 (2014).
Tu J, et al., "A multi-epitope vaccine based on Chlamydia trachomatis major outer membrane protein induces specific immunity in mice." Acta biochimica et biophysica Sinica, vol. 46, Issue 5, pp. 401-408 (2014).

Vijayalakshmi et al., "A Simple Construction of a Bile Acid Based Dendritic Light Harvesting System" Organic Letters vol. 7 No. 13 p. 2727-2730 (2005).
Wang Y, et al., "Identification of surface-exposed components of MOMP of Chlamydia trachomatis serovar F." Protein Science, 15, pp. 122-134 (2006).
Written Opinion for International Application No. PCT/US2018/030537 filed on May 1, 2018 on behalf of Lawrence Livermore National Security Mail Date: Jan. 17, 2019 9 pages.
Xiao et al., "PEG oligocholic acid Telodendrimer micelles for the targeted delivery of doxorubicin to B cell lymphoma" Journal of Controlled Release vol. 155 p. 272-281 (2011).
Xiao K, et al., "A self-assembling nanoparticle for paclitaxel delivery in ovarian cancer." Biomaterials, 30 (30), pp. 6006-6016 (2009) 24 pages.
Xiao K, et al., "Telodendrimer-based nanocarriers for the treatment of ovarian cancer." Ther Deliv, 4(10), pp. 1279-1292 (2013) 24 pages.
Yang JP, et al., "Cell-free synthesis of a functional G protein-coupled receptor complexed with nanometer scale bilayer discs." BMC Biotechnol, 11:57, (May 2011) 8 pages.
Zuris J, et al., "Cationic lipid-mediated delivery of proteins enables efficient protein-based genome editing in vitro and in vivo" Nature Biotechnology, vol. 33, No. 1, p. 73-80 (2015) 8 pages.
Advisory Action for U.S. Appl. No. 12/118,530. Mail Date: Jun. 6, 2012, 5 pages.
Anantharamaiah, G.M., et al., "Studies of Synthetic Peptide Analogs of the Amphipathic Helix / Structures of Complexes with Dimyristoyl Phosphatidycholine ," 1985, The Journal of Biological Chemistry, vol. 260, No. 18, 10248-10255.
Aranyi T., et al., "Predictable Difficulty or Difficulty to Predict," Protein Science, Jan. 2011, vol. 20 (1), 3 pages.
Baas B.J., et al., "Homotropic Cooperativity of Monomeric Cytochrome P450 3A4 in a Nanoscale Native Bilayer Environment," Archives of Biochemistry and Biophysics,Oct. 2004, vol. 430 (2), 11 pages.
Bacher G., et al., "Negative and Positive Ion Matrix-Assisted Laser Desorption/Ionization Time-of-Flight Mass Spectrometry and Positive Ion Nano-Electrospray Ionization Quadrupole Ion Trap Mass Spectrometry of Peptidoglycan Fragments Isolated from Various Bacillus Species," Journal of Mass Spectrometry, Feb. 2001, vol. 36 (2), 16 pages.
Bay et al., "Small multidrug resistance proteins: A multidrug transporter family that continues to grow," Biochimica et Biophysica Acta 1778 (2008) 1814-1838.
Bayburt T.H., et al., "Self-Assembly of Single Integral Membrane Proteins into Soluble Nanoscale Phospholipid Bilayers," Protein Science, Nov. 2003, vol. 12 (11), 2476-2481. 6 pages, XP002498218, ISSN: 0961-8368.
Bayburt T.H., et al., "Single-Molecule Height Measurements on Microsomal Cytochrome P450 in Nanometer-Scale Phospholipid Bilayer Disks," Proceedings of the National Academy of Sciences of the United States of America, May 2002, vol. 99 (10), 6725-6730. 6 pages.
Bayburt T.H., et al., "Membrane Protein Assembly into Nanodiscs," FEBS Letters,May 2010, vol. 584 (9), 7 pages.
Bayburt T.H., et al., "Transducin Activation by Nanoscale Lipid Bilayers Containing One and Two Rhodopsins," The Journal of Biological Chemistry, May 2007, vol. 282 (20), 8 pages.
Beja O., et al., "Bacterial Rhodopsin: Evidence for a New Type of Phototrophy in the Sea," Science,Sep. 2000, vol. 289 (5486), 6 pages.
Bockaert J., et al., "Do Recombinant Receptor Assays Provide Affinity and Potency Estimates?,"In Receptor Classification: The Integration of Operational, Structural, and Transductional Information,1997, vol. 812, New York, New York Academy of Sciences, 16 pages.
Chung, B.H., et al., "Studies of Synthetic Peptide Analogs of the Amphipathic Helix / Correlation of Structure with Function," 1985, The Journal of Biological Chemistry, vol. 260, No. 18, 10256-10262.
Civjan N., et al., "Direct Solubilization of Heterologously Expressed Membrane Proteins by Incorporation Into Nanoscale Lipid Bilayer," Biotechniques,Sep. 2003, vol. 35 (3), 6 pages.

(56) References Cited

OTHER PUBLICATIONS

Cruz F., et al., "Kinetic Properties of Recombinant MAO-A on Incorporation into Phospholipid Nanodisks," *Journal of Neural Transmission*,2007, vol. 114 (6), 4 pages.

Cullis P.R., et al., "Physical Properties and Functional Roles of Lipids in Membranes," *New Comprehensive Biochemistry*,1991, vol. 20, 41 pages.

Dawson P.E., et al., "Synthesis of Native Proteins by Chemical Ligation," *Annual Review of Biochemistry*,2000, vol. 69, 923-960. 39 pages.

Dengue Fever Climbs the Social Ladder, Special Report, *Nature*,Aug. 2007, vol. 448, 2 pages.

Dong, C., et al., "Regulation of G protein-coupled receptor export trafficking," Biochimica et Biophysica Acta 1768 (2006) 853-870.

Final Office Action for U.S. Appl. No. 12/118,530. Mail Date: Jan. 25, 2012, 37 pages.

Final Office Action for U.S. Appl. No. 12/118,530. Mail Date: Mar. 6, 2015, 52 pages.

Final Office Action for U.S. Appl. No. 12/469,533. Mail Date: Dec. 4, 2012, 7 pages.

Final Office Action for U.S. Appl. No. 12/469,533. Mail Date: Oct. 24, 2011, 11 pages.

Frydman J., et al., "Principles of Chaperone-assisted Protein Folding: Differences Between in Vitro and in Vivo Mechanisms," Science, Jun. 1996, vol. 272 (5267), 6 pages.

G Protein-coupled Receptor[online], Retrieved from the Internet: URL: Wikipedia 2008, https://web.archive.org/web/20080224232212/://en.wikipedia.org/wiki/G.protein-coupled.receptor, 2008, 7 pages.

Imura, T., et al., "Minimum Amino Acid Residues of an a-Helical Peptide Leading to Lipid Nanodisc Formation," 2014, J. Oleo Sci. 63, (11) 1203-1208.

Imura, T., et al., "Surfactant-like Properties of an Amphilic a-Helical Peptide Leading to Lipid Nanodisc Formation," 2014, Langmuir, 30, 4752-4759.

"Individual" from Merriam-Webster, Jan. 13, 2015, accessed via WayBackMachine.com (2 pages).

International Preliminary Report on Patentability for Application No. PCT/US2008/063307, Mail Date: Nov. 10, 2009, 7 pages.

International Preliminary Report on Patentability for Application No. PCT/US2016/051172 filed Sep. 9, 2016 on behalf of Lawrence Livermore National Security, LLC. Mail Date: Mar. 13, 2018. 8 pages. (English Only).

International Search Report for Application No. PCT/US2008/063307, Mail Date: Oct. 29, 2008, 5 pages.

International Search Report for Application No. PCT/US2016/051172, Mail Date: Dec. 13, 2016., 6 pages.

"Ion channel", Wikipedia, accessed Dec. 22, 2014, pp. 1-8, 8 pages.

Ishihara G., et al., "Expression of G Protein Coupled Receptors in a Cell-free Translational System Using Detergents and Thioredoxin-fusion Vectors," *Protein Expression and Purification*,May 2005, vol. 41 (1), 11 pages.

Jonas A., "Defined Apolipoprotein A-I Conformations in Reconstituted High Density Lipoprotein Discs," *The Journal of Biological Chemistry*, Mar. 1989, vol. 264 (9), 7 pages.

Jonas A., "Reconstitution of High-density Lipoproteins," Methods in Enzymology, 1986, vol. 128, 7 pages.

Jones M.K., et al., "Computer Programs to Identify and Classify Amphipathic alpha Helical Domains," Journal of Lipid Research, Feb. 1992, vol. 33 (2), 287-296. 10 pages.

Klammt C., et al., "Cell-free Production of G Protein-coupled Receptors for Functional and Structural Studies," *Journal of Structural Biology*,Jul. 2007, vol. 158, 13 pages.

Lam K.S., et al., "Application of Combinatorial Library Methods in Cancer Research and Drug Discovery," Anti-cancer Drug Design, Apr. 1997, vol. 12 (3), 145-167. 24 pages.

"Microsome" from Wikipedia, Mar. 3, 2008, accessed via WayBackMachine.com (1 page).

Midtgaard, S.R., et al., "Self-assembling peptides form nanodiscs that stabilize membrane proteins," 2014, Soft Matter, 10, 738-752.

Nanodisc Trademark #78166119, Owner: Sligar, Stephen G., Retrieved from the Internet:[URL:https://inventively.com/search/trademarks/78166119], retrieved on Aug. 4, 2015, 2 pages.

Non-Final Office Action for U.S. Appl. No. 12/118,530. Mail Date: Aug. 30, 2011, 28 pages.

Non-Final Office Action for U.S. Appl. No. 12/118,530. Mail Date: Jul. 24, 2014, 33 pages.

Non-Final Office Action for U.S. Appl. No. 12/469,533. Mail Date: May 23, 2012, 15 pages.

North P., et al., "Alteration of Synaptic Membrane Cholesterol/Phospholipid Ratio Using a Lipid Transfer Protein, Effect on Gamma-aminobutyric Acid Uptake," *The Journal of Biological Chemistry*,Jan. 1983, vol. 258 (2), 12 pages.

Notice of Allowance for U.S. Appl. No. 12/469,533. Mail Date: Jul. 3, 2014, 13 pages.

Pasini E.M., et al., "In-Depth Analysis of the Membranes and Cytosolic Proteome of Red Blood Cells," Blood, Aug. 2006, vol. 180 (3), 12 pages.

Patel J.D., et al., "Preparation and Characterization of Nickel Nanoparticles for Binding to His-Tag Proteins and Antigens," *Pharmaceutical Research*,Feb. 2007, vol. 24 (2), 10 pages.

Peters-Libeau C.A., et al., "Model of Biologically Active Apolipoprotein E Bound to Dipalmitoylphosphatidylcholine," *The Journal of Biological Chemistry*,Jan. 2006, vol. 281 (2), 8 pages.

Restriction Requirement for U.S. Appl. No. 12/118,530, filed May 9, 2008. Mail Date: Sep. 24, 2010, 14 pages.

Restriction Requirement for U.S. Appl. No. 12/118,530. Mail Date: Mar. 30, 2011, 10 pages.

Restriction Requirement for U.S. Appl. No. 12/469,533. Mail Date: Jun. 7, 2011, 8 pages.

Restriction Requirement for U.S. Appl. No. 15/744,754, filed Jan. 12, 2018 on behalf of Lawrence Livermore National Laboratory Mail Date: Aug. 7, 2019 9 pages.

Rüger R., et al., "In Vitro Characterization of Binding and Stability of Single-Chain Fv Ni-NTA-Liposomes," *Journal of Drug Targeting*,Sep. 2006, vol. 14(8), 7 pages.

Sawasaki T., et al., "A Bilayer Cell-Free Protein Synthesis System for High-Throughput Screening of Gene Products," *FEBS Letters*,Mar. 6, 2002, vol. 514(1), 4 pages.

Schmitt L., et al., "Synthesis and Characterization of Chelator-Lipids for Reversible Immobilization of Engineered Proteins at Self-Assembled Lipid Interfaces,"*Journal of the American Chemical Society*,1994, vol. 116 (19), 7 pages.

Segota S., et al., "Spontaneous Formation of Vesicles," *Advances in Colloid and Interface Science*,Sep. 2006, vol. 121, pp. 51-75, 25 pages.

Shaw A.W., et al., "Phospholipid Phase Transitions in Homogeneous Nanometer Scale Bilayer Discs," *FEBS letters*, Jan. 2004, vol. 556 (1-3), 5 pages.

Shih A.Y., et al., "Molecular Dynamics Simulations of Discoidal Bilayers Assembled from Truncated Human Lipoproteins," *Biophysical Journal*, Jan. 2005, vol. 88 (1), 9 pages.

Sligar, S., "Overview of Nanodisc Technology" from Sligar Lab, accessed Nov. 21, 2014 (1 page).

Sligar webpage http://sligarlab.life.uiuc.edu/nanodisc.html, accessed Feb. 28, 2018. "Nanodisc Technology: Soluble Lipid Bilayer Systems for Structural and Functional Studies of Membrane Proteins" (3 pages).

Sperling R.A., et al., "Surface Modification, Functionalization and Bloconjugation of Colloidal Inorganic Nanoparticles," Philosophical Transactions of the Royal Society A, Mar. 2010, vol. 368, 1333-1383, 51 pages.

Sun P.D., et al., "Overview of Protein Structural and Functional Folds," *Current Protocols in Protein Science*,May 2004, vol. 35, 3 pages.

Svetina S., et al., "Shape Behavior of Lipid Vesicles as the Basis of Some Cellular Processes," The Anatomical Record, Nov. 2002, vol. 268 (3), 215-225. 11 pages.

Toniolo C. et al., "Lipopeptaibols, a novel family of membrane active, antimicrobial peptides" *Cellular and Molecular Life Sciences*, vol. 58,2001, pp. 1179-1188, 10 pages.

Tufteland M., et al., "Peptide Stabilized Amphotericin B Nanodisks," *Peptides*,Apr. 2007, vol. 28 (4), 6 pages.

(56) References Cited

OTHER PUBLICATIONS

"Vesicle" from Wikipedia, Dec. 16, 2008, accessed via WayBackMachine.com (5 pages).
Wallin E., et al., "Genome-Wide Analysis of Integral Membrane Proteins from Eubacterial, Archaean, and Eukaryotic Organisms," *Protein Science*, Apr. 1998, vol. 7 (4), 10 pages.
Whorton M.R., et al., "A Monomeric G Protein-Coupled Receptor Isolated in a High-Density Lipoprotein Particle Efficiently Activates its G Protein," Proceedings of the National Academy of Sciences, May 2007, vol. 104 (18), 7682-7687. 6 pages.
Written Opinion for Application No. PCT/US2008/063307, Mail Date: Oct. 29, 2008, 6 pages.
Written Opinion for Application No. PCT/US2016/051172, Mail Date: Dec. 13, 2016, 7 pages.
Advisory Action for U.S. Appl. No. 15/499,855, filed Apr. 27, 2017 on behalf of Lawrence Livermore National Security, LLC. Mail Date: Dec. 31, 2019. 3 pages.
De Filippis et al., "Enhanced Protein Thermostability by Ala → Aib Replacement," *Biochemistry* 1998, 37, 1686-1696. 11 Pages.
Non-Final Office Action for U.S. Appl. No. 15/744,754, filed Jan. 12, 2018 on behalf of Lawrence Livermore National Laboratory. Mail Date: Mar. 4, 2020. 53 pages.
Non-Final Office Action for U.S. Appl. No. 16/082,924, filed Sep. 6, 2018 on behalf of Lawrence Livermore National Security, LLC. Mail Date: Jan. 31, 2020 25 pages.
Notice of Allowance for U.S. Appl. No. 15/499,855, filed Apr. 27, 2017 on behalf of Lawrence Livermore National Security, LLC. Mail Date: Mar. 5, 2020. 43 Pages.
PDB database search for oxysterol binding protein, retrieved from the Internet: <http://www.rcsb.org/pdb/results/results.do?tabtoshow=Current&qrid=37B93383>, retrieved onFeb. 20, 2020. 7 Pages.
Reinau M. et al. "The Diversity of FtsY-Lipid Interactions" *Biopolymers*, vol. 3, No. 7, Jan. 2010, pp. 595-606 12 pages.
Ruchala et al., "Oxpholipin 11D: An Anti-Inflammatory Peptide That Binds Cholesterol and Oxidized Phospholipids," PLoS One, Apr. 2010, vol. 5, Issue 4, e10181. 13 pages.
Adamczyk J., et al., "The Isotope Array, a New Tool That Employs Substrate-Mediated Labeling of rRNA for Determination of Microbial Community Structure and Function,". *Applied and environmental microbiology*, Nov. 2003, vol. 69 (11), 13 pages.
Adams, M.W.W., et al., "Hydrogenase," 1981, Biochimica et Biophysica Acta 594, 105-176.
Addison S.L., et al., "Stable Isotope Probing: Technical Considerations When Resolving (15)N-labeled RNA in Gradients," *Journal of Microbiological Methods*, Jan. 2010, vol. 80(1), 6 pages.
Bayburt T.H., et al., "Self-Assembly of Discoidal Phospholipid Bilayer Nanoparticles with Membrane Scaffold Proteins," Nano Letters, 2002, vol. 2 (8), 4 pages.
Boldog T., et al., "Nanodiscs Separate Chemoreceptor Oligomeric States and Reveal Their Signalling Properties," *Proceedings of the National Academy of Sciences of the United States of America*, Aug. 2006, vol. 103 (31), 11509-11514. 6 pages.
Boldog T., et al., "Using Nanodiscs to Create Water-soluble Transmembrane Chemoreceptors Inserted in Lipid Bilayer," *Methods in Enzymology*, 2007, vol. 423, 317-335. 19 pages.
Brodie E.L., et al., "Urban Aerosols Harbor Diverse and Dynamic Bacterial Populations," Proceedings of the National Academy of Sciences of the United States of America, Jan. 2007, vol. 104 (1), 299-304. 6 pages.
Burgdorf T., et al., "The Soluble NAD+-Reducing [NiFe]-Hydrogenase from Ralstonia eutropha H16 Consists of Six Subunits and can be Specifically Activated by NADPH," Journal of Bacteriology, May 2005, vol. 187 (9), 3122-3132. 11 pages.
Casey P.J., et al., "Protein Prenyltransferases," *Journal of Biological Chemistry*, Mar. 1996, vol. 271 (10), 5289-5292. 5 pages.
Chefson A., et al., "Progress Towards the Easier Use of P450 Enzymes," *Molecular Biosystems*, Oct. 2006, vol. 2 (10), 462-469. 8 pages.

Choquet C.G., et al., "Stability of Pressure-extruded Liposomes Made From Archaeobacterial Ether Lipids," *Applied Microbiology and Biotechnology*, Nov. 1994, vol. 42 (2-3), 10 pages.
Cornish K., et al., "Characterization of Cis-Prenyl Transferase Activity Localised in a Buoyant Fraction of Rubber Particles From Ficus Elastica Latex," *Plant Physiology and Biochemistry*, May/Jun. 1996, vol. 34 (3), 377-384. 10 pages.
Cornish K., et al., "Natural Rubber biosynthesis in Plants: Rubber Transferase," Methods in Enzymology, 2012, vol. 515, 63-82. 20 pages.
Cornish K., et al., "Rubber Biosynthesis in Plants," American Oil Chemist Society, *The Lipid Library*, Nov. 2011, 10 pages.
Das D., et al., "Role of Fe-hydrogenase in Biological Hydrogen Production," Current Science, Jun. 2006, vol. 90 (12), 1627-1637. 11 pages.
Denisov, I.G., et al., "Cytochromes P450 in Nanodiscs," Biochimica et Biophysica Act, 2010, 7 pages.
Donninger C., et al., "An Improved Synthesis of Isopentenyl Pyrophosphate," The Biochemical Journal, Nov. 1967, vol. 105 (2), 545-547. 3 pages.
Dubey R., et al., "Microencapsulation Technology and Applications," Defence Science Journal, Jan. 2009, vol. 59 (1), 82-95. 14 pages.
Elgren T. E. et al., "Immobilization of Active Hydrogenases by Encapsulation in Polymeric Porous Gels," *Nano Letters*, Oct. 2005, vol. 5 (10), 2085-2087. 3 pages.
Final Office Action for U.S. Appl. No. 12/352,472. Mail Date: Jun. 7, 2012, 25 pages.
Final Office Action for U.S. Appl. No. 12/352,472. Mail Date: Jun. 29, 2015, 18 pages.
Friedrich T. et al., "The respiratory complex I of bacteria, archaea and eukarya and its module common with membrane-bound multisubunit hydrogenases." FEBS Lett. Aug. 2000 11;479(1-2):1-5.
Gan L., et al., "Role of NADPH-Cytochrome P450 Reductase and Cytochrome-b-5/NADH-b5 Reductase in Variability of CYP3A Activity in Human Liver Microsomes," *Drug Metabolism and Disposition*, Jan. 2009, vol. 37 (1), 90-96. 7 pages.
Gilbert L., "Insect Development: Morphognesis, molting and Metamorphosis," *Academic Press*, Sep. 18, 2009, 573-574. 2 pages.
Gorrod J.W., et al., "Some Observations on Type I and Type II Microsomal Binding Spectra," *Xenobiotica*, Jul.-Oct. 1971, vol. 1 (4), 521-522. 2 pages.
Greve, H-H., "Rubber, 2. Natural" in *Ullmann's Encyclopedia of Industrial Chemistry* vol. 31 (2012) 583-596. Wiley-VCH Verlag GmbH & Co. KGaA, Weinheim, 14 pages.
Grinkova, Y.V., et al., "Engineering extended membrane scaffold proteins for self-assembly of soluble nanoscale lipid bilayers," Protein Engineering, Design and Selection, 2010, vol. 23, No. 11, pp. 843-848.
Gronover C.S., et al., "Natural Rubber Biosynthesis and Physics-Chemical Studies on Plant Derived Latex," *Biotechnology of Biopolymers*, Jul. 2011, 75-88.15 pages.
Hallenbeck P.C. et al., "Biological Hydrogen Production: Fundamentals and Limiting Processes," *International Journal of Hydrogen Energy*, Nov. 2002, vol. 27 (11-12), 1185-1193. 9 pages.
Hasemann C.A., et al., "Structure and Function of Cytochromes P450: a Comparative Analysis of Three Crystal Structures," *Structure*, Jan. 1995, vol. 3 (1), 22 pages.
Hein C.D., et al., "Click Chemistry, A Powerful Tool for Pharmaceutical Sciences," *Pharmaceutical Research*, Oct. 2008, vol. 25 (10), 30 pages.
Hiraishi T., et al., "Enzyme-catalyzed Synthesis and Degradation of Biopolymers," *Mini-Reviews in Organic Chemistry, Bentham Science Publishers*, Feb. 2009, vol. 6 (1), 11 pages.
Ho D., et al., "Fabrication of Biomolecule-copolymer Hybrid Nanovesicles as Energy Conversion Systems," *Nanotechnology*, Nov. 2005, vol. 16 (12), 13 pages.
Kurkin S., et al., "The Membrane-bound [NiFe]-hydrogenase (Ech) From Methanosarcina Barkeri: Unusual Properties of the Iron-sulphur Clusters," *European Journal of Biochemistry*, Dec. 2002, vol. 269 (24), 6101-6111. 11 pages.

(56) References Cited

OTHER PUBLICATIONS

Lechene C., et al., "High-resolution Quantitative Imaging of Mammalian and Bacterial Cells Using Stable Isotope Mass Spectrometry," *Journal of Biology*, 2006, vol. 5 (6), article 20, 30 pages.
Leitz A.J., et al., "Functional Reconstitution of Beta2-adrenergic Receptors Utilizing Self-assembling Nanodisc Technology," *Biotechniques*, May 2006, vol. 40 (5), 6 pages.
Long M., et al., "Characterization of a HoxEFUYH type of [NiFe] Hydrogenase from Allochromatium Vinosum and Some EPR and IR Properties of the Hydrogenase Module," *Journal of Biological Inorganic Chemistry*, Jan. 2007, vol. 12 (1), 18 pages.
McIntosh C.L., et al., "The [NiFe]-Hydrogenase of the *Cyanobacterium synechocystis* sp. PCC 6803 Works Bidirectionally with a Bias to H2 Production," *Journal of the American Chemical Society*, Jun. 2011, vol. 133 (29), 12 pages.
McTernan P.M., et al., "Intact Functional Fourteen-Subunit Respiratory Membrane-Bound [NiFe]-Hydrogenase Complex of the Hyperthermophilic Archaeon Pyrococcus Furiosus," *Journal of Biological Chemistry*, Jul. 2014, vol. 289 (28), 10 pages.
Meuer J., et al., "Purification and Catalytic Properties of Ech Hydrogenase From Methanosarcina Barkeri," *European Journal of Biochemistry*, Oct. 1999, vol. 265 (1), 11 pages.
Meyer J., "[Fe/Fe] Hydrogenases and Their Evolution: A Genomic Perspective," *Cellular and Molecular Life Sciences*, May 2007, vol. 64 (9), 1063-1084. 22 pages.
Nath A et al., "Applications of Phospholipid Bilayer Nanodiscs in the Study of Membranes and Membrane Proteins," Biochemistry, Feb. 2007, vol. 46 (8), 11 pages.
Non-Final Office Action for U.S. Appl. No. 12/352,472. Mail Date: Aug. 12, 2016, 31 pages.
Non-Final Office Action for U.S. Appl. No. 12/352,472. Mail Date: Dec. 26, 2014, 24 pages.
Non-Final Office Action for U.S. Appl. No. 12/352,472. Mail Date: Oct. 2, 2013, 19 pages.
Non-Final Office Action for U.S. Appl. No. 12/352,472. Mail Date: Sep. 22, 2011, 21 pages.
Non-Final Office Action for U.S. Appl. No. 12/352,548. Mail Date: Sep. 13, 2011, 19 pages.
Non-Final Office Action for U.S. Appl. No. 14/536,513. Mail Date: Mar. 24, 2016, 19 pages.
Notice of Allowance for U.S. Appl. No. 12/352,472. Mail Date: Mar. 17, 2017, 12 pages.
Notice of Allowance for U.S. Appl. No. 12/352,548. Mail Date: Apr. 25, 2014, 9 pages.
Notice of Allowance for U.S. Appl. No. 12/352,548. Mail Date: Aug. 5, 2014, 8 pages.
Notice of Allowance for U.S. Appl. No. 12/352,548. Mail Date: Mar. 12, 2012, 10 pages.
Notice of Allowance for U.S. Appl. No. 14/536,513. Mail Date: Jul. 14, 2016, 5 pages.
Ohya N., et al., "Biosynthesis of Natural Rubber and Other Natural Polyisoprenoids," Biopolymers Polyisoprenoids, Jan. 2005, 73-81. 9 pages.
Pan Z., et al., "The Major Protein of Guayule Rubber Particles is a Cytochrome P450: Characterization based on cDNA Cloning and Spectroscopic Analysis of the Solubilized Enzyme and Its Reaction Products," The Journal of Biological Chemistry, Apr. 1995, vol. 270 (15), 8487-8494. 8 pages.
Paterson-Jones J.C., et al., "The Biosynthesis of Natural Rubber," Journal of Plant Physiology, Jun. 1990, vol. 136 (3), 7 pages.
Persson B., et al., "Topology Prediction of Membrane Proteins," Protein Science, Feb. 1996, vol. 5 (2), 9 pages.
Ponciano G., et al., "Transcriptome and Gene Expression Analysis in Cold-Acclimated Guayule (*Parthenium argentum*) Rubber-Producing Tissue," Phytochemistry, Jul. 2012, vol. 79, 12 pages.
Rakhely G., et al., "Cyanobacterial-Type, Heteropentameric, NAD+-Reducing NiFe Hydrogenase in the Purple Sulfur Photosynthetic Bacterium Thiocapsa Roseopersicina," Applied and Environmental Microbiology, Feb. 2004, vol. 70 (2), 7 pages.
Rapp V. et al., "Predicting Fuel Performance for Future HCCI Engines" Combust. Sci. Technol., 185: 735-748, Apr. 20, 2013. 15 pages.
Restriction Requirement for U.S. Appl. No. 12/352,472. Mail Date: May 27, 2011, 8 pages.
Restriction Requirement for U.S. Appl. No. 12/352,548. Mail Date: Apr. 25, 2011, 6 pages.
Sabatini, D.D., et al., "Mechanisms for the Incorporation of Proteins in Membranes and Organelles," Jan. 1, 1982, The Journal of Cell Biology, vol. 92, 1-22.
Sanderson K., "Chemistry: The Photon Trap," Nature, Mar. 27, 2008, vol. 452(7186), 3 pages.
Sapra R., et al., "A Simple Energy-Conserving System: Proton Reduction Coupled to Proton Translocation," Proceedings of the National Academy of Sciences of the United States of America, Jun. 24, 2003, vol. 100(13), 6 pages.
Sapra R., et al., "Purification and Characterization of a Membrane-Bound Hydrogenase from the Hyperthermophilic Archaeon Pyrococcus Furiosus," Journal of Bacteriology, Jun. 2000, vol. 182(12), 6 pages.
Schmidt T., et al., "Characterization of Rubber Particles and Rubber Chain Elongation in Taraxacum Koksaghyz," BMC Biochemistry, Feb. 19, 2010, vol. 11, 11 pages.
Schmitz O., et al., "HoxE—A Subunit Specific for the Pentameric Bidirectional Hydrogenase Complex (HoxEFUYH) of Cyanobacteria," Biochimica et Biophysica Acta, Apr. 22, 2002, vol. 1554(1-2), 9 pages.
Siler D.J., et al., "Composition of Rubber Particles of Hevea Brasiliensis, Parthenium Argentatum, Ficus Elastics and Euphorbia Lactiflua Indicates Unconventional Surface Structure," Plant Physiology and Biochemistry, Jan. 1997, vol. 35 (11), 9 pages.
Silvius J.R., "Thermotropic Phase Transitions of Pure Lipids in Model Membranes and their Modification by Membrane Proteins," Lipid-Protein Interactions, 1982, vol. 2, pp. 239-281, 43 pages.
Singer, S.J., et al., "The Fluid Mosaic Model of the Structure of Cell Membranes," Feb. 1972, Science, vol. 175, 720-731.
Singh A.P., et al., "The Micromorphology and Protein Characterization of Rubber Particles in Ficus Carica, Ficus Benghalensis and Hevea Brasiliensis," Journal of Experimental Botany, Mar. 2003, vol. 54 (384), 8 pages.
Smith D. et al., "Solubilisation of methane monooxygenase from *Methylococcus capsulatus* (Bath)" Eur. J. Biochem, 182, pp. 667-671, Jan. 17, 1989, 5 pages.
Soboh B., et al., "Purification and Catalytic Properties of a CO-Oxidizing: H2-Evolving Enzyme Complex from Carboxydothermus Hydrogenoformans," European Journal of Biochemistry, Nov. 2002, vol. 269 (22), 10 pages.
Stadermann F.J., et al., "Nanosims: The Next Generation Ion Probe for the Microanalysis of ExtraTerrestrial Material," Meteoritics and Planetary Science, 36342, vol. 34 (4), 1999. 2 pages.
Stryer L., et al., "Oxygen Binds to a Heme Prosthetic Group: Biochemistry," 1995, 4th edition, 1 page.
Vincent K. A., et al., "Electrocatalytic Hydrogen Oxidation by an Enzyme at High Carbon Monoxide or Oxygen Levels," *Proceedings of the National Academy of Sciences*, Nov. 2005, vol. 102 (47), 4 pages.
Vincent K. A., et al., "Investigating and Exploiting the Electrocatalytic Properties of Hydrogenases," *Chemical Reviews*, 2007, vol. 107 (10), 48 pages.
Whalen M., et al., "Development of Crops to Produce Industrially Useful Natural Rubber," *Isoprenoid Synthesis in Plants and Microorganisms*, Jan. 2013, vol. 23, 17 pages.
White, S., Membrane Protein Insertion: The Biology-Physics Nexus, Apr. 16, 2007, J. Gen. Physiol., vol. 129, No. 5, 363-369.
Wikipedia—Bacteriorhodopsin, 2 pages, (Downloaded from the internet on Jun. 22, 2015).
Wikipedia., Hydrogenase retrieved from en.wikipedia.org/wiki/Hydrogenase on Nov. 6, 2012, 4 pages.
Woodward J., et al., "Enzymatic Production of Biohydrogen," *Nature*, Jun. 2000, vol. 405 (6790), 2 pages.
Woodward J., et al., "In Vitro Hydrogen Production by Glucose Dehydrogenase and Hydrogenase," *Nature Biotechnology*, Jul. 1996, vol. 14 (7), 3 pages.

(56) References Cited

OTHER PUBLICATIONS

Wu, L., et al., "Membrane targeting and translocation of bacterial hydrogenases," 2000, Arch Microbiology, 173:319-324.
Xie W., et al., "Initiation of Rubber Biosynthesis: In Vitro Comparisons of Benzophenone-Modified Diphosphate Analogues in Three Rubber-Producing Species," *Phytochemistry*, Oct. 2008, vol. 69 (14), 7 pages.
Zhang Y.H., et al., "High-Yield Hydrogen Production from Starch and Water by a Synthetic Enzymatic Pathway," *PLoS One*, May 2007, vol. 2 (5), e456, 6 pages.
Zhanhua C., et al., "Protein Subunit Interfaces: Heterodimers versus Homodimers," *Bioinformation*, Aug. 2005, vol. 1 (2), 12 pages.
Akkaladevi, N., et al., Assembly of Anthrax Toxin Pore: Lethal-Factor Complexes into Lipid Nanodiscs, Protein Science, vol. 22, pp. 492-501, (2013).
Allen, T.M., et al., "Drug Delivery Systems: Entering the Mainstream.", Science, vol. 303(5665), pp. 1818-1822, (2004), 6 pages.
Baylon, J.L., et al., "Characterizing the Membrane-Bound State of Cytochrome P450 3A4: Structure, Depth of Insertion, and Orientation.", Journal of the American Chemical Society, 135(23), pp. 8542-8551, (2013), 11 pages.
Bhattacharya, P., et al., "Nanodisc-Incorporated Hemagglutinin Provides Protective Immunity against Influenza Virus Infection.", Journal of Virology, 84(1), pp. 361-371, (2010).
Blanchette, C.D., et al., "Atomic Force Microscopy Differentiates Discrete Size Distributions Between Membrane Protein Containing and Empty Nanolipoprotein Particles.", Biochimica et Biophysica Acta (BBA)-Biomembranes, 1788(3), pp. 724-731, (2009).
Blanchette, C.D., et al., "Characterization and Purification of Polydisperse Reconstituted Lipoproteins and Nanolipoprotein Particles.", International Journal of Molecular Sciences, 10(7), pp. 2958-2971, (2009).
Blanchette, C.D., et al., "Quantifying Size Distributions of Nanolipoprotein Particles with Single-Particle Analysis and Molecular Dynamic Simulations.", Journal of Lipid Research, 49(7), pp. 1420-1430, (2008), 12 pages.
Bolikal, D., et al., "Degree of Polymerization of a Vesicle Membrane.", Macromolecules, 17(6), pp. 1287-1289, (1984).
Cappuccio, J.A., et al., "Cell-Free Expression for Nanolipoprotein Particles: Building a High-Throughput Membrane Protein Solubility Platform.", High Throughout Protein Expression and Purification, Springer, pp. 273-295, (2009), 24 pages.
Cappuccio, J.A., et al., "Cell-Free Co-Expression of Functional Membrane Proteins and Apolipoprotein, Forming Soluble Nanolipoprotein Particles.", Molecular & Cellular Proteomics, 7(11), pp. 2246-2253, (2008).
Cho, K., et al., "Therapeutic Nanoparticles for Drug Delivery in Cancer.", Clinical Cancer Research, 14(5), pp. 1310-1316, (2008), 8 pages.
Chromy, B.A., et al., "Different Apolipoproteins Impact Nanolipoprotein Particle Formation.", Journal of the American Chemical Society, vol. 129, No. 46, pp. 14348-14354, (2007).
Das, A., et al., "Screening of Type I and II Drug Binding to Human Cytochrome P450-3A4 in Nanodiscs by Localized Surface Plasmon Resonance Spectroscopy.", Analytical Chemistry, 81(10), pp. 3754-3759, (2009), 14 pages.
Fischer, N.O., et al., "Conjugation to Nickel-Chelating Nanolipoprotein Particles Increases the Potency and Efficacy of Subunit Vaccines to Prevent West Nile Encephalitis.", Bioconjugate Chemistry, 21(6), pp. 1018-1022, (2010), 10 pages.
Fischer, N.O., et al., "Evaluation of Nanolipoprotein Particles (NLPs) as an In Vivo Delivery Platform.", Plos One, 9(3), e93342, (2014), 17 pages.
Fischer, N. O., et al., "Immobilization of His-Tagged Proteins on Nickel-Chelating Nanolipoprotein Particles." Bioconjugate Chemistry, vol. 20, No. 3, pp. 460-465, (2009).
Fischer, N. O., et al., "Isolation, characterization, and stability of discretely-sized nanolipoprotein particles assembled with Apolipophor in-III." PLOS one, Jul. 2010, vol. 5, No. 7, e11643, 10 pages.

Gao, T.J., et al., "Characterization of De Novo Synthesized GPCRs Supported in Nanolipoprotein Discs.", PLoS One, 7(9), e44911, (2012), 8 pages.
Gao, T.J., et al., "Characterizing Diffusion Dynamics of a Membrane Protein Associated with Nanolipoproteins Using Fluorescence Correlation Spectroscopy.", Protein Science, 20(2), pp. 437-447, (2011).
Justesen, B.H., et al., "Isolation of Monodisperse Nanodisc-Reconstituted Membrane Proteins Using Free Flow Electrophoresis.", Analytical Chemistry, 85(7), pp. 3497-3500, (2013), 5 pages.
Katzen, F. et al., "Insertion of Membrane Proteins into Discoidal Membranes Using a Cell-Free Protein Expression Approach.", Journal of Proteome Research, 7(8), pp. 3535-3542, (2008).
Mao, H., et al., "Design and Characterization of Immobilized Enzymes in Microfluidic Systems.", Analytical Chemistry, 74(2), pp. 379-385, (2002).
Miyazaki, M., et al., "Effect of Phospholipid Composition on Discoidal HDL Formation.", Biochimica et Biophysica Acta, 1828(5), pp. 1340-1346. (2013).
Okahata, Y., et al., "Polymerizable Lipid-Corked Capsule Membranes. Polymerization at Different Positions of Corking Lipid Bilayers on the Capsule and Effect of Polymerization on Permeation Behavior." Journal of the American Chemical Society, vol. 110, No. 8, pp. 2495-2500, (1988).
Pavlidou, M., et al., "Nanodiscs Allow Phage Display Selection for Ligands to Non-Linear Epitopes on Membrane Proteins.", PLoS One, 8(9), (2013), 8 pages.
Portet, T., et al., "A New Method for Measuring Edge Tensions and Stability of Lipid Bilayers: Effect of Membrane Composition.", Biophysical Journal, vol. 99, pp. 3264-3273, (2010).
Rawicz, W., et al., "Effect of Chain Length and Unsaturation on Elasticity of Lipid Bilayers.", Biophysical Journal, vol. 79(1), pp. 328-339, (2000).
Regen, S.L., et al., "Polymerized Phosphatidyl Choline Vesicles. Stabilized and Controllable Time-Release Carriers.", Biochemical and Biophysical Research Communications, vol. 101, No. 1, pp. 131-136, (1981).
Rensen, P.C.N. et al., "Recombinant Lipoproteins: Lipoprotein-Like Lipid Particles for Drug Testing.", Advanced Drug Delivery Reviews, 47(2-3), pp. 251-276, (2001).
Sparks, D.L., et al., "Effect of Cholesterol on the Charge and Structure of Apolipoprotein A-I in Recombinant High Density Lipoprotein Particles.", Journal of Biological Chemistry, vol. 268, No. 31, pp. 23250-23257, (1993).
Sparreboom, A., et al., "Comparative Preclinical and Clinical Pharmacokinetics of a Cremopher-Free, Nanoparticle Albumin-Bound Paclitaxel (ABI-007) and Paclitaxel Formulated in Cremophor (Taxol).", Clinical Cancer Research, 11(11), pp. 4136-4143, (2011), 9 pages.
Tark, S.H., et al., "Nanomechanical Detection of Cholera Toxin Using Microcantilevers Functionalized with Ganglioside Nanodiscs.", Nanotechnology, 21(43), (2010), 14 pages.
Tieke, B., et al., "Polymerization of Diacetylenes in Multilayers.", Journal of Polymer Science: Polymer Chemistry Edition, 17(6), pp. 1631-1644, (1979).
Tufteland, M., et al., "Nanodisks Derived from Amphotericin B Lipid Complex.", Journal of Pharmaceutical Sciences, 97(10), pp. 4425-4432, (2008), 14 pages.
Tufteland, M., et al., "Peptide Stabilized Amphotericin B Nanodisks.", Peptides, 28(4), pp. 741-746, (2007), 13 pages.
Wadsater, M., et al., "Monitoring Shifts in the Conformation Equilibrium of the Membrane Protein Cytochrome P450 Reductase (POR) in Nanodiscs.", Journal of Biological Chemistry, vol. 287, No. 41, pp. 34596-34603, (2012).
Wang, J., et al., "Tumor Targeting Effects of a Novel Modified Paclitaxel-Loaded Discoidal Mimic High Density Lipoproteins.", Drug Delivery, 20(8), pp. 356-363, (2013), 9 pages.
Weilhammer, D.R., et al., "The Use of Nanolipoprotein Particles to Enhance the Immunostimulatory Properties of Innate Immune Agonists Against Lethal Influenza Challenge.", Biomaterials, 34(38), pp. 10305-10318, (2013), 15 pages.

(56) References Cited

OTHER PUBLICATIONS

Yang, T., et al., "Investigations of Bivalent Antibody Binding on Fluid-Supported Phospholipid Membranes: The Effect of Hapten Density.", Journal of the American Chemical Society, 125(16), pp. 4779-4784, (2003).

Yavlovich, A., et al., "A Novel Class of Photo-Triggerable Liposomes Containing DPPC: DC8, 9PC as Vehicles for Delivery of Doxorubcin to Cells.", Biochemica et Biophysica Acta-Biomembranes, 1808(1), pp. 117-126, (2011), 22 pages.

International Search Report and Written Opinion for PCT/US2016/048632 filed Aug. 25, 2016 on behalf of Lawrence Livermore National Security, LLC, et al. Mail Date: Feb. 6, 2017. 17 pages.

Bacher G., et al., "Charge-reduced Nano Electrospray Ionization Combined with Differential Mobility Analysis of Peptides, Proteins, Glycoproteins, Noncovalent Protein Complexes and Viruses," Journal of Mass Spectrometry, Sep. 2001, vol. 36 (9), 1038-1052. 15 pages.

Baker S.E., et al., "Hydrogen Production by a Hyperthermophilic Membrane-Bound Hydrogenase in Water Soluble Nanolipoprotein Particles," Journal of the American Chemical Society, Nov. 18, 2008, vol. 131 (22), 15 pages.

Barros F., et al., "Modulation of Human erg K+ Channel Gating by Activation of a G Protein-Coupled Receptor and Protein Kinase C," The Journal of Physiology, Sep. 1998, vol. 511 (Pt 2), 333-346. 14 pages.

Bayburt T.H., et al., "Self-Assembly of Discoidal Phospholipid Bilayer Nanoparticles with Membrane Scaffold Proteins," Nano Letters, 2002, vol. 2 (8), 853-856. 11 pages (Additional Pages of Accompanying Online Supplementary Information).

Behrens S., et al., "Linking Microbial Phylogeny to Metabolic Activity at the Single-cell Level by Using Enhanced Element Labeling-Catalyzed Reporter Deposition Fluorescence in Situ Hybridization (EL-FISH) and Nanosims," Applied and Environmental Microbiology, May 2008, vol. 74 (10), 3143-3150. 8 pages.

Berthelot K., et al., "Rubber Elongation Factor (REF), a Major Allergen Component in Hevea Brasiliensis Latex Has Amyloid Properties," PLoS One, 2012, vol. 7 (10), e48065. 12 pages.

Bijsterbosch M.K., et al., "Specific Targeting of a Lipophilic Prodrug of Iododeoxyuridine to Parenchymal Liver Cells Using Lactosylated Reconstituted High Density Lipoprotein Particles," Biochemical Pharmacology, Jul. 1996, vol. 52 (1), 113-121. 10 pages.

Bischler N., et al., "Specific Interaction and Two-Dimensional Crystallization of Histidine Tagged Yeast RNA Polymerase I on Nickel-Chelating Lipids," Biophysical Journal, Mar. 1998, vol. 74 (3), 1522-1532. 11 pages.

Borch J., et al., "Nanodiscs for Immobilization of Lipid Bilayers and Membrane Receptors: Kinetic Analysis of Cholera Toxin Binding to a Glycolipid Receptor," Analytical Chemistry, Aug. 2008, vol. 80 (16), 8 pages.

Boroske E., et al., "Osmotic Shrinkage of Giant Egg-Lecithin Vesicles," Biophysical Journal, Apr. 1981, vol. 34 (1), 95-109. 15 pages.

Boschker H.T.S., et al., "Direct Linking of Microbial Populations to Specific Biogeochemical Processes by 13C-Labelling of Biomarkers," Nature , Apr. 1998, vol. 392, 801-805. 5 pages.

Branden et al., "Introduction to Protein Structure," 2nd edition, Garland Science Publisher, 1999, pp. 3-12. 11 pages.

Brewer S.H., et al., "Formation of Thiolate and Phosphonate Adlayers on Indium-Tin Oxide: Optical and Electronic Characterization," Langmuir, 2002, vol. 18 (18), 6857-6865. 9 pages.

Brodie E.L., et al., "Application of a High-Density Oligonucleotide Microarray Approach To Study Bacterial Population Dynamics during Uranium Reduction and Reoxidation," Applied and Environmental Microbiology, Sep. 2006, vol. 72 (9), 6288-6298. 11 pages.

Brodie E.L., et al., "Profiling Microbial Identity and Activity: Novel Applications of NanoSIMS and High Density Microarrays," Systems Biology Research Strategy & Technology Development, Genomics: GTL Awardee Workshop VI, Department of Energy, 2008, 2 pages.

Brodie et al., Systems Biology Research Strategy and Technology Development: Genomic and Proteomic Strategies. Publicly disclosed on Feb. 13, 2008, http://genomicscience.energy.gov/pubs/2008abstracts/2008GTLabstractstech.pdf, 48 pages.

Brown P.O., et al., "Exploring the New World of the Genome with DNA Microarrays," Nature Genetics, Jan. 1999, vol. 21 (1 Suppl), 33-37. 5 pages.

"Catalytic oxygen removal from coal mine methane," http://www.digitalrefining.com/article/1000623,Catalytic_oxygen_removal_from_coal_mine_methane.html# . . . , accessed Nov. 27, 2017, 4 pages.

Chaung H.C., et al., "CpG Oligodeoxynucleotides as DNA Adjuvants in Vertebrates and their Applications in Immunotherapy," International Immunopharmacology, Oct. 2006, vol. 6 (10), 1586-1596. 11 pages.

Chikh G.G., et al., "Attaching Histidine-Tagged Peptides and Proteins to Lipid-Based Carriers Through Use of Metal-Ion-Chelating Lipids," Biochimica et Biophysica Acta, Dec. 2002, vol. 1567 (1-2), 204-212. 9 pages.

Cline M.S., et al., "Integration of Biological Networks and Gene Expression Data Using Cytoscape," Nature Protocols, 2007, vol. 2 (10), 2366-2382. 17 pages.

Cornish K., "Biochemistry of Natural Rubber, a Vital Raw Material, Emphasizing Biosynthetic Rate, Molecular Weight and Compartmentalization, in Evolutionarily Divergent Plant Species," Natural Product Reports, Apr. 2001, vol. 18 (2), 182-189. 8 pages.

Co-Translation of Iintegral Membrane Proteins (MP) with Membrane Scaffoldproteins (MSP), also known as Nanodiscs[online], Jul. 2015 [ retrieved on Jul. 1, 2015]. Retrieved from the Internet: URL: http://technology.sbkb.org/portal/page/329/, 3 pages.

Cracknell J.A., et al., "Enzymatic Oxidation of H2 in Atmospheric O2: The Electrochemistry of Energy Generation from Trace H2 by Aerobic Microorganisms," Journal of the American Chemical Society, Jan. 2008, vol. 130 (2), 424-425. 2 pages.

Cravatt B.R., et al., "Large-Scale Profiling of Protein Palmitoylation in Mammalian Cells," Nature Methods, Feb. 2009, vol. 6 (2), 135-138. 4 pages.

Cube Biotech, "Assembly of Nanodiscs for use in Cell-Free Expression using MSP1D1 Protein and POPC Phospholipids," 2014, 3 pages.

Cube Biotech, "Nanodisc Assembly Kit MSP1E3D1_POPC," Dec. 2014, 3 pages.

Dalpke A.H., et al., "Phosphodiester CpG Oligonucleotides as Adjuvants:Polyguanosine Runs Enhance Cellular Uptake and Improve Immunostimulative Activity of Phosphodiester CpG Oligonucleotides in Vitro and in Vivo," Immunology, May 2002, vol. 106 (1), 102-112. 11 pages.

Das D., et al., "Hydrogen Production by Biological Processes: A Survey of Literature," International Journal of Hydrogen Energy, Jan. 2001, vol. 26 (1), 13-28. 16 pages.

Desantis T.Z., et al., "Greengenes, a Chimera-checked 16S rRna Gene Database and Workbench Compatible with ARB," Applied and Environmental Microbiology, Jul. 2006, vol. 72 (7), 5069-5072. 5 pages.

Desantis T.Z., et al., "High-Density Universal 16S rRNA Microarray Analysis Reveals Broader Diversity than Typical Clone Library When Sampling the Environment," Microbial Ecology, Apr. 2007, vol. 53 (3), 371-383. 13 pages.

Disalvo E.A., et al., "Surface Changes Induced by Osmotic Shrinkage on Large Unilamellar Vesicles," Chemistry and Physics of Lipids, Nov. 1996, vol. 84 (1), 35-45. 11 pages.

Duan H., et al., "Co-Incorporationof Heterologously Expressed *Arabidopsis* Cytochrome P450 and P450 Reductase into Soluble Nanoscale Lipid Bilayers," Archives of Biochemistry and Biophysics, Apr. 2004, vol. 424 (2), 141-153. 13 pages.

Dumartin B., et al., "Dopamine Tone Regulates D1 Receptor Trafficking and Delivery in Striatal Neurons in Dopamine Transporter-Deficient Mice," Proceedings of the National Academy of Sciences of the United States of America, Feb. 2000, vol. 97 (4), 1879-1884. 6 pages.

Eberly J.O., et al., "Thermotolerant Hydrogenases: Biological Diversity, Properties and Biotechnical Applications," Critical Reviews in Microbiology, Dec. 2008, vol. 34 (3-4), 117-130. 14 pages.

(56) References Cited

OTHER PUBLICATIONS

Final Office Action for U.S. Appl. No. 14/861,750. Mail Date: Feb. 23, 2018, 21 pages.
Fitzgerald K.A., et al., "The Shape of Things to Come," Science, Jun. 2007, vol. 316 (5831), 1574-1576. 4 pages.
Gantz I., et al., "Molecular Cloning of a Gene Encoding the Histamine H2 Receptor," Proceedings of the National Academy of Sciences of the United States of America, Jan. 1991, vol. 88 (2), 429-433. 6 pages.
Gardner T.J., et al., "Systems for Orthogonal Self-assembly of Electroactive Monolayers on Au and ITO: an Approach to Molecular Electronics," Journal of American Chemical Society, Jul. 1995, vol. 117 (26), 6927-6933. 7 pages.
Giannini S.L., et al., "Enhanced Humoral and Memory B Cellular Immunity Using HPV16/18 L1 VLP Vaccine Formulated With the MPL/aluminium Salt Combination (AS04) Compared to Aluminium Salt Only," Vaccine, Aug. 2006, vol. 24 (33-34), 13 pages.
Goldet G., et al., "Hydrogen Production under Aerobic Conditions by Membrane-Bound Hydrogenases from Ralstonia Species,"Journal of American Chemical Society, Jul. 2008, vol. 130 (33), 9 pages.
Guo H.H., et al., "Protein Tolerance to Random Amino Acid Change," Proceedings of the National Academy of Sciences of the United States of America, Jun. 2004, vol. 101 (25), 6 pages.
Gupta R.K ., et al., "Adjuvants for Human Vaccines—current Status, Problems and Future Prospects," Vaccine, Oct. 1995, vol. 13 (14), 14 pages.
Gursky O., et al., "Compex of Human Apolipoprotein C-1 with Phospholipid: Thermodynamic or Kinetic Stability?," Biochemistry, Jun. 2002, vol. 41 (23), 12 pages.
Hamdy S., et al., "Pharmaceutical Analysis of Synthetic Lipid a-based Vaccine Adjuvants in Poly (D, L-lactic-co-glycolic Acid) Nanoparticle Formulations,"Journal of Pharmaceutical and Biomedical Analysis,Aug. 2007, vol. 44 (4), 10 pages.
Hedderich R., "Energy-converting [NiFe] Hydrogenases From Archaea and Extremophiles: Ancestors of Complex I," Journal of Bioenergetics and Biomembranes, Feb. 2004, vol. 36 (1), 11 pages.
Hernandez-Caselles T., et al., "Influence of Liposome Charge and Composition on Their Interaction With Human Blood Serum Proteins," Molecular and Cellular Biochemistry,Mar. 1993, vol. 120 (2), 8 pages.
Hill M.A., et al., "Functional Analysis of Conserved Histidines in ADP-glucose Pyrophosphorylase From Escherichia coli," Biochemical and Biophysical Research Communications,Mar. 1998, vol. 244 (2), 5 pages.
Hong Y., et al., "G-protein-coupled Receptor Microarrays for Multiplexed Compound Screening," Journal of Biomolecular Screening,Jun. 2006, vol. 11 (4), 4 pages.
Huleatt J.W., et al., "Potent Immunogenicity and Efficacy of a Universal Influenza Vaccine Candidate Comprising a Recombinant Fusion Protein Linking Influenza M2e to the TLR5 Ligand Flagellin," Vaccine, Jan. 2008, vol. 26 (2), 14 pages.
International Preliminary Report on Patentability for Application No. PCT/US2009/044722, Mail Date: Nov. 23, 2010, 7 pages.
International Preliminary Report on Patentability for Application No. PCT/US2015/051516 filed Sep. 22, 2015 on behalf of Lawrence Livermore National Security, LLC. Mail Date: Mar. 28, 2017, 10 pages. (English Only).
International Search Report and Written Opinion for Application No. PCT/US2015/051516 filed on Sep. 22, 2015. Mail Date: Jan. 25, 2016, 12 pages.
International Search Report for Application No. PCT/US2009/044722, Mail Date: Oct. 28, 2010, 4 pages.
Jasanada F., et al., "Indium-111 Labeling of Low Density Lipoproteins With the DTPA-bis(Stearylamide): Evaluation as a Potential Radiopharmaceutical for Tumor Localization," Bioconjugate Chemistry, Jan.-Feb. 1996, vol. 7 (1), 10 pages.
Kapdan I.K., et al., "Bio-hydrogen Production from Waste Materials," Enzyme and Microbial Technology,Mar. 2006, vol. 38 (5), 14 pages.

Kolb H.C., et al., "The Growing Impact of Click Chemistryon Drug Discovery," Drug Discovery Today,Dec. 2003, vol. 8 (24), 10 pages.
Konishi E., et al., "Proper Maturation of the Japanese Encephalitis Virus Envelope Glycoprotein Requires Cosynthesis with the Premembrane Protein," Journal of Virology,Mar. 1993, vol. 67 (3), 4 pages.
Kostarelos K., et al., "Steric Stabilization of Phospholipid Vesicles by Block Copolymers Vesicle Flocculation and Osmotic Swelling Caused by Monovalent and Divalent Cations,"Journal of the Chemical Society, Faraday Transactions, Aug. 1998, vol. 94, 10 pages.
Kovacs K., et al., "A Novel Approach for Biohydrogen Production," International Journal of Hydrogen Energy, Sep. 2006, vol. 31 (11), 9 pages.
Kubalek E.W., et al., "Two-dimensional Crystallization of Histidine-tagged, HIV-1 Reverse Transcriptase Promoted by a Novel Nickel-chelating Lipid," Journal of Structural Biology,Sep.-Oct. 1994, vol. 113 (2), 7 pages.
Langworthy, T.A., "Lipids of Thermoplasma," 1982, Methods in Enzymology, vol. 88, 396-406.
Lasic D.D., "Novel Applications of Liposomes," Trends in Biotechnology, Jul. 1998, vol. 16 (7), 15 pages.
Lazar E., et al., "Transforming Growth Factor Alpha: Mutation of Aspartic Acid 47 and Leucine 48 Results in Different Biological Activities," Molecular and Cellular Biology,Mar. 1988, vol. 8 (3), 6 pages.
Liang X., et al., "Mechanical Properties and Stability Measurement of Cholesterol-containing Liposome on Mica by Atomic Force Microscopy, "Journal of Colloid and Interface Science,Oct. 2004, vol. 278 (1), 10 pages.
Lluis M.W., et al., "Protein Engineering Methods Applied to Membrane Protein Targets," Protein Engineering, Design & Selection, Feb. 2013, vol. 26 (2), 10 pages.
Lodish H., et al., "Section 17.5 Insertion of Membrane Proteins into the ER Membrane," Molecular Cell Biology, 4th edition, New York, NY., 2000, 9 pages.
Ludwig W., et al., "ARB: A Software Environment for Sequence Data," Nucleic Acids Research,Feb. 2004, vol. 32 (4), 9 pages.
Ma, K., et al., "Characterization of Hydrogenase II from the Hyperthermophilic Archaeon Pyrococcus furiosus and Assessment of Its Role in Sulfur Reduction," Apr. 2000, Journal of Bacteriology, vol. 182, No. 7, 1864-1871.
Manefield M., et al., "RNA Stable Isotope Probing, a Novel Means of Linking Microbial Community Function to Phylogeny," Applied and Environmental Microbiology, Nov. 2002, vol. 68 (11), 7 pages.
Marshall, G.R., et al., "Conformational effects of chiral a,a-dialkyl amino acids," 1988, Int. J. Peptide Protein Res., 32, 544-555.
Masquelier M., et al., "Low-density Lipoprotein as a Carrier of Antitumoral Drugs: in Vivo Fate of Drug-human Low-density Lipoprotein Complexes in Mice," Cancer Research,Aug. 1986, vol. 46 (8), 6 pages.
Mata-Haro V., et al., "The Vaccine Adjuvant Monophosphoryl Lipid A as a TRIF-Biased Agonist of TLR4," Science, Jun. 2007, vol. 316 (5831), 7 pages.
McGall G.H., et al., "The Efficiency of Light-Directed Synthesis of DNA Arrays on Glass Substrates,"Journal of the American Chemical Society,Jun. 1997, vol. 119 (22), 10 pages.
Metz J., et al., "ACTH, α-MSH, and Control of Cortisol Release: Cloning, Sequencing, and Functional Expression of the Melanocortin-2 and Melanocortin-5 Receptor in Cyprinus Carpio," American Journal of Physiology Regulatory Integrative and Comparative Physiology,May 2005, vol. 289, 13 pages.
Moses S., et al., "Detection of DNA Hybridization on Indium Tin Oxide Surfaces," Sensors and Actuators B,Aug. 2007, vol. 125 (2), 7 pages.
Muscarinic Acetylcholine Receptor, Retrieved from the Internet: URL://web.archive.org/web/20071020193657//https://en.wikipedia.org/wiki/Muscarinic_acetylcholine_receptor, Wikipedia 2007, 6 pages.
Nanodisc Formation. Liao Lab, Department of Cellbiology, Harvard Medical School, retrieved on Aug. 3, 2015, from the Internet: URL:https://liao.hms.harvard.edu/node/34, 2 pages.
Nanodisc. Kobo eBook Library, Retrieved from the Internet: URL: http://www.kobolibrary.com/articles/nanodisc, retrieved on Aug. 4, 2015, 4 pages.

(56) References Cited

OTHER PUBLICATIONS

Newpoint Gas "O2 Removal Services", https://www.newpointgas.com/services/oxygen-o2-removal/, 2017, 4 pages.
Non-Final Office Action for U.S. Appl. No. 14/199,973. Mail Date: May 6, 2015, 34 pages.
Non-Final Office Action for U.S. Appl. No. 14/861,750. Mail Date: Aug. 25, 2017, 23 pages.
Notice of Allowance for U.S. Appl. No. 14/199,973. Mail Date: Dec. 10, 2015, 11 pages.
Notice of Allowance for U.S. Appl. No. 14/861,750, filed Sep. 22, 2015 on behalf of Lawrence Livermore National Security, LLC. Mail Date: Jul. 24, 2018. 15 pages.
Okemoto K., et al., "A Potent Adjuvant Monophosphoryl Lipid a Triggers Various Immune Responses, but Not Secretion of IL-1beta or Activation of Caspase-1," *The Journal of Immunology*, Jan. 2006, vol. 176 (2), 6 pages.
Osada Y., et al., "Polymorphonuclear Leukocyte Activation by a Synthetic Muramyl Dipeptide Analog," *Infection and Immunity*, Dec. 1982, vol. 38 (3), 7 pages.
Ouverney C.C., et al., "Combined Microautoradiography-16S rRNA Probe Technique for Determination of Radioisotope Uptake by Specific Microbial Cell Types in Situ," *Applied and Environmental Microbiology*,Apr. 1999, vol. 65 (4), 8 pages.
Parkin A., et al., "The Difference a Se Makes? Oxygen-tolerant hydrogen production by the [NiFeSe]-hydrogenase from Desulfomicrobium baculatum," Journal of the American Chemical Society, Sep. 2008, vol. 130 (40), 13410-13416. 8 pages.
Persing D.H., et al., "Taking Toll: Lipid a Mimetics as Adjuvants and Immunomodulators," *Trends in Microbiology*,Oct. 2002, vol. 10 (10 Suppl), 6 pages.
Petrakova O., et al., "Noncytopathic Replication of Venezuelan Equine Encephalitis Virus and Eastern Equine Encephalitis Virus Replicons in Mammalian Cells,"*Journal of Virology*,Jun. 2005, vol. 79 (12), 12 pages.
Pettibone D.J., et al., "The Effects of Deleting the Mouse Neurotensin Receptor NTR1 on Central and Peripheral Responses to Neurotensin," *The Journal of Pharmacology and Experimental Therapeutics*,Jan. 2002, vol. 300 (1), 9 pages.
Plumere, et al., "Enzyme-catalyzed O2 removal system for electrochemical analysis under ambient air: application in an amperometric nitrate biosensor (Abstract only)", Anal Chem. Mar. 6, 2012;84(5):2141-2146, Epub Feb. 10, 2012. 2 pages.
Protocols for Preparation of Nanodiscs, Mar. 2008, 7 pages.
Radajewski S., et al., "Identification of Active Methylotroph Populations in an Acidic Forest Soil by Stable Isotope Probing," Microbiology, Aug. 2002, vol. 148 (Pt 8), 12 pages.
Radajewski S., et al., "Stable-Isotope Probing as a Tool in Microbial Ecology," *Nature*, Feb. 2000, vol. 403 (6770), 4 pages.
Ratanabanangkoon P., et al., "Two-Dimensional Streptavidin Crystals on Giant Lipid Bilayer Vesicles," *Langmuir*,2002, vol. 18 (11), 7 pages.
Ren X.R., et al., "Different G Protein-Coupled Receptor Kinases Govern G Protein and Beta-Arrestin-Mediated Signaling of V2 Vasopressin Receptor," *Proceedings of the National Academy of Sciences of the United States of America*,Feb. 1, 2005, vol. 102(5), 6 pages.
Restriction Requirement for U.S. Appl. No. 14/199,973. Mail Date: Dec. 8, 2014, 7 pages.
Restriction Requirement for U.S. Appl. No. 14/861,750. Mail Date: May 19, 2017, 7 pages.
Rüger R., et al., "Generation of Immunoliposomes using Recombinant Single-Chain Fv Fragments Bound to Ni-NTA-Liposomes, "*Journal of Drug Targeting*,Aug. 2005, vol. 13(7), 8 pages.
Schena M., et al., "Quantitative Monitoring of Gene Expression Patterns With a Complementary DNA Microarray," *Science*,Oct. 1995, vol. 270 (5235), 4 pages.
Schnell D.J. et al., "Protein Translocons: Multifunctional Mediators of Protein Translocation across Membranes," *Cell*,Feb. 21, 2003, vol. 112(4), 15 pages.

Simon S.R., et al., "Chemical Modification of Hemoglobins: A Study of Conformation Restraint by Internal Bridging," *Proceedings of the National Academy of Sciences of the United States of America*,Aug. 1966, vol. 56 (2), 8 pages.
Singh-Gasson S., et al., "Maskless Fabrication of Light-directed Oligonucleotide Microarrays Using a Digital Micromirror Array," *Nature Biotechnology*,Oct. 1999, vol. 17 (10), 5 pages.
Soboh B., et al., "A Multisubunit Membrane-Bound [NiFe] Hydrogenase and an NADH-Dependent Fe-only Hydrogenase in the Fermenting Bacterium Thermoanaerobacter tengcongenis," *Microbiology*,2004, vol. 150, 13 pages.
Sun X.L., et al., "Membrane-Mimetic Films of Asymmetric Phosphtidylcholine Lipid Bolaamphiphiles," *Langmuir*,Jan. 2006, vol. 22 (3), 8 pages.
Tercier-Waeber, et al., "Submersible Online Oxygen Removal System Coupled to an in Situ Voltammetric Probe for Trace Element Monitoring in Freshwater (Abstract only)", Environ. Sci. Technol., 2000, 34 (18), pp. 4018-4024, Publication Date (Web): Aug. 11, 2000. 4 pages.
Terpe K., et al., "Overview of Tag Protein Fusions: From Molecular and Biochemical Fundamentals to Commercial Systems," *Applied Microbiology and Biotechnology*,Jan. 2003, vol. 60 (5), 11 pages.
Ueda H., et al., "Induction of Tumor Necrosis Factor-Alpha in Solid Tumor Region by the Orally Administered Synthetic Muramyl Dipeptide Analogue, Romurtide," *International Immunopharmacology*, Jan. 2001, vol. 1 (1), 8 pages.
Uhlik O., et al., "DNA-Based Stable Isotope Probing: A Link between Community Structure and Function," *Science of the Total Environment*,Jun. 2009, vol. 407 (12), 9 pages.
Ulmer J,B., et al., "Vaccine Manufacturing: Challenges and Solutions," *Nature Biotechnology*,Nov. 2006, vol. 24 (11), 7 pages.
Unger R., et al., "The Genetic Algorithm Approach to Protein Structure Prediction,"*Structure and Bonding*,Feb. 2004, vol. 110, 24 pages.
VICI (Valco Instruments Co. Inc.) "Oxygen Removal System", https://www.vici.com/instr/deox.php, pp. 1-2, 2 pages, 2018.
Vignais P.M., et al., "Occurrence, Classification, and Biological Function of Hydrogenases: An Overview," *Chemical Reviews*,Oct. 2007, vol. 107 (10), 67 pages.
Vuorilehto K., et al., "Indirect Electrochemical Reduction of Nicotinamide Coenzymes," *Bioelectrochemistry*, Dec. 2004, vol. 65 (1), 7 pages.
Wacey A.I., et al., "Disentangling the Perturbational Effects of Amino Acid Substitutions in the DNA-binding Domain of p53," *Human Genetics*,Jan. 1999, vol. 104 (1), 8 pages.
Weeratna R.D., et al., "CpG DNA Induces Stronger Immune Responses with Less Toxicity than Other Adjuvants," *Vaccine*,Mar. 2000, vol. 18 (17), 8 pages.
White S.H., et al., "How Translocons Select Transmembrane Helices," Annual Review of Biophysics, 2008, vol. 37, 23-42. 20 pages.
Widman D.G., et al., "Construction and Characterization of a Second-Generation Pseudoinfectious West Nile Virus Vaccine Propagated Using a New Cultivation System," *Vaccine*,May 2008, vol. 26 (22), 10 pages.
Wikipedia, "5-HT Receptor," Wikipedia 2007, Retrieved from the Internet:[URL: http://web.archive.org/web/20071109235348/http://en.wikipedia.org/wiki/5-HT_receptor], 4 pages.
Wikipedia, Adrenergic Receptor, https://web.archive.org/web/20061230132111http//en.wikipedia.org/wiki/Adrenergic_Receptor, 2006, 4 pages.
Written Opinion for Application No. PCT/US2009/044722, Mail Date: Oct. 28, 2010., 8 pages.
Yoon J.C., et al., "Three-Dimensional Graphene Nano-Networks with High Quality and Mass Production Capability via Precursor-Assisted Chemical Vapor Deposition," *Scientific Reports*,2013, vol. 1788, 8 pages.
Zhou, H., et al., Noncovalent Attachment of NAD+ Cofactor onto Carbon Nanotubes for Preparation of Integrated Dehydrogenase-Based Electrochemical Biosensors,: 2010, Langmuir Article, 26(8) 6028-6032.

(56) References Cited

OTHER PUBLICATIONS

Zimmermann S, et al., "Immunostimulatory DNA as Adjuvant: Efficacy of Phosphodiester CPG Oligonucleotides is Enhanced by 3' Sequence Modifications," *Vaccine*, Feb. 2003, vol. 21 (9-10), 6 pages.
Abdulreda M.H., et al., "Atomic Force Microscope Spectroscopy Reveals a Hemifusion Intermediate during Soluble N-Ethylmaleimide-Sensitive Factor-Attachment Protein Receptors-Mediated Membrane Fusion," Biophysical Journal, Jan. 2008, vol. 94 (2), 648-655. 8 pages.
Abdulreda M.H., et al., "Atomic Force Microscope Studies of the Fusion of Floating Lipid Bilayers," *Biophysical Journal*, Jun. 2007, vol. 92 (12), 10 pages.
Advisory Action for U.S. Appl. No. 12/118,396, filed May 9, 2008. Mail Date: Jul. 7, 2015, 8 pages.
Advisory Action for U.S. Appl. No. 12/118,396. Mail Date: Jun. 7, 2012, 5 pages.
Advisory Action for U.S. Appl. No. 12/118,530. Mail Date: Jul. 23, 2015, 13 pages.
Bao P., et al., "High-Sensitivity Detection of DNA Hybridization on Microarrays Using Resonance Light Scattering," *Analytical Chemistry*, Apr. 2002, vol. 74 (8), 6 pages.
Bayburt T.H., et al., "Assembly of Single Bacteriorhodopsin Trimmers in Bilayer Nanodiscs," Archives of Biochemistry and Biophysics, Jun. 2006, vol. 450 (2), 8 pages.
Bayburt T.H., et al., "Reconstitution and Imaging of a Membrane Protein in a Nanometer-size Phospholipid Bilayer," *Journal of Structural Biology*, Sep. 1998, vol. 123 (1), 8 pages.
Boschker H.T.S., et al., "The Contribution of Macrophyte-derived Organic Matter to Microbial Biomass in Salt-marsh Sediments: Stable Carbon Isotope Analysis of Microbial Biomarkers," Limnology and Oceanography, 1999, vol. 44(2), 309-319. 11 pages.
Camarero J.A., et al., "Chemoselective Attachment of Biologically Active Protein to Surfaces by Expressed Protein Ligation and its Application for Protein Chip Fabrication, "*Journal of the American Chemical Society*, Nov. 2004, vol. 126 (45), 2 pages.
Chen J.S., et al., "Amino Acids in SRS1 and SRS6 Are Critical for Furanocoumarin Metabolism by CYP6B1v1, a Cytochrome P450 Monooxygenase," *Insect Molecular Biology*, Apr. 2002, vol. 11 (2), 12 pages.
Claypool et al., An ethanol/ether soluble apoprotein from rat lung surfactant augments liposome uptake by isolated granular pneumocytes. J Clin Invest. Sep. 1984; 74(3): 677-84. (Year: 1984). 8 pages.
Cleveland, T.E. IV, et al., "Small-angle X-ray and neutron scattering demonstrates that cell-free expression produces properly formed disc-shaped nanolipoprotein particles," Protein Science, Dec. 2017, vol. 27, pp. 780-789.
Coleman M., et al., "Asp 46 Can Substitute for Asp 96 as the Schiff Base Proton Donor in Bacteriorhodopsin," *Biochemistry*, Nov. 1995, vol. 34 (47), 8 pages.
Crankshaw C., Nanodisc Technology: A Revolutionary System for Study of Membrane Proteins, *Biofiles*, retrieved on Aug. 4, 2015, Retrieved from the Internet: URL: http://www.sigmaaldrich.com/teclmical-documents/articles!biofiles/nanodisc-technology.html, vol. 8, No. 20, 3 pages.
Cuenca, AG et al., "Emerging implications of nanotechnology on cancer diagnostics and therapeutics."*Cancer*, 2006. vol. 107, No. 3: pp. 459-466. pp. 8.
Definition of "homogeneous", Oxford Dictionaries, retrieved from https://en.oxforddictionaries.com/definition/homogeneous on Apr. 4, 2018, four pages.
Definition of Hydrogenase[online], Nov. 6, 2012 [retrieved on Nov. 6, 2012], Retrieved from Internet: URL: en.wikipedia.org/wiki/Hydrogenase, 4 pages.
Denisov I.G., et al., "Nanodiscs in Membrane Biochemistry and Biophysics", Chemical Reviews, Mar. 2017, vol. 117 (6), 4669-4713. 92 pages.
Ding, Y., et al., "A biomimetic nanovector-mediated targeted cholesterol-conjugated siRNA delivery for tumor gene therapy." *Biomaterials*, 2012. 33(34): p. 8893-8905.

Dong F., et al., "Endothelin-1 Enhances Oxidative Stress, Cell Proliferation and Reduces Apoptosis in Human Umbilical Vein Endothelial Cells: Role of ETB Receptor, NADPH oxidase and caveolin-1" British Journal of Pharmacology, Jun. 2005, vol. 145 (3), 323-333. 11 pages.
Dunn R.J., et al., "Structure-functions Studies on Bacteriorhodopsin," *The Journal of Biological Chemistry*, 1987, vol. 262 (19), 9 pages.
Final Office Action for U.S. Appl. No. 12/118,396. Mail Date: Feb. 4, 2015, 29 pages.
Final Office Action for U.S. Appl. No. 12/118,396. Mail Date: Jan. 18, 2012, 17 pages.
Final Office Action for U.S. Appl. No. 12/118,396. Mail Date: Oct. 11, 2016, 29 pages.
Final Office Action for U.S. Appl. No. 12/118,396. Mail date: Apr. 12, 2018. 25 pages.
Final Office Action for U.S. Appl. No. 12/604,362. Mail Date: Dec. 4, 2012, 8 pages.
Forstner M., et al., "Carboxyl-Terminal Domain of Human ApolipoproteinE: Expression, Purification, and Crystallization," *Protein Expression and Purification*, Nov. 1999, vol. 17 (2), 6 pages.
Forte T.M., et al., "Electron Microscope Study on Reassembly of Plasma High Density Apoprotein with Various Lipids," *Biochimica et Biophysica Acta*, Nov. 1971, vol. 248 (2), 6 pages.
Hauger R.L., et al., "Corticotropin Releasing Factor (CRF) Receptor Signaling in the Central Nervous System: New Molecular Targets," *CNS & Neurological Disorders Drug Targets*, Aug. 2006, vol. 5 (4), 49 pages.
He, W., "Controlling the Diameter, Monodispersity and Solubility of ApoA1 Nanolipoprotein Particles using Telodendrimer Chemistry," (2013) Protein Science 22, 1078-1086.
Howland M.C. et al., "Model Studies of Membrane Disruption by Photogenerated Oxidative Assault." The Journal of Physical Chemistry, 2010. 114(19); p. 6377-6385.
International Preliminary Report on Patentability (Chapter 1) for International Application No. PCT/US2016/048632 filed on Aug. 25, 2016 on behalf of Lawrence Livermore National Laboratory Mail Date: Feb. 27, 2018 11 pages.
International Preliminary Report on Patentability (Chapter 1) for International Application No. PCT/US2017/020827 filed on Mar. 3, 2017 on behalf of Lawrence Livermore National Laboratory Mail Date: Sep. 11, 2018 9 pages.
International Search Report for International Application No. PCT/US2017/020827 filed on Mar. 3, 2017 on behalf of Lawrence Livermore National Laboratory Mail Date: Jun. 20, 2017 4 pages.
International Search Report for International Application No. PCT/US2018/030648 filed on May 2, 2018 on behalf of Synthetic Genomics Mail Date: Aug. 30, 2018 4 pages.
Jayaraman S., et al., "Structural Basis for Thermal Stability of Human Low-density Lipoprotein," *Biochemistry*, Mar. 2005, vol. 44 (10), 7 pages.
Kalmbach R., et al., "Functional Cell-free Synthesis of a Seven Helix Membrane. Protein: In Situ Insertion of Bacteriorhodopsin in Liposomes," *Journal of Molecular Biology*, Aug. 2007, vol. 371 (3), 10 pages.
Kim Y.P., et al., "Gold Nanoparticle-enhanced Secondary Ion Mass Spectrometry Imaging of Peptides on Self-assembled Monolayers," *Analytical Chemistry*, Mar. 2006, vol. 78(6), 8 pages.
Klammt C., et al., "Cell-free Expression as an Emerging Technique for the Large Scale Production of Integral Membrane Protein," *The FEBS Journal*, Sep. 2006, vol. 273 (18), 13 pages.
Klammt C., et al., "Evaluation of Detergents for the Soluble Expression of Alpha-helical and Beta-barrel-type Integral Membrane Proteins by a Preparative Scale Individual Cell-free Expression System," The FEBS Journal, Dec. 2005, vol. 272 (23), 15 pages.
Klammt C., et al., "High Level Cell-free Expression and Specific Labeling of Integral Membrane Proteins," *European Journal of Biochemistry*, Feb. 2004, vol. 271 (3), 13 pages.
Kreshech G.C. "Surfactants in Water—A Comprehensive Treatise." 1975: Plenum, New York.

(56) References Cited

OTHER PUBLICATIONS

Lee J., et al., "Ab Initio Protein Structure Prediction: in From Protein Structure to Function with Bioinformatics," *Springer Science + Business Media B.V.*, 2009, 23 pages.

Loll, PJ, "Membrane protein structural biology: the high throughput challenge", J. of Structural Biology, 142:144-153; 2003.

Lu B., et al., "Conformational Reorganization of the Four-helix Bundle of Human Apolipoprotein E in Binding to Phospholipid," The Journal of Biological Chemistry, Jul. 2000, vol. 275 (27), 7 pages.

Ly, S., et al., (Jan. 2014) "Quantifying interactions of a membrane protein embedded in lipid nanodisc using fluorescence correlation spectroscopy," Biophysical Journal. 106: L05-L08.

Ly, S., et al., "Quantifying membrane protein interactions in solution using fluorescence correlation spectroscopy," Biophysical Journal, (Aug. 15, 2013), LLNL-JRNL-642412. Lawrence Livermore National Laboratory. 11 pages.

Madani Sy, et al., "A concise review of carbon nanotube's toxicology." Nano Rev., 2013. vol. 4, Issue 1.

Morrow J.A., et al., "Functional Characterization of Apolipoprotein E Isoforms Overexpressed in *Escherichia coli,"* Protein Expression and Purification, 1999, vol. 16 (2), 7 pages.

Non-Final Office Action for U.S. Appl. No. 12/118,396. Mail Date: Aug. 30, 2011, 18 pages.

Non-Final Office Action for U.S. Appl. No. 12/118,396. Mail Date: Jan. 8, 2016, 32 pages.

Non-Final Office Action for U.S. Appl. No. 12/118,396. Mail Date: Jul. 22, 2014, 28 pages.

Non-Final Office Action for U.S. Appl. No. 12/118,396. Mail Date: Sep. 6, 2017, 33 pages.

Non-Final Office Action for U.S. Appl. No. 12/604,362. Mail Date: May 7, 2012, 12 pages.

Notice of Allowance for U.S. Appl. No. 12/604,362. Mail Date: Jul. 30, 2014, 13 pages.

Okazaki T. et al., "Polymerized lipid bilayers on a solid substrate: Morphologies and obstruction of lateral diffusion." Langmuir, 2009. 25(1): p. 345-351.

Rao R.S., et al., "Comparison of Multiplexed Techniques for Detection of Bacterial and Viral Proteins," *Journal of Proteome Research*, Jul.-Aug. 2004, vol. 3(4), 7 pages.

Restriction Requirement for U.S. Appl. No. 12/118,396. Mail Date: Mar. 4, 2011, 14 pages.

Restriction Requirement for U.S. Appl. No. 12/604,362. Mail Date: Jan. 11, 2012, 8 pages.

Restriction Requirement for U.S. Appl. No. 16/082,924, filed Sep. 6, 2018 on behalf of Lawrence Livermore National Laboratory Mail Date: Oct. 24, 2019 9 pages.

Rusiñol A.E., et al., "In Vitro Reconstitution of Assembly of Apolipoprotein B48-Containing Lipoproteins," *The Journal of Biological Chemistry*, Mar. 21, 1997, vol. 272(12), 7 pages.

Saito H. et al., "Contributions of domain structure and lipid interaction to the functionality of exchangeable human apolipoproteins" Elsevier, 2004. pp. 350-380.

Segelke B.W., et al., "Laboratory Scale Structural Genomics," *Journal of Structural and Functional Genomics*, 2004, vol. 5(1-2), 11 pages.

Sonar S., et al., "A Redirected Proton Pathway in the Bacteriorhodopsin Mutan Tyr-57—Asp. Evidence for Proton Translocation Without Schiff Base Deprotonation," *The Journal of Biological Chemistry*, Nov. 1994, vol. 269 (46), 8 pages.

Sonar S., et al., "Cell-Free Synthesis, Functional Refolding and Spectroscopic Characterization of Bacteriorhodopsin, an Integral Membrane Protein," *Biochemistry*, Dec. 1993, vol. 32 (50), 5 pages.

Stryer., "Lipid Vesicles (Liposomes) and Planar Bilayer Membranes are Valuable Model Systems," Biochemistry, 1995, 1 page.

Swaney J.B., "Properties of Lipid-apolipoprotein Association Products. Complexes of Human Apo AI and Binary Phospholipid Mixtures," *Journal of Biological Chemistry*, Sep. 1980, vol. 255, vol. 18, pp. 8798-8803.

Vickers, K.C., et al., "MicroRNAs are transported in plasma and delivered to recipient cells by high-density lipoproteins." Nat Cell Biol, 2011. 13(4): p. 423-433. 20 pages.

Walter P., et al., "Preparation of Microsomal Membranes for Cotranslational Protein Translocation," *Methods in Enzymology*, 1983, vol. 96, 10 pages.

Wang J., et al., "Comparison of the Dynamics of the Primary Events of Bacteriorhodopsin in Its Trimeric and Monomeric States," *Biophysical Journal*, Sep. 2002, vol. 83 (3), 10 pages.

Wang, S. et al., "The unsolved mystery of apoA-1 recycling in adipocyte." Lipids Health Dis, 2016. 15: p. 35, 8 pages.

Wetterau J.R., et al., "Effect of Dipalmitoylphosphatidylcholine Vesicle Curvature on the Reaction With Human Apolipoprotein A-I," *The Journal of Biological Chemistry*, Sep. 1982, vol. 257 (18), 7 pages.

Wientzek M., et al., "Binding of Insect Apolipophorin III to Dimyristoylphosphatidylcholine Vesicles. Evidence for a Conformational Change," *Journal of Biological Chemistry*, Feb. 1994, vol. 269 (6), 8 pages.

Written Opinion for International Application No. PCT/US2018/030648 filed on May 2, 2018 on behalf of Synthetic Genomics Mail Date: Aug. 30, 2018 6 pages.

Written Opinion for International Application No. PCT/US2017/020827 filed on Mar. 3, 2017 on behalf of Lawrence Livermore National Laboratory Mail Date: Jun. 20, 2017 8 pages.

Wuu J.J., et al., "High Yield Cell-Free Production of Integral Membrane Proteins without Refolding or Detergents," *Biochimica et Biophysica Acta*, May 2008, vol. 1778 (5), 14 pages.

Yang T. et al., "Identification and cellular localization of human PFTAIRE1" Gene, 2001. 267(2): p. 165-172.

Yuan, Y., et al., "Delivery of hydrophilic drug doxorubicin hydrochloride-targeted liver using apoAI as carrier." *J Drug Target*, 2013. 21(4): p. 367-374.

Zidovska A. et al., "Block Liposome and Nanotube Formation is a General Phenomenon of Two-Component Membranes Containing Multivalent Lipids", Jan. 1, 2011, Soft Matter, vol. 7, No. 18, pp. 8363-8369.

Amar M. et al., "A Novel Apolipoprotein C-II Mimetic Peptide That Activates Lipoprotein Lipase and Decreases Serum Triglycerides in Apolipoprotein E-Knockout Mice" *The Journal of Pharmacology And Experimental Therapeutics*, pp. 227-235, Feb. 2015.

Cysteine—Wikipedia, the free encyclopedia, Sep. 20, 2015. https://web.archive.org/web/20150920101331/https://en.wikipedia.org/wiki/Cysteine. 8 pages.

Donia M. et al., "Small Molecules from the Human Microbiota" *Science*, vol. 349, Jul. 24, 2015, pp. 1-25.

Final Office Action for U.S. Appl. No. 16/082,924, filed Sep. 6, 2018 on behalf of Lawrence Livermore National Security, LLC. Mail Date: May 21, 2020. 50 Pages.

He Y. et al., "Apolipoprotein A1 Forms 5/5 and 5/4 Antiparallel Dimers in Human High-density Lipoprotein" *Molecular & Cellular Proteomics*, pp. 854-864, Jul. 2019.

Li J. et al., "Synthesis of many different types of organic small molecules using one automated process"*Science Mag*, vol. 347 is. 6227, Mar. 13, 2015, pp. 1221-1226.

Notice of Allowance for U.S. Appl. No. 15/499,855, filed Apr. 27, 2017 on behalf of Lawrence Livermore National Security, LLC. Mail date: Jun. 25, 2020. 9 pages.

Small molecule—Wikipedia, the free encyclopedia, May 12, 2015. https://web.archive.org/web/20150512235530/https://en.wikipedia.org/wiki/Small_molecule. 4 pages.

Alpha Helix—Wikipedia, the free encyclopedia, Nov. 7, 2014, 15 pages. https://web.archive.org/web/20141107095336/https://en.wikipedia.org/wiki/Alpha_helix.

Final Office Action for U.S. Appl. No. 15/744,754, filed Jan. 12, 2018, on behalf of Lawrence Livermore National Laboratory. Mail Date: Oct. 14, 2020. 21 Pages.

Gilmore S. F. et al., "Lipid composition dictates serum stability of reconstituted high-density lipoproteins: implications for in vivo applications" Royal Society of Chemistry, Nanoscale, Mar. 2018, 10, 7420-7430. 12 pages.

(56) References Cited

OTHER PUBLICATIONS

Gilmore S. F. et al., "Lipid cross-linking of nanolipoprotein particles substantially enhances serum stability and cellular uptake" Applied Materials and Interfaces, Jul. 2016, 8, 20549-20557. 9 pages.
Kuai R. et al., "Designer vaccine nanodiscs for personalized cancer immunotherapy"*Nature Materials*,Dec. 2016 10 pages.
Kuai R. et al., "Designer vaccine nanodiscs for personalized cancer immunotherapy (Supplementary Information)" *Nature Materials*,Dec. 2016 18 pages.
Liposome—Wikipedia, the free encyclopedia. Dated: Jul. 5, 2016, 7 pages, https://en.wikipedia.org/wiki/Liposome.
Micelle—Wikipedia, the free encyclopedia, Dated: Dec. 1, 2020, 7 pages https://en.wikipedia.org/wiki/Micelle.
Nanodisc—Wikipedia, the free encyclopedia. Dated: Jul. 5, 2016, 3 pages, https://en.wikipedia.org/wiki/Nanodisc.
Nanodisc Inc. Company Profile—ZoomInfo.com, Dated: May 25, 2015, 2 pages, https://www.zoominfo.com/c/nanodisc/65701329.
Notice of Allowance for U.S. Appl. No. 15/499,855, filed Apr. 27, 2017 on behalf of Lawrence Livermore National Laboratory. Mail Date: Oct. 15, 2020,. 9 pages.
Hafner, et al., "Development status and future prospects for a vaccine against Chlamydia trachomatis infection," Vaccine, 32, (2014), pp. 1563-1571. Published online: Aug. 22, 2013. 9 Pages.
Non-Final Office Action for U.S. Appl. No. 16/609,420, filed Oct. 29, 2019 on behalf of Lawrence Livermore National Laboratory. Mail Date: Dec. 28, 2020. 53 Pages.
Notice of Allowance for U.S. Appl. No. 15/499,855, filed Apr. 27, 2017 on behalf of Lawrence Livermore National Security LLC Mail Date: Jan. 25, 2021 9 pages.
Plotkin, et al., Vaccines, WB Saunders Company, p. 571. Year: 1988. 2 Pages.
Restriction Requirement for U.S. Appl. No. 16/159,189, filed Oct. 12, 2018 on behalf of Lawrence Livermore National Security, LLC. Mail Date: Jan. 29, 2021, 6 Pages.
Advisory Action for U.S. Appl. No. 15/744,754, filed Jan. 12, 2018 on behalf of Lawrence Livermore National Security, LLC Mail Date: Mar. 16, 2021 13 pages.
Bezrukov S. M. "Functional consequences of lipid packing stress" Current Opinion in Colloid & Interface Science 5, Jan. 2000, pp. 237-243.
Bloedon L.T. et al., "Safety, pharmacokinetics, and pharmacodynamics of oral apoA-I mimetic peptide D-4F in high-risk cardiovascular patients" Journal of Lipid Research, vol. 49, Mar. 2008, pp. 1344-1352.
Borhani D. W. et al., "Crystal structure of truncated human apolipoprotein A-I suggests a lipid-bound conformation" Proc. Natl. Acad. Sci. USA, vol. 94, Nov. 1997, pp. 12291-12296.
Denisov I. G. "Thermotropic Phase Transition in Soluble Nanoscale Lipid Bilayers" *J Phys Chem B.*, Aug. 18, 2005, 109(32), 23 pages.
"Drug" Wikipedia, the free encyclopedia. Downloaded through the Wayback Machine for Dec. 8, 2011. 5 pages.
Elson E. L. "Fluorescence Correlation Spectroscopy: Past, Present, Future" Biophysical Journal, vol. 101, Dec. 2011, pp. 2855-2870.
Extended European Search Report for EP Application No. 17763807.9 filed on Oct. 4, 2018 on behalf of Lawrence Livermore National Security LLC Mail Date: Oct. 30, 2019 8 pages.
Klevens H. B. "Structure and Aggregation in Dilute Solutions of Surface Active Agents" The Journal of the American Oil Chemists Society, Feb. 1953, 7 pages.
Leman L.J. et al., "Molecules that Mimic Apolipoprotein A-I: Potential Agents for Treating Atherosclerosis" J Med Chem, 57(6), Mar. 2014, 2169-2196. 56 pages.
Li L. et al., "Double Belt Structure of Discoidal High Density Lipoproteins: Molecular Basis for Size Heterogeneity" J. Mol. Biol, vol. 343, 2004, pp. 1293-1311.
Liposome—Wikipedia, the free encyclopedia. Downloaded through The Wayback Machine with a date of Dec. 31, 2015, 7 pages.
Marsh D. "Equation of State for Phospholipid Self-Assembly" *Biophysical Journal*, vol. 110, Jan. 2016, pp. 188-196.
Martinez D. et al., "Lipid Internal Dynamics Probed in Nanodiscs" ChemPhysChem, Jan. 2017, 18, pp. 2651-2657.
Mendez A.J. "Synthetic Amphipathic Helical Peptides That Mimic Apolipoprotein A-I in Clearing Cellular Cholesterol"J Clin. Invest, vol. 94, Oct. 1994, pp. 1698-1705.
Non-Final Office Action for U.S. Appl. No. 16/082,924, filed Sep. 6, 2018 on behalf of Lawrence Livermore National Security, LLC Mail Date: May 25, 2021 25 pages.
Non-Final Office Action for U.S. Appl. No. 16/159,189, filed Oct. 12, 2018 on behalf of Lawrence Livermore National Security, LLC. Mail Date: Jun. 24, 2021. 32 Pages.
Notice of Allowance for U.S. Appl. No. 15/499,855, filed Apr. 27, 2017 on behalf of Lawrence Livermore National Security, LLC.. Mail date: May 14, 2021.10 Pages.
Notice of Allowance for U.S. Appl. No. 15/744,754, filed Jan. 12, 2018, on behalf of Lawrence Livermore National Laboratory. Mail Date: Jul. 14, 2021. 11 pages.
Notice of Allowance for U.S. Appl. No. 16/609,420, filed Oct. 29, 2019 on behalf of Lawrence Livermore National Laboratory. Mail Date: Jul. 28, 2021. 7 Pages.
Notice of Allowance for U.S. Appl. No. 16/609,420, filed Oct. 29, 2019 on behalf of Lawrence Livermore National Laboratory. Mail Date: May 6, 2021. 10 Pages.
Notice of Allowance for U.S. Appl. No. 16/609,420, filed Oct. 29, 2019 on behalf of Lawrence Livermore National Laboratory. Mail Date: Nov. 10, 2021. 7 Pages.
Pollock, N.L. et al., "Structure and function of membrane proteins encapsulated in a polymer-bound lipid bilayer", Biochimica et Biophysica Acta (BBA)—Biomembranes (Apr. 2018), vol. 1860, Issue 4, pp. 809-817, 9 pages; Internet: dx.doi.org/10.1016/j.bbamem.2017.08.012.
Popot J.L. "Alternatives to Detergents for Handling Membrane Proteins in Aqueous Solutions" Membrane Proteins in Aqueous Solutions, Jun. 2018, pp. 97-149. 134 pages.
Popovic K. et al., "Structure of saposin A lipoprotein discs" PNAS, vol. 109 No. 8, Feb. 2012, pp. 2908-2912.
Schachter T. et al., "Confinement in Nanodiscs Anisotropically Modifies Lipid Bilayer Elastic Properties" J. Phys. Chem. B, Jul. 2020, vol. 124, pp. 7166-7175.
Schuler M. et al., "Nanodiscs as a new tool to examine lipid-protein interactions" *Methods Mol Biol.*, 2013; 974, pp. 415-433.
Segrest J. P. "Amphipathic Helix Motif: Classes and Properties" Proteins: Structure, Function, and Genetics, vol. 8, 1990, pp. 103-117.
Segrest J.P. et al., "Pathogenesis of atherosclerosis" *Current Opinion in Cardiology*, vol. 9, 1994, pp. 404-410.
Shelby M. et al., "Cell-Free Co-Translational Approaches for Producing Mammalian Receptors: Expanding the Cell-Free Expression Toolbox Using Nanolipoproteins" *Frontiers in Pharmacology*, vol. 10 No. 744, Jul. 2019, pp. 1-12.
Spuhler P. et al., "Binding of Apolipoprotein A-I Model Peptides to Lipid Bilayers" The Journal of Biological Chemistry, vol. 269 No. 39, Sep. 1994, pp. 23904-23910.
Stepien P. et al., "Comparative EPR studies on lipid bilayer properties in nanodiscs and liposomes" *Biochimica et Biophysica Acta*, 1848, Oct. 2014, pp. 60-66.
Swainsbury D.J.K. et al., "The effectiveness of styrene-maleic acid (SMA) copolymers for solubilisation of integral membrane proteins from SMA-accessible and SMA-resistant membranes" BBA-Biomembranes, 1859, Jul. 2017, pp. 2133-2143.
Tanaka, M. et al. "Preparation and Characterization of Reconstituted Lipid-Synthetic Polymer Discoidal Particles" Langmuir, (Sep. 2015),vol. 31, Issue 46, 12719-12726. 8 pages. Internet: doi.10.1021/acs.langmuir.5b03438.
Troutt J.S. et al., "An apolipoprotein A-I mimetic dose-dependently increases the formation of preB1 HDL in human plasma" Journal of Lipid Research, vol. 49, Mar. 2008, pp. 581-587.
Watson C.E. et al., "Treatment of patients with cardiovascular disease with L-4F, an apo-A1 mimetic, did not improve select biomarkers of HDL function" Journal of Lipid Research, vol. 52, Feb. 2011, pp. 361-373.

(56) References Cited

OTHER PUBLICATIONS

Wool G.D. "Apolipoprotein A-I mimetic peptide helix number and helix linker influence potentially anti-atherogenic properties" Journal of Lipid Research, vol. 49, 2008, pp. 1268-1283.
Zhao Y. et al., "Self-Assembling Cyclic D,L-a-Peptides as Modulators of Plasma HDL Function. A Supramolecular Approach toward Antiatherosclerotic Agents" ACS Central Science, vol. 3, Jun. 2017, pp. 639-646.
Final Office Action for U.S. Appl. No. 16/082,924, filed Sep. 6, 2018 on behalf of Lawrence Livermore National Security, LLC Mail Date: Jan. 25, 2022 21 pages.
Frankel D. et al., "Photoinduced destabilization of bilayer vesicles" J. Am. Chem. Soc. vol. 111 No. 26, 1989, pp. 9262-9263.
Lamparski H. et al., "Photoinduced destabilization of liposomes" Biochemistry, vol. 31 No.3, 1992, pp. 685-694.
Mueller A. et al., "Supramolecular materials via polymerization of mesophases of hydrated amphiphiles" Chem. Rev. 102(3), 2002, pp. 727-757.
Non-Final Office Action for U.S. Appl. No. 15/969,311, filed May 2, 2018, on behalf of Synthetic Genomics, Inc. Mail Date: Jun. 10, 2022. 55 Pages.
Notice of Allowability for U.S. Appl. No. 16/159,189, filed Oct. 12, 2018, on behalf of Lawrence Livermore National Security, LLC. Mail Date: Dec. 21, 2021. 4 Pages.
Notice of Allowance for U.S. Appl. No. 15/744,754, filed Jan. 12, 2018 on behalf of Lawrence Livermore National Security, LLC. Mail Date: Nov. 22, 2021 11 pages.
Notice of Allowance for U.S. Appl. No. 16/159,189, filed Oct. 12, 2018 on behalf of Lawrence Livermore National Security, LLC. Mail Date: Dec. 9, 2021. 10 Pages.
Restriction Requirement for U.S. Appl. No. 15/969,311, filed May 2, 2018 on behalf of Lawrence Livermore National Security, LLC. Mail Date: Dec. 20, 2021. 9 Pages.
Tyminski P. N. et al., "Rhodopsin in polymerized bilayer membranes" J. Am. Chem. Soc. vol. 107 No. 25, 1985, pp. 7769-7770.
Tyminski P.N. et al., "Reconstitution of Rhodopsin and the cGMP cascade in polymerized bilayer membranes" Biochemistry, vol. 27 No. 8, 1988, pp. 2696-2705.
European Examination Report for EP Application No. 17763807.9 filed on Mar. 3, 2017 on behalf of Lawrence Livermore National Security, LLC Mail Date: Aug. 17, 2022 6 pages.
Geall A. J. et al., "Nonviral delivery of self-amplifying RNA vaccines" PNAS, vol. 109 No. 36, Sep. 2012, pp. 14604-14609.
Houseley J. et al., "The Many Pathways of RNA Degradation" Cell, vol. 136, Feb. 2009, pp. 763-776.
Kauffman K. J. et al., "Materials for non-viral intracellular delivery of messenger RNA therapeutics" Journal of Controlled Release, vol. 240, 2016, pp. 227-234.
Midoux P. et al. "Lipid-based mRNA vaccine delivery systems" Expert Rev. Vaccines, 2014, pp. 1-14.
Pardi N. et al., "Expression kinetics of nucleoside-modified mRNA delivered in lipid nanoparticles to mice by various routes." J. Control Release, Nov. 2015, pp. 1-18.
Pardi N. et al., "mRNA vaccines—a new era in vaccinology" Nature Reviews, vol. 17, Apr. 2018, pp. 261-279.
Ramachandran S. et al., "Delivery Strategies for mRNA Vaccines" Pharmaceutical Medicine, vol. 36, Jan. 2022, pp. 11-20.
Reichmuth A. M. et al., "mRNA vaccine delivery using lipid nanoparticles" Ther. Deliv., vol. 7 No. 5, Apr. 2016, pp. 319-334.
Schmidt S. T. et al., "Liposome-Based Adjuvants for Subunit Vaccines: Formulation Strategies for Subunit Antigens and Immunostimulators" Pharmaceutics, Mar. 2016, vol. 8 No. 7, pp. 1-22.
Weissman D. et al., "mRNA transcript therapy" Expert Rev. Vaccines, 2014, pp. 1-17.
Non-Final Office Action for U.S. Appl. No. 15/969,311, filed May 2, 2018, on behalf of Lawrence Livermore National Security, LLC. Mail Date: Jun. 10, 2022. 55 Pages.
Final Office Action for U.S. Appl. No. 15/969,311, filed May 2, 2018 on behalf of Lawrence Livermore National Security, LLC, Mail Date: Nov. 18, 2022, 9 pages.
Non-Final Office Action for U.S. Appl. No. 17/308,921, filed May 5, 2021 in the name of Lawrence Livermore National Security, LLC. Mailed on Nov. 10, 2022. 12 pages.

\* cited by examiner

STABLE NANOLIPOPROTEIN PARTICLES AND RELATED COMPOSITIONS METHODS AND SYSTEMS

CROSS REFERENCE TO RELATED APPLICATION

The present application is the U.S. National Stage of International Patent Application No. PCT/US2016/048632 filed on Aug. 25, 2016 which claims priority of U.S. Provisional Application No. 62/209,784, entitled "Stable Nanolipoprotein Particles and Related Compositions Methods And Systems" filed on Aug. 25, 2015, the entire disclosure of which are incorporated herein by reference.

STATEMENT OF GOVERNMENT GRANT

The United States Government has rights in this invention pursuant to Contract No. DE-AC52-07NA27344 between the United States Department of Energy and Lawrence Livermore National Security, LLC, for the operation of Lawrence Livermore National Laboratory.

FIELD

The present disclosure relates to nanolipoprotein particles (NLPs) and, in particular, to stable nanolipoprotein particles and related compositions methods and systems.

BACKGROUND

Nanolipoprotein particles are nanometer-sized particles usually comprised of an amphipathic lipid bilayer and an apolipoprotein. NLPs have been used for various biotechnology applications, such as membrane protein stabilization/solubilization, drug delivery, and in particular vaccine delivery, and diagnostic imaging.

In some instances, NLPs can self-assemble under appropriate conditions into nano-scale amphipathic apolipoprotein-stabilized lipid bilayer particles possibly comprising additional molecules, such as one or more integral membrane proteins or other proteins and molecules attached to the amphipathic component of the NLP. The self-assembled particles are typically formed by an apolipoprotein encircling a nanometer scale lipid bilayer defining a nanolipoprotein particle.

Despite the advancement of this technology, providing NLPs including desired functionalities and/or with a desired stability can be challenging.

SUMMARY

Provided herein, are nanolipoprotein particles, and related compositions, methods and systems, which comprise one or more membrane forming lipids, one or more polymerized and/or polymerizable lipids and a scaffold protein. In several embodiments, nanolipoprotein particles herein described can show an increased stability in various media, including biological media, compared to certain nanolipoprotein particles of the art.

According to a first aspect, a nanolipoprotein particle is described. The nanolipoprotein particle comprises, a membrane forming lipid, a polymerized lipid and a scaffold protein, the membrane forming lipid and the polymerized lipid arranged in a membrane lipid bilayer stabilized by the scaffold protein and by the polymerized lipids.

According to a second aspect, a nanolipoprotein particle is described. The nanolipoprotein particle comprises, a cross-linked membrane lipid bilayer confined in a discoidal configuration by a scaffold protein, the cross-linked membrane lipid bilayer comprising one or more polymerized lipids and one or more membrane forming lipids.

According to a third aspect, a nanolipoprotein particle is described. The nanolipoprotein particle comprises: a membrane-forming lipid, a polymerizable lipid, and a scaffold protein. In the nanolipoprotein particle, the membrane forming lipid and the polymerizable lipid are arranged in a membrane lipid bilayer stabilized by the scaffold protein. In some embodiments polymerization of the polymerizable lipid within the membrane lipid bilayer provides nanolipoprotein particles comprising a cross-linked membrane lipid bilayer.

According to a fourth aspect, a method and system to provide a nanolipoprotein particle, are described. The method comprises contacting a membrane forming lipid and one or more polymerizable lipids with a scaffold protein to provide a discoidal membrane forming lipid bilayer comprising the membrane forming lipid and the one or more polymerizable stabilized by the scaffold protein. The method can further comprise crosslinking the one or more polymerizable lipids within the membrane lipid bilayer thus providing a nanolipoprotein particle with a cross-linked membrane lipid bilayer.

The system comprises one or more membrane-forming lipids, one or more polymerizable lipids, and a scaffold protein. In the system upon assembly the one or more membrane forming lipids and the scaffold protein provide the nanolipoprotein particle in which the one or more polymerizable lipids are comprised within a membrane lipid bilayer stabilized by the scaffold protein. The system can further comprise a crosslinking agent capable to cross-link the one or more polymerizable lipids within the membrane lipid bilayer to provide a nanolipoprotein particle with a cross-linked membrane lipid bilayer.

According to a fifth aspect, a method and system to stabilize a nanolipoprotein particle is described. The method comprises crosslinking a polymerizable lipid within a membrane lipid bilayer stabilized by a scaffold protein in a discoidal configuration with the membrane lipid bilayer further comprising membrane forming lipids, to provide a stabilized nanolipoprotein particle.

The system comprises one or more nanolipoprotein particles comprising one or more polymerizable lipids and one or more membrane forming lipids within a membrane lipid bilayer stabilized by a scaffold protein, and one or more crosslinking agent. In the system crosslinking of the one or more polymerizable lipids by the one or more crosslinking agent within the membrane lipid bilayer provides the stabilized nanolipoprotein particle.

According to a sixth aspect, any one of the nanolipoprotein particle herein described further comprises an active target molecule, such as an immunogen, a drug, a contrast agent or another molecule of interest, presented on the nanolipoprotein particle.

According to additional aspects, compositions, (and in particular pharmaceutical compositions and more particularly vaccines), methods and systems, comprising, forming and using the nanolipoprotein particles herein described are also provided in the present disclosure. Methods and systems to perform an assay on a target molecule and/or to deliver a target molecule based on the nanolipoprotein particles of the present disclosure, are also described.

Cross-linked nanolipoprotein particles herein described show an increased resistance to chemical change or to physical disintegration compared to non-cross-linked nanolipoprotein particles comprising the same components thus providing nanolipoproteins with increased stability with respect to a same non-cross-linked particle.

In several embodiments cross-linked nanoparticles herein described show a half-life of between from about 10 to about 100 hours in 100% blood serum.

In several embodiments cross-linked nanoparticles herein described show over a 100 fold increase in their half-life in 100% blood serum compared to the half-life in 100% blood serum of non-cross-linked nanoparticles comprising the same components.

Nanolipoprotein particles and related compositions methods and systems herein described, allow in several embodiments sequestering in the nanolipoprotein structure up to 25% by mass of an active target molecule such as drug or imaging agent or radiotherapy or photodynamic therapy agent.

Nanolipoprotein particles and related compositions methods and systems herein described allow in several embodiments to drastically increase the Area Under the Curve (AUC) of said particles upon IV administration to an individual 5 to 50 fold higher compared to drugs that are not nanoformulated.

In several embodiments, cross-linked nanoparticles herein described show an increased stability during disruptive or destructive measurements or experiments, such as small-angle X-ray (SAXS) measurements compared to non-cross-linked nanolipoprotein particles comprising the same components, thus providing nanolipoproteins with increased stability with respect to a same non-cross-linked particle.

Nanolipoprotein particles and related compositions methods and systems herein described allow in several embodiments to perform measurements with less variability between measurements compared to non-cross-linked nanolipoprotein particles comprising the same components.

Nanolipoprotein particles and related methods and systems herein described can be used in connection with various applications wherein stability of the NLP is desired. For example, nanolipoprotein particles herein described and related compositions methods and systems can be used as a vehicle for delivery of compounds such as therapeutics to a specific target destination, as a platform for immunostimulating agents, vaccine development and use, and/or to contain cell-targeting moieties. Additional exemplary applications include uses of nanolipoprotein particles in several fields including basic biology research, applied biology, bio-engineering, bio-energy, medical research, medical diagnostics, therapeutics, bio-fuels, and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and example sections, serve to explain the principles and implementations of the disclosure. Exemplary embodiments of the present disclosure will become more fully understood from the detailed description and the accompanying drawings, wherein:

FIG. 2A, shows lipids possessing one unsaturation per acyl chain. FIG. 2B shows lipids of a fixed length, but a varying number of unsaturations and lipid mixtures. ( $p<0.01$, ** $p<0.0001$).

FIG. 3A, lipids possessing one unsaturation per acyl chain. FIG. 3B, shows lipids of a fixed length, but a varying number of unsaturations and lipid mixtures. (**** $p<0.0001$).

FIG. 4 Panel A shows representative aSEC traces showing NLP peaks of DOPC NLPs and DOPC-DiynePC NLPs with and without UV exposure. All NLPs displayed similar retention times indicating that the DiynePC lipid did not affect NLP size or structure. FIG. 4 Panel B shows average particle size of these NLP formulations obtained through dynamic light scattering. FIG. 4 Panel C shows preliminary stability data of these formulations in sera for 10 minutes, expressed as fraction of NLP peak remaining. (* $p<0.05$).

FIG. 5A shows the fraction of NLP remaining after 10 minutes in FBS at 37° C. for different mixtures of DiynePC and DOPC.

FIG. 5B, shows a plot showing the fraction of NLP population remaining after 10 minutes in FBS at 37° C. as a function of UV-C exposure with 20% DiynePC, 80% DOPC. FIG. 5C, shows the estimated number of DiynePC monomers remaining in an individual NLP particle as a function of UV exposure time, as obtained through analysis of reverse phase HPLC and known lipid:protein ratios.

FIG. 6A shows the percentage of the DiynePC and DOPC NLP populations remaining at the times indicated after incubation in serum at 37° C. FIGS. 6B and 6C show comparisons between the raw SEC traces of the DOPC NLPs at zero and 10 minutes in serum, and the raw SEC traces of the DiynePC NLPs at zero and eight hours, respectively.

FIG. 9A, shows diagrams illustrating representative aSEC traces of collected serum from mice injected with fluorescent DOPC NLP solution (gray line) and cross-linked NLP solution (black line) showing signal in the NLP region, with background fluorescence subtracted out. FIG. 9B, shows DOPC NLP and cross-linked NLP concentration in serum based on standard curves for the NLP solutions in serum. (** $p<0.01$).

DETAILED DESCRIPTION

Figure 1:
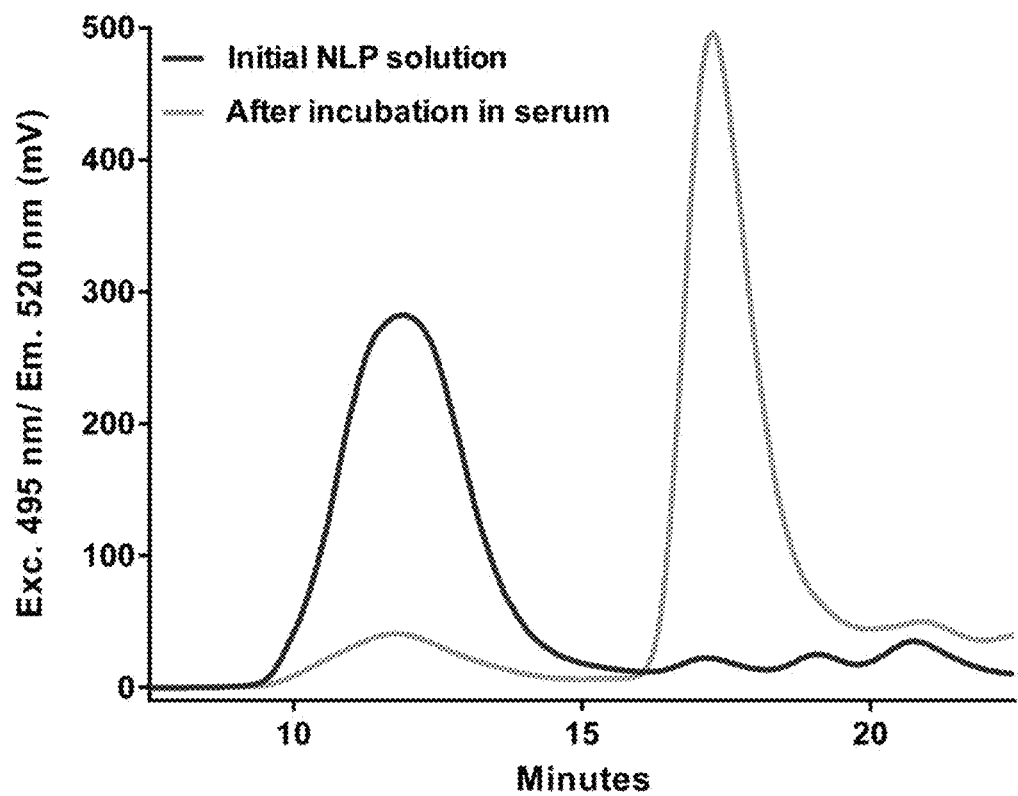
FIG. 1 shows a chart illustrating representative SEC traces of fluorescent NLPs showing degradation over time in sera solutions. Intact NLPs were injected onto the SEC column and eluted with a retention time of ~12 min (black line), which corresponds to the size of an intact particle. In addition, there was no peak corresponding to scaffold protein not associated with the NLP (retention time ~17.5 min) NLPs that had been subjected to high temperature treatment for 45 minutes in 100% sera were also injected on the SEC column (gray line). In this trace, only a small peak was observed at the intact NLP retention time (~12 min) and a large peak corresponding to free scaffold protein not attached to the NLP was observed at a retention time of ~17.5 min, clearly indicating that a majority of the NLP had disassembled.

Provided herein are nanolipoprotein particles and related compositions, methods and systems.

The term "nanolipoprotein particle" 'nanodisc" "rHDL" or "NLP" as used herein indicates a supramolecular complex formed by a membrane forming lipid arranged in a membrane lipid bilayer stabilized by a scaffold protein. The membrane forming lipids and scaffold protein are components of the NLP. In particular the membrane forming lipid component is part of a total lipid component, (herein also membrane lipid component or lipid component) of the NLP together with additional lipids such as functionalized lipids and polymerizable lipids, that can further be included in the NLPs as will be understood by a skilled person upon reading of the present disclosure. The scaffold protein component is part of a protein component of the NLP together with additional proteins such as membrane proteins, target proteins and other proteins that can be further included as components of the NLPs as will be understood by a skilled person upon reading of the present disclosure. Additional components can be provided as part of the NLP herein described as will be understood by a skilled person. In particular the membrane lipid bilayer can attach membrane proteins or other amphipathic compounds through interaction of respective hydrophobic regions with the membrane lipid bilayer. The membrane lipid bilayer can also attach proteins or other molecule through anchor compounds or functionalized lipids as will be understood by a skilled person upon reading of the disclosure. Predominately discoidal in shape, nanolipoprotein particles typically have diameters between 10 to 20 nm, share uniform heights between 4.5 to 5 nm and can be produced in yields ranging between 30 to 90%. The particular membrane forming lipid, scaffold protein, the lipid to protein ratio, and the assembly parameters determine the size and homogeneity of nanolipoprotein particles as will be understood by a skilled person. In the nanolipoprotein particle the membrane forming lipid are typically arranged in a membrane lipid bilayer confined by the scaffold protein in a discoidal configuration as will be understood by a skilled person.

The term "membrane forming lipid" or "amphipathic lipid" as used herein indicates a lipid possessing both hydrophilic and hydrophobic properties that in an aqueous environment assemble in a lipid bilayer structure that consists of two opposing layers of amphipathic molecules know as polar lipids. Each polar lipid has a hydrophilic moiety, i.e. a polar group such as, a derivatized phosphate or a saccharide group, and a hydrophobic moiety, i.e., a long hydrocarbon chain. Exemplary polar lipids include phospholipids, sphingolipids, glycolipids, ether lipids, sterols, alkylphosphocholines and the like. Amphipathic lipids include but are not limited to membrane lipids, i.e. amphipathic lipids that are constituents of a biological membrane, such as phospholipids like dimyristoylphosphatidylcholine (DMPC) or dioleoylphosphoethanolamine (DOPE) or dioleoylphosphatidylcholine (DOPC), or dipalmitoylphosphatidylcholine (DPPC). In a preferred embodiment, the lipid is dimyristoylphosphatidylcholine (DMPC).

The term "scaffold protein" as used herein indicates any amphipathic protein that is capable of self-assembly with an amphipathic lipid in an aqueous environment, organizing the amphipathic lipid into a bilayer, and comprise apolipoproteins, lipophorins, derivatives thereof (such as truncated and tandemly arrayed sequences) and fragments thereof (e.g. peptides) which maintains the amphipathic nature and capability of self assembly, such as apolipoprotein E4, 22K fragment, lipophorin III, apolipoprotein A-1 and the like. In general scaffold protein have an alpha helical secondary structure in which a plurality of hydrophobic amino acids form an hydrophobic face and a plurality of hydrophilic amino acids form an opposing hydrophilic face. In some embodiments, rationally designed amphipathic peptides and synthetic apolipoproteins which maintain an amphipathic structure and capability of self assembly can serve as a scaffold protein of the NLP.

The term "apolipoprotein" as used herein indicates an amphipathic protein that binds lipids to form lipoproteins. The term "amphipathic" pertains to a molecule containing both hydrophilic and hydrophobic properties. Exemplary amphipathic molecules comprise, a molecule having hydrophobic and hydrophilic regions/portions in its structure. Examples of biomolecules which are amphipathic include but not limited to phospholipids, cholesterol, glycolipids, fatty acids, bile acids, saponins, and additional lipids identifiable by a skilled person. A "lipoprotein" as used herein indicates a biomolecule assembly that contains both proteins and lipids. In particular, in lipoproteins, the protein component surrounds or solubilizes the lipid molecules enabling particle formation. Exemplary lipoproteins include the plasma lipoprotein particles classified under high-density (HDL) and low-density (LDL) lipoproteins, which enable fats to be carried in the blood stream, the transmembrane proteins of the mitochondrion and the chloroplast, and bacterial lipoproteins. In particular, the lipid components of lipoproteins are insoluble in water, but because of their amphipathic properties, apolipoproteins such as certain Apolipoproteins A and Apolipoproteins B and other amphipathic protein molecules can surround the lipids, creating the lipoprotein particle that is itself water-soluble, and can thus be carried through water-based circulation (e.g. blood, lymph in vivo or in vitro). Apolipoproteins known to provide the protein components of the lipoproteins can be divided into six classes and several sub-classes, based on the different structures and functions. Exemplary apolipoprotein known to be able to form lipoproteins comprise Apolipoproteins A (apo A-I, apo A-II, apo A-IV, and apo A-V), Apolipoproteins B (apo B48 and apo B100), Apolipoproteins C (apo C-I, apo C-II, apo C-III, and apo C-IV), Apolipoproteins D, Apolipoproteins E, and Apolipoproteins H. For example apolipoproteins B can form low-density lipoprotein particles, and have mostly beta-sheet structure and associate with lipid droplets irreversibly, while Apolipoprotein A1 comprise alpha helices and can associate with lipid droplets reversibly forming high-density lipoprotein particles.

The term "protein" as used herein indicates a polypeptide with a particular secondary and tertiary structure that can interact with another molecule and in particular, with other biomolecules including other proteins, DNA, RNA, lipids, metabolites, hormones, chemokines, and/or small molecules. The term "polypeptide" as used herein indicates an organic linear, circular, or branched polymer composed of two or more amino acid monomers and/or analogs thereof. The term "polypeptide" includes amino acid polymers of any length including full length proteins and peptides, as well as analogs and fragments thereof. A polypeptide of three or more amino acids is also called a protein oligomer, peptide, or oligopeptide. In particular, the terms "peptide" and "oligopeptide" usually indicate a polypeptide with less than 100 amino acid monomers. In particular, in a protein, the polypeptide provides the primary structure of the protein, wherein the term "primary structure" of a protein refers to the sequence of amino acids in the polypeptide chain covalently linked to form the polypeptide polymer. A protein "sequence" indicates the order of the amino acids that form the primary structure. Covalent bonds between amino acids within the primary structure can include peptide bonds or disulfide bonds, and additional bonds identifiable by a skilled person. Polypeptides in the sense of the present disclosure are usually composed of a linear chain of alpha-amino acid residues covalently linked by peptide bond or a synthetic covalent linkage. The two ends of the linear polypeptide chain encompassing the terminal residues and the adjacent segment are referred to as the carboxyl terminus (C-terminus) and the amino terminus (N-terminus) based on the nature of the free group on each extremity. Unless otherwise indicated, counting of residues in a polypeptide is performed from the N-terminal end ($NH_2$-group), which is the end where the amino group is not involved in a peptide bond to the C-terminal end (—COOH group) which is the end where a COOH group is not involved in a peptide bond. Proteins and polypeptides can be identified by x-ray crystallography, direct sequencing, immuno precipitation, and a variety of other methods as understood by a person skilled in the art. Proteins can be provided in vitro or in vivo by several methods identifiable by a skilled person. In some instances where the proteins are synthetic proteins in at least a portion of the polymer two or more amino acid monomers and/or analogs thereof are joined through chemically-mediated condensation of an organic acid (—COOH) and an amine (—$NH_2$) to form an amide bond or a "peptide" bond.

As used herein the term "amino acid", "amino acid monomer", or "amino acid residue" refers to organic compounds composed of amine and carboxylic acid functional groups, along with a side-chain specific to each amino acid. In particular, alpha- or α-amino acid refers to organic compounds composed of amine (—NH2) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to forma polymer through peptide bonds by reactions between the amine group of a first amino acid and the carboxylic acid group of a second amino acid. Amino acid in the sense of the disclosure refers to any of the twenty naturally occurring amino acids, non-natural amino acids, and includes both D an L optical isomers In embodiments herein described a nanolipoprotein particles comprise one or more polymerizable lipids within the membrane lipid bilayer also comprising one or more membrane forming lipids.

The term "polymerizable lipid" as used herein indicates a lipid molecule comprising at least one functional group presented for reaction with a corresponding functional group in presence of a crosslinking agent or initiator to provide a polymer formed by two or more same or different lipid molecules. Polymerizable lipids herein described therefore present corresponding functional groups in a configuration allowing reaction of the corresponding functional groups upon introduction of a cross-linking agent or initiator to provide polymerized lipid molecules.

The term "functional group" as used herein indicates specific groups of atoms within a molecular structure that are responsible for a characteristic chemical reaction of that structure. Exemplary functional groups include hydrocarbons, groups containing double or triple bonds, groups containing halogen, groups containing oxygen, groups containing nitrogen and groups containing phosphorus and sulfur all identifiable by a skilled person.

Functional groups presented in polymerizable lipids to provide polymerized lipids (herein also polymerizable functional groups) can contain at least one double and/or triple bond that can react in presence of the crosslinking agent or initiator to provide the polymerized lipid comprising at least two polymerizable lipid bound to one another. In particular, in embodiments here described one or more polymerizable functional groups comprising one double and/or triple bond is located in the hydrophobic region of the polymerizable lipid molecule. More particularly polymerizable functional groups within polymerizable lipids comprise various groups (e.g. hydrocarbon group, a group containing oxygen, a group containing nitrogen and a group containing phosphorus and/or sulfur) presenting at least one double and/or triple bond. In particular, functional groups in the sense of the present disclosure include diacetylene groups [1, 2], methacrylate groups [3, 4], acryloyl groups [5, 6], sorbyl ester groups [7], diene groups [8, 9], styrene groups [10], vinyl groups [10] and isocyano groups [10]. Additional functional groups can be identified by a skilled person upon reading of the present disclosure.

The term "corresponding" used in connection with elements such as functional groups identify two or more elements capable of reacting one with another under appropriate conditions. Typically, a reaction between corresponding moieties and in particular functional groups, results in binding of the two elements.

The term "bind", "binding", "conjugation" as used herein indicates an attractive interaction between two elements which results in a stable association of the element in which the elements are in close proximity to each other. If each element is comprised in a molecule the result of binding is typically formation of a molecular complex. Attractive interactions in the sense of the present disclosure includes both non-covalent binding and, covalent binding. Covalent binding indicates a form of chemical bonding that is characterized by the sharing of pairs of electrons between atoms, or between atoms and other covalent bonds. For example, attraction-to-repulsion stability that forms between atoms when they share electrons is known as covalent bonding. Covalent bonding includes many kinds of interaction, including σ-bonding, π-bonding, metal to non-metal bonding, agostic interactions, and three-center two-electron bonds. Non-covalent binding as used herein indicates a type of chemical bond, such as protein protein interaction, that does not involve the sharing of pairs of electrons, but rather involves more dispersed variations of electromagnetic interactions. Non-covalent bonding includes ionic bonds, hydrophobic interactions, electrostatic interactions, hydrogen bonds, and dipole-dipole bonds. Electrostatic interactions include association between two oppositely charged entities. An example of an electrostatic interaction includes using a charged lipid as the functional membrane lipid and binding an oppositely charged target molecule through electrostatic interactions.

Exemplary corresponding functional groups capable of reacting in presence of an initiator to provide polymerized lipids comprise diacetylene groups (initiator—UV exposure) [1, 2], methacrylate groups (initiator—UV exposure, azobisisobutyronitrile (AIBN)+heat) [3, 4], acryloyl groups (initiator—(AIBN)+heat) [5, 6], sorbyl ester groups (initiator—UV exposure, azobisisobutyronitrile (AIBN)+heat) [7], diene groups (initiator—UV exposure, azobisisobutyronitrile (AIBN)+heat, azobis(2-amidinopropane) dihydrochloride (AAPD)+heat) [8, 9], styrene groups (initiator—UV exposure) [10], vinyl groups (initiator—UV exposure) [10] and isocyano groups (initiator—UV exposure) [10]. In some embodiments, in polymerizable lipids herein described at least one polymerizable functional group is selected from diacetylenyl, acryloyl, methacryloyl and dienyl groups.

In embodiments herein described, corresponding functional groups within polymerizable lipids bind upon exposure to an initiator or crosslinking agent. The term "initiator" or "crosslinking agent" as used herein indicates any agent that can react with one or more polymerizable lipids to provide a polymerized lipid formed by at least two polymerizable lipid molecules bound one to another via covalent linkage of corresponding functional groups.

Typically, initiators in the sense of the disclosure can react with at least one of the functional groups of a polymerizable lipid to provide an activated polymerizable lipid presenting a free radical on the at least one functional group. Reaction of one or more activated polymerizable lipid monomer with another lipid monomer of a same of different polymerizable lipid monomer typically starts a chain of reaction resulting in formation of a polymerized or cross-linked lipid in the sense of the disclosure. Exemplary initiators in the sense of the disclosure comprise photons (e.g. provided by UV light or other light source) and chemical species (e.g. photoinitiators and thermal initiators) that can provide free radicals under appropriate conditions.

The term "photoinitiator" as used herein is a compound capable of absorbing a photon in the form of UV or visible light, to generate a free radical. Exemplary photoinitiators include acetophenone, anisoin, anthraquinone, anthraquinone-2-sulfonic acid, sodium salt, (benzene) tricarbonylchromium, benzil, benzoin, benzoin ethyl ether, benzoin isobutyl ether, benzoin methyl ether, benzophenone, benzophenone/1-hydroxycyclohexyl phenylketone, 50/50 blend, 3,3',4,4'-benzophenonetetracarboxylic dianhydride, 4-benzoylbiphenyl, 2-benzyl-2-(dimethylamino)-4'-morpholinobutyrophenone, 4,4'-bis(diethylamino)benzophenone, 4,4'-bis(dimethylamino)benzophenone, camphorquinone, 2-chlorothioxanthen-9-one, (cumene)cyclopentadienyliron(II) hexafluorophosphate, dibenzosuberenone, 2,2-diethoxyacetophenone, 4,4'-dihydroxybenzophenone, 2,2-Dimethoxy-2-phenylacetophenone, 4-(dimethylamino)benzophenone, 4,4'-dimethylbenzil, 2,5-dimethylbenzophenone, 3,4-dimethylbenzophenone, diphenyl(2,4,6-trimethylbenzoyl)phosphine oxide/2-hydroxy-2-methylpropiophenone, 50/50 blend, 4'-ethoxyacetophenone, 2-ethylanthraquinone, ferrocene, 3'-hydroxyacetophenone, 4'-hydroxyacetophenone, 3-hydroxybenzophenone, 4-hydroxybenzophenone, 1-hydroxycyclohexyl phenyl ketone, 2-hydroxy-2-methylpropiophenone, 2-methylbenzophenone, 3-methylbenzophenone, methybenzoylformate, 2-methyl-4'-(methylthio)-2-morpholinopropiophenone, phenanthrenequinone, 4'-phenoxyacetophenone, thioxanthen-9-one, triarylsulfonium hexafluoroantimonate salts, mixed, 50% in propylene carbonate, triarylsulfonium hexafluorophosphate salts, mixed, 50% in propylene carbonate or a combination thereof.

The "thermal initiators" as used herein indicates a compound capable of absorbing thermal energy to generate a free radical. Exemplary thermal initiators include azo initiators, organic peroxides and inorganic peroxides. The term "azo initiators" as used herein indicates e compounds bearing the functional group R—N=N—R', in which R and R' can be either aryl or alkyl. Exemplary azo initiators comprise 4,4'-Azobis(4-cyanovaleric acid), 1,1'-Azobis(cyclohexanecarbonitrile), Azobisisobutyronitrile, 2,2'-Azobis(2-methylpropionamidine) dihydrochloride, 2,2'-Azobis(2-methylpropionitrile). The term "peroxide" as used herein indicates organic or inorganic compounds having a peroxide bond (—O—O—). Exemplary, organic peroxide initiator includes benzoyl peroxide, dicumyl peroxide, di-tert-butyl peroxide, methyl ethyl ketone peroxide, tert-butyl peracetate, 2,5-di(tert-butylperoxy)-2,5-dimethyl-3-hexyne, 2,5-Bis(tert-butylperoxy)-2,5-dimethylhexane, 2,4-Pentanedione peroxide, 1,1-bis(tert-butylperoxy)cyclohexane, 1,1-bis(tert-amylperoxy)cyclohexane, 2-butanone peroxide, lauroyl peroxide, tert-butyl peroxybenzoate, tert-butylperoxy 2-ethylhexyl carbonate, tert-butyl hydroperoxide. Exemplary inorganic peroxides include potassium persulfate, ammonium persulfate or sodium persulfate which all can be used as initiator.

Detection of free radicals can be performed with electron paramagnetic resonance spectroscopy, nuclear magnetic resonance (specifically chemically induced dynamic nuclear polarization), and additional techniques identifiable by a skilled person.

In embodiments, herein described, upon action of the initiator, functional groups within the polymerizable lipids react forming cross-links between the polymerizable lipids presenting the functional groups. A cross-link is a covalent bonds or ionic bond that links one polymerizable lipid to another. Resulting cross-linked polymerizable lipids can comprise one or more cross-links between corresponding functional groups as will be understood by a skilled person. Cross-linked molecules can be identified by a number of techniques such as high performance liquid chromatography, spectroscopy, SDS-polyacrylamide gel electrophoresis, rheology analysis and image analysis (electron microscopy, atomic force microscopy), dynamic light scattering, fluorescence correlation spectroscopy, differential scanning calorimetry, and additional techniques identifiable by a skilled person.

Exemplary initiators and corresponding functional groups comprise diacetylene groups (exemplary initiator: UV exposure) [1, 2], methacrylate groups (exemplary initiators: UV exposure, azobisisobutyronitrile (AIBN)+heat) [3, 4], acryloyl groups (exemplary initiator: (AIBN)+heat) [5, 6], sorbyl ester groups (exemplary initiators: UV exposure, azobisisobutyronitrile (AIBN)+heat) [7], diene groups (exemplary initiators: —UV exposure, azobisisobutyronitrile (AIBN)+heat, azobis(2-amidinopropane) dihydrochloride (AAPD)+heat) [8, 9], styrene groups (exemplary initiator: UV exposure) [10], vinyl groups (exemplary initiator: UV exposure) [10] and isocyano groups (exemplary initiator: UV exposure) [10].

Polymerizable lipids in the sense of the disclosure comprises lipids used to provide stable multilayers of long chained fatty acids that display unique physical properties such as photoconductivity, photochemistry and photophysics [11], lipids used to stabilize planar lipid structures (see e.g. [12]), lipids used to form lipid assemblies in a variety of configurations (see e.g. [1], [14-15], [16]) as well as commercially available lipids including components in sensors [2, 13] and in vesicle-based drug-delivery vehicles [14-16]. One specific type of polymerizable lipid that is often used is based on long-chain diacetylene monocarboxylic acids, which have been well-studied and have been shown to form intermolecular covalent bonds as a result of exposure to ultraviolet light at 254 nanometers [11, 17, 18].

In some embodiments, polymerizable lipids comprise lipids of Formula (I)

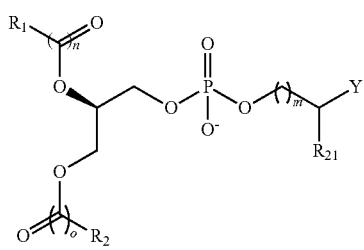

wherein
R1 and R2 are independently selected from C7-C29 branched or straight, substituted or unsubstituted aliphatic carbon chain, at least one of R1 and R2 presents at least one polymerizable functional group;

$$Z = \text{---}S\text{---}R_{11}, \quad (II)$$

$$\text{---}O\text{---}R_{11} \quad \text{or} \quad (IV)$$

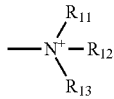 (V)

in which $R_{11}$, $R_{12}$ and $R_{13}$ are independently H or a C1-C4 branched or straight aliphatic carbon chain;
$R_{21}$ is H, OH, or a carboxy group
m=0-3; and
n and o are independently 0 and 1.

In some embodiments, $R_1$ and $R_2$ present at least two polymerizable functional groups for polymerization with corresponding functional groups.

As used herein, the term "aliphatic" refers to that is an alkyl, alkenyl or alkynyl group which can be substituted or unsubstituted, linear, branched or cyclic.

As used herein the term "alkyl" as used herein refers to a linear, branched, or cyclic, saturated hydrocarbon group formed by a carbon chain. As used herein the term "carbon chain" indicates a linear or branched line of connected carbon atoms. An alkyl carbon chain typically although not necessarily containing 1 to about 18 carbon atoms, preferably 1 to about 6 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 6 carbon atoms. The term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

As used herein the term "alkenyl" indicates a linear, branched, or cyclic hydrocarbon group that contains at least one carbon-carbon double bond. As used herein the term "alkynyl" indicates a linear, branched, or cyclic hydrocarbon group that contains at least one carbon-carbon triple bond.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 12 carbon atoms, and particularly preferred aryl groups contain 5 to 6 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, such as nitrogen, oxygen or sulfur.

As used herein the terms "heteroatom-containing" or "hetero-" indicated in connection with a group, refers to a hydrocarbon group in which one or more carbon atoms is replaced with an atom other than carbon, e.g., nitrogen, oxygen, sulfur, phosphorus or silicon, typically nitrogen, oxygen or sulfur. Exemplary "heteroatoms" comprise as N, O, S and P, and can be present in a compound by a covalent bond to each of two carbon atoms, thus interrupting the two carbon atoms. Accordingly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, and addition group identifiable by a skilled person.

The term "aralkyl" as used herein refers to an alkyl group with an aryl substituent, and the term "alkaryl" as used herein refers to an aryl group with an alkyl substituent, wherein "aryl" and "alkyl" are as defined above. In some embodiments, alkaryl and aralkyl groups contain 6 to 12 carbon atoms, and particularly alkaryl and aralkyl groups contain 6 to 16 carbon atoms. Alkaryl groups include, for example, p-methylphenyl, 2,4-dimethylphenyl, p-cyclohexylphenyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, and the like. The terms "alkaryloxy" and "aralkyloxy" refer to substituents of the formula —OR wherein R is alkaryl or aralkyl, respectively, as defined.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

Unless otherwise indicated, the term "substituted" as in "substituted alkyl," "substituted aryl," and the like, is meant that in the, alkyl, aryl, or other moiety, at least one hydrogen atom bound to a carbon (or other) atom is replaced with one or more non-hydrogen substituents. As used herein, a "substituent" is an atom or group of atoms substituted in place of a hydrogen atom on the main chain of a hydrocarbon. Examples of such substituents include, without limitation: functional groups such as, hydroxyl, sulfhydryl, $C_1$-$C_{12}$ alkoxy, $C_2$-$C_{12}$ alkenyloxy, $C_2$-$C_{12}$ alkynyloxy, $C_5$-$C_{12}$ aryloxy, $C_6$-$C_{12}$ aralkyloxy, $C_6$-$C_{12}$ alkaryloxy, acyl (including $C_2$-$C_{12}$ alkylcarbonyl (—CO-alkyl) and $C_6$-$C_{12}$ arylcarbonyl (—CO-aryl)), acyloxy (—O-acyl, including $C_2$-$C_{12}$ alkylcarbonyloxy (—O—CO-alkyl) and $C_6$-$C_{12}$ arylcarbonyloxy (—O—OO-aryl)), $C_2$-$C_{12}$ alkoxycarbonyl (—(CO)—O-alkyl), $C_6$-$C_{12}$ aryloxycarbonyl (—(CO)—O-aryl), $C_2$-$C_{12}$ alkylcarbonato (—O—(CO)—O-alkyl), $C_6$-$C_{12}$ arylcarbonato (—O—(CO)—O-aryl), carboxy (—COOH), carboxylato (—COO$^-$), carbamoyl (—(CO)—NH$_2$), mono-($C_1$-$C_{12}$ alkyl)-substituted carbamoyl (—(CO)—NH($C_1$-$C_{12}$ alkyl)), di-($C_1$-$C_{12}$ alkyl)-substituted carbamoyl (—(CO)—N($C_1$-$C_{12}$ alkyl)$_2$), mono-($C_5$-$C_{12}$ aryl)-substituted carbamoyl (—(CO)—NH-aryl), di-($C_5$-$C_{12}$ aryl)-substituted carbamoyl (—(CO)—N($C_5$-$C_{12}$ aryl)$_2$), di-N—($C_1$-$C_6$ alkyl), N—($C_5$-$C_{12}$ aryl)-substituted carbamoyl, thiocarbamoyl (—(CS)—NH$_2$), mono-($C_1$-$C_{12}$ alkyl)-substituted thiocarbamoyl (—(CO)—NH($C_1$-$C_{12}$ alkyl)), di-($C_1$-$C_{12}$ alkyl)-substituted thiocarbamoyl (—(CO)—N($C_1$-$C_6$ alkyl)$_2$), mono-($C_5$-$C_{12}$ aryl)-substituted thiocarbamoyl (—(CO)—NH-aryl), di-($C_5$-$C_6$ aryl)-substituted thiocarbamoyl (—(CO)—N($C_5$-$C_6$ aryl)$_2$), di-N—($C_1$-$C_6$ alkyl), N—($C_5$-$C_6$ aryl)-substituted thiocarbamoyl, carbamido (—NH—(CO)—NH$_2$), cyano(—C≡N), cyanato (—O-thiocyanato C≡N), thiocyanato (—S—C≡N), formyl (—(CO)—H), thioformyl (—(CS)—H), amino (—NH$_2$), mono-($C_1$-$C_{12}$ alkyl)-substituted amino, di-($C_1$-$C_{12}$ alkyl)-substituted amino, mono-($C_5$-$C_{12}$ aryl)-substituted amino, di-($C_5$-$C_6$ aryl)-substituted amino, $C_2$-$C_{12}$ alkylamido (—NH—(CO)-alkyl), $C_6$-$C_{12}$ arylamido (—NH—(CO)-aryl), imino (—CR=NH where R=hydrogen, $C_1$-$C_{12}$ alkyl, $C_5$-$C_{12}$ aryl, $C_6$-$C_{12}$ alkaryl, $C_6$-$C_{12}$ aralkyl, etc.), $C_2$-$C_{12}$ alkylimino (—CR=N(alkyl), where R=hydrogen, $C_1$-$C_{12}$ alkyl, $C_5$-$C_{12}$ aryl, $C_6$-$C_{12}$ alkaryl, $C_6$-$C_2$ aralkyl, etc.), arylimino (—CR=N(aryl), where R=hydrogen, $C_1$-$C_{12}$ alkyl, $C_5$-$C_2$ aryl, $C_6$-$C_{12}$ alkaryl, $C_6$-$C_{12}$ aralkyl, etc.), nitro (—NO$_2$), nitroso (—NO), sulfo (—SO$_2$—OH), sulfonato (—SO$_2$—O$^-$), $C_1$-$C_{12}$ alkylsulfanyl (—S-alkyl; also termed "alkylthio"), $C_5$-$C_{12}$ arylsulfanyl (—S-aryl; also termed "arylthio"), $C_1$-$C_{12}$ alkylsulfinyl (—(SO)-alkyl), $C_5$-$C_{12}$ arylsulfinyl (—(SO)-aryl), $C_1$-$C_{12}$ alkylsulfonyl (—SO$_2$-alkyl), $C_5$-$C_{12}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O$^-$)$_2$), phosphinato (—P(O)(O$^-$)), phospho (—PO$_2$), phosphino (—PH$_2$), silyl (—SiR$_3$ wherein R is hydrogen or hydrocarbyl), and silyloxy (—O-silyl); and the hydrocarbyl moieties $C_1$-$C_{12}$ alkyl (preferably $C_1$-$C_{12}$ alkyl, more preferably $C_1$-$C_6$ alkyl), $C_2$-$C_2$ alkenyl (preferably $C_2$-$C_2$ alkenyl, more preferably $C_2$-$C_6$ alkenyl), alkynyl (preferably $C_2$-$C_{12}$ alkynyl, more preferably $C_2$-$C_6$ alkynyl), $C_5$-$C_{12}$ aryl (preferably $C_5$-$C_{12}$ aryl), $C_6$-$C_{12}$ alkaryl (preferably $C_6$-$C_{12}$ alkaryl), and $C_6$-$C_{12}$ aralkyl (preferably $C_6$-$C_{12}$ aralkyl).

In some embodiments, polymerizable lipids comprise lipids of Formula (I) group Z is the ammonium group of formula V.

In some embodiments, polymerizable lipids comprise lipids of Formula (VI)

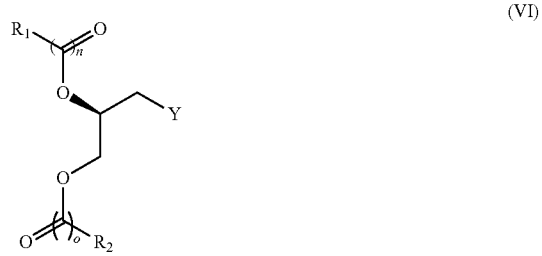

(VI)

wherein
$R_1$, $R_2$ are independently a C7-C29 branched or straight, substituted or unsubstituted aliphatic carbon chain:

$$Y = \text{—O—}R_3, \quad \text{(VII)}$$

$$\text{—S—}R_3, \text{ or} \quad \text{(VIII)}$$

(IX)

in which $R_{11}$, $R_{12}$ are independently H or a C1-C4 branched or straight aliphatic carbon chain and $R_3$ is a C7-C29 branched or straight, substituted or unsubstituted aliphatic carbon chain,
n and o are independently 0 and 1;
and wherein at least one of $R_1$, $R_2$ and $R_3$ contains at least one polymerizable functional group.

In some embodiments, $R_1$, $R_2$ and $R_3$ present at least two polymerizable functional groups for polymerization with corresponding functional groups.

In some embodiments, at least one of $R_1$, $R_2$ and $R_3$ in polymerizable lipids of Formula (I) and (VI) contains 1-6 units of an ethyleneoxy group —(CH$_2$CH$_2$O)—.

In some embodiments, polymerizable lipids are lipids of Formula (X)

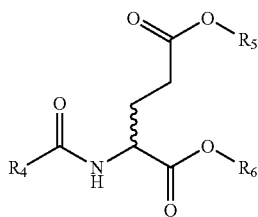

wherein
$R_4$, $R_5$ and $R_6$ are independently C7-C29 branched or straight, substituted or unsubstituted aliphatic carbon chain, at least one of $R_4$, $R_5$ and $R_6$ contains at least one polymerizable functional group, and at least one of $R_4$, $R_5$ and $R_6$ contains at least one amino nitrogen.

In some embodiments, in polymerizable lipids of Formula (X) at least one of $R_4$, $R_5$ and $R_6$ contains 1-6 units of an ethyleneoxy group —(CH$_2$CH$_2$O)—.

In some embodiments, the polymerizable functional group in the polymerizable lipids of Formula (I), (VI) and (X) can be selected from one of diacetylene groups [1, 2], methacrylate groups [3, 4], acryloyl groups [5, 6], sorbyl ester groups [7], diene groups [8, 9], styrene groups [10], vinyl groups [10] and isocyano groups [10].

In embodiments herein described NLP comprise polymerizable lipid, membrane forming lipids and scaffold protein in ratios and proportions that would be identifiable by a skilled person upon reading of the present disclosure.

In some embodiments, NLPs herein described have a lipid component to scaffold molar ratio ranging from 20:1 to 240:1, depending on the scaffold protein used as will be understood by a skilled person. For example, in NLPs herein described having apoE422k variants as scaffold protein and DOPC as the membrane forming lipid, the molar ratios of lipid component: scaffold protein component can range from 40:1 to 240:1, where the lipid molar ratios (membrane forming lipid to polymerizable lipid) within the lipid component of the NLP can range from 95:5 to 60:40 (e.g. Example 5 FIG. 5A).

In some embodiments, NLPs herein described have a lipid component comprising membrane forming lipid in an amount from 95 to 60 mol % of the lipid component and the polymerizable lipid in an amount from 5 to 40 mol % of the lipid component. In some embodiments, the NLP herein described comprise membrane forming lipid and polymerizable lipids in molar ratios ranging from 90:10 to 60:40 (see e.g. Example 5 with 1,2-dioleoyl-sn-glycero-3-phosphocholine (DOPC) and related FIG. 5A).

In preferred embodiments, where the NLP comprise at least 20 mol % of polymerizable lipids, NLPs described herein can have a lipid:polymerizable lipid:scaffold protein ratio range of 32:8:1 to 160:40:1, with exact molar ratios depending on the optimal lipid:protein ratio for that lipid mixture and scaffold protein identifiable by a skilled person upon reading of the present disclosure.

In some embodiments the polymerizable lipids are comprised within an NLP herein described in a molar lipid concentration of about 5 to 40%, preferably about 20% In some embodiments, the polymerizable lipids can be comprised within an NLP herein described in an amount of less than 10% of the total lipid content of the NLP. In some embodiments, one or more polymerizable lipids can be comprised in NLPs herein described in an amount inversely proportional to the number of polymerizable functional groups comprised in the polymerizable lipid. In particular, in some of those embodiments a minimum content for a polymerizable lipid with one polymerizable functional group can approximately twice that of a polymerizable lipid with two polymerizable functional groups as would be understood by a skilled person.

In some embodiments, at least parts of the polymerizable lipids within the membrane lipid bilayer of the NLP herein described are polymerized to provide a cross-linked membrane lipid bilayer.

The term "cross-linked membrane lipid bilayer" as used herein indicates a membrane lipid bilayer in which at least part of polymerizable lipids comprised within the membrane lipid bilayer are polymerized. The term "polymerized" or "cross-linked" when referred to polymerizable lipids indicates binding of at least two polymerizable lipid through binding of at least two corresponding polymerizable functional groups presented on the at least two polymerizable lipids. In some embodiments, of NLPs herein described comprising a cross-linked membrane lipid bilayer a majority of the polymerizable lipids contained within the membrane lipid bilayer are cross-linked and in particular attached one to at least one another through covalent bonds.

The term "attach" or "attached" as used herein, refers to connecting or uniting by a bond, link, force or tie in order to keep two or more components together, which encompasses either direct or indirect attachment where, for example, a first molecule is directly bound to a second molecule or material, or one or more intermediate molecules are disposed between the first molecule and the second molecule or material.

A cross-linked membrane can be identified through reverse phase High Performance Liquid Chromatography (HPLC) and additional techniques identifiable by a skilled person in which, NLP components can be separated and then quantified. For example by quantifying the amount of free lipids and in particular of free polymerizable lipids remaining following crosslinking, the number of polymerized lipids can be estimated. Reverse phase HPLC will not cause the polymerized lipids to separate, so a distribution of peaks can be observed in the chromatogram that represents the variation in molecular weight for the cross-linked molecules that randomly form as a result of crosslinking. Detection of a degree of cross-linking can be performed according to those techniques both qualitatively and quantitatively as would be understood by a skilled person (see e.g. Example 5)

In some embodiments, the NLPs herein described that are cross-linked or crosslinkable, the lipid component comprises at least a membrane forming lipids component and a polymerizable lipids component.

In particular, in some embodiments, the membrane forming lipids component comprises lipids such as phospholipids, preferably including at least one phospholipid, typically soy phosphatidylcholine, egg phosphatidylcholine, soy phosphatidylglycerol, egg phosphatidylglycerol, palmitoyl-oleoyl-phosphatidylcholine distearoylphosphatidylcholine, or distearoylphosphatidylglycerol. Other useful phospholipids include, e.g., phosphatidylcholine, phosphatidylglycerol, sphingomyelin, phosphatidylserine, phosphatidic acid, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, stearoyl-palmitoyl-phosphatidylcholine, di-palmitoyl-phosphatidylethanolamine, di stearoyl-phosphatidylethanolamine, di-myrstoyl-phosphatidylserine, and dioleyl-phosphatidylcholine.

Additionally exemplary membrane forming lipids that can be comprised in various combinations together with one or more polymerizable lipids comprise 1,2-dipalmitoyl-sn-glycero-3-phosphocholine, 1,2-dimyristoyl-sn-glycero-3-phosphocholine, 1,2-dilauroyl-sn-glycero-3-phosphocholine, 1,2-didecanoyl-sn-glycero-3-phosphocholine, 1,2-dierucoyl-sn-glycero-3-phosphocholine, 1,2-dioleoyl-sn-glycero-3-phosphocholine, 1,2-dipalmitoleoyl-sn-glycero-3-phosphocholine, 1,2-dimyristoleoyl-sn-glycero-3-phosphocholine, 1-stearoyl-2-oleoyl-sn-glycero-3-phosphocholine, 1-stearoyl-2-myristoyl-sn-glycero-3-phosphocholine, 1-palmitoyl-2-oleoyl-sn-glycero-3-phosphocholine, egg phosphatidylcholine extracts, soy phosphatidylcholine extracts, heart phosphatidylcholine extracts, brain phosphatidylcholine extracts, liver phosphatidylcholine extracts, 1,2-di stearoyl-sn-glycero-3-phosphate, 1,2-dipalmitoyl-sn-glycero-3-phosphate, 1,2-dimyristoyl-sn-glycero-3-phosphate, 1,2-dilauroyl-sn-glycero-3-phosphate, 1-palmitoyl-2-oleoyl-sn-glycero-3-phosphate, 1-stearoyl-2-oleoyl-sn-glycero-3-phosphate, 1,2-dipalmitoyl-sn-glycero-3-phosphoethanolamine, 1,2-dimyristoyl-sn-glycero-3-phosphoethanolamine, 1,2-dilauroyl-sn-glycero-3-phosphoethanolamine, 1,2-dioleoyl-sn-glycero-3-phosphoethanolamine, 1,2-dipalmitoleoyl-sn-glycero-3-phosphoethanolamine, Egg phosphatidyl ethanolamine extract, soy phosphatidylethanolamine extract, heart phosphatidylethanolamine extract, brain phosphatidylethanolamine extract, 1,2-di stearoyl-sn-glycero-3-phospho-(1'-rac-glycerol), 1,2-dioleoyl-sn-glycero-3-phospho-(1'-rac-glycerol), 1,2-dipalmitoyl-sn-glycero-3-phospho-(1'-rac-glycerol), 1,2-dimyristoyl-sn-glycero-3-phospho-(1'-rac-glycerol), 1,2-dilauroyl-sn-glycero-3-phospho-(1'-rac-glycerol), 1-palmitoyl-2-oleoyl-sn-glycero-3-phospho-(1'-rac-glycerol), egg phosphatidylglycerol extract, soy phosphatidylglycerol extract, 1,2-di stearoyl-sn-glycero-3-phospho-L-serine, 1,2-dioleoyl-sn-glycero-3-phospho-L-serine, 1,2-dipalmitoyl-sn-glycero-3-phospho-L-serine, 1,2-dimyristoyl-sn-glycero-3-phospho-L-serine, 1,2-dilauroyl-sn-glycero-3-phospho-L-serine, 1-palmitoyl-2-oleoyl-sn-glycero-3-phospho-L-serine, soy phosphatidylserine extract, brain phosphatidylserine extract, 2-((2,3-bis(oleoyloxy)propyl)dimethylammonio)ethyl hydrogen phosphate, cholesterol, ergosterol, sphingolipids, ceramides, sphingomyelin, gangliosides, glycosphingolipids, 1,2-di oleoyl-3-trimethyl ammonium-propane, 1,2-di-O-octadecenyl-3-trimethylammonium propane.

In some embodiments, non-phosphorus containing lipids can also be used as membrane forming lipids in NLPs herein described, e.g. stearylamine, docecylamine, acetyl palmitate, and fatty acid amides. Additional membrane forming lipids suitable for use in providing NLPs are well known to persons of skill in the art and are cited in a variety of well-known sources, e.g., McCutcheon's Detergents and Emulsifiers and McCutcheon's Functional Materials, Allured Publishing Co., Ridgewood, N.J., both of which are incorporated herein by reference.

In some embodiments, the polymerizable lipid component comprise lipids such as 1,2-bis(10,12-tricosadiynoyl)-sn-glycero-3-phosphocholine (polymerizable group in both acyl chains), 1,2-bis(10,12-tricosadiynoyl)-sn-glycero-3-phosphoethanolamine (polymerizable group in both acyl chains), 1-palmitoyl-2-(10,12-tricosadiynoyl)-sn-glycero-3-phosphocholine (polymerizable group in one acyl chain), 1-palmitoyl-2-(10,12-tricosadiynoyl)-sn-glycero-3-phosphoethanolamine (polymerizable group in one acyl chain), rac-1-stearoyl-2-(octadeca-2,4-trans,-frans-dienoyl)glycero-3-phosphorylcholine, rac-1,2-bis(octade-ca-2,4-~rans,frans-dienoyl)glycero-3-phosphorylcholine, bis(docosa-10,12-diyl) N-[6(triethyla"onio) hexanoyll-~-glutamate bromide, N-[11-(trimethyla"onino)undecanoyll-~-glutamate bromide, N-[4 (trimethyla"onio)-butoxybenzoyl] glutamate bromide, 2,3-Bis(hexadecanoyloxy) propy]-9-methacryloyl-3,6,9-trioxanonyldimethylanimonium Iodide, 12-Methacryloyl-3,6,9,12-tetraoxadodecyl 3-(Ar,iV-Dioctadecylcarbamoyl) propionate, 2,3-Bis(hexadecyloxy)propyl 12-Methacryloyl-3,6,9,12-tetraoxadodecyl Succinate, Sodium 2,3-Bis(hexadecyloxy)propyl-12-methacryloyl-3,6,9,12-tetraoxadodecylphosphate, In some embodiments various combinations and ratios of membrane forming lipids and polymerizable lipids can be comprised within an NLP herein described, such as 1,2-dimyristoyl-sn-glycero-3-phosphocholine and 1,2-bis(10,12-tricosadiynoyl)-sn-glycero-3-phosphocholine (ratio range 0.9:0.1-0.6:0.4), 1,2-dilauroyl-sn-glycero-3-phosphocholine and 1,2-bis(10,12-tricosadiynoyl)-sn-glycero-3-phosphocholine (ratio range 0.9:0.1-0.6:0.4), 1-palmitoyl-2-oleoyl-sn-glycero-3-phosphocholine and 1,2-bis(10,12-tricosadiynoyl)-sn-glycero-3-phosphocholine (ratio range 0.9:0.1-0.6:0.4), egg phosphatidylcholine extracts and 1,2-bis(10,12-tricosadiynoyl)-sn-glycero-3-phosphocholine (ratio range 0.9:0.1 to 0.6:0.4), 1,2-dierucoyl-sn-glycero-3-phosphocholine and 1,2-bis(10,12-tricosadiynoyl)-sn-glycero-3-phosphocholine (ratio range 0.9:0.1 to 0.6:0.4), 1,2-dimyristoyl-sn-glycero-3-phosphocholine and 1-palmitoyl-2-(10,12-tricosadiynoyl)-sn-glycero-3-phosphocholine (ratio range 0.9:0.1 to 0.6:0.4), 1,2-dilauroyl-sn-glycero-3-phosphocholine and 1-palmitoyl-2-(10,12-tricosadiynoyl)-sn-glycero-3-phosphocholine (ratio range 0.9:0.1 to 0.6:0.4), 1-palmitoyl-2-oleoyl-sn-glycero-3-phosphocholine and 1-palmitoyl-2-(10,12-tricosadiynoyl)-sn-glycero-3-phosphocholine (ratio range 0.9:0.1 to 0.6:0.4), egg phosphatidylcholine extracts and 1-palmitoyl-2-(10,12-tricosadiynoyl)-sn-glycero-3-phosphocholine (ratio range 0.9:0.1 to 0.6:0.4), 1,2-dierucoyl-sn-glycero-3-phosphocholine and 1-palmitoyl-2-(10,12-tricosadiynoyl)-sn-glycero-3-phosphocholine (ratio range 0.9:0.1 to 0.6:0.4), 1,2-dimyristoyl-sn-glycero-3-phosphocholine and rac-1-stearoyl-2-(octadeca-2,4-trans,-frans-dienoyl)glycero-3-phosphorylcholine (ratio range 0.9:0.1 to 0.6:0.4), 1,2-dilauroyl-sn-glycero-3-phosphocholine and rac-l-stearoyl-2-(octadeca-2,4-trans,-frans-dienoyl)glycero-3-phosphorylcholine (ratio range 0.9:0.1 to 0.6:0.4), 1-palmitoyl-2-oleoyl-sn-glycero-3-phosphocholine and rac-1-stearoyl-2-(octadeca-2,4-trans,-frans-dienoyl)glycero-3-phosphorylcholine (ratio range 0.9:0.1 to 0.6:0.4), egg phosphatidylcholine extracts and rac-1-stearoyl-2-(octadeca-2,4-trans,-frans-dienoyl)glycero-3-phosphorylcholine (ratio range 0.9:0.1 to 0.6:0.4), 1,2-dierucoyl-sn-glycero-3-phosphocholine and rac-1-stearoyl-2-(octadeca-2,4-trans,-frans-dienoyl)glycero-3-phosphorylcholine (ratio range 0.9:0.1 to 0.6:0.4).

In some embodiments the scaffold proteins can contain amino acid additions, deletions, or substitutions. In other embodiments, the scaffold proteins can be derived from various species and more particularly derived from human, mouse, rat, guinea pig, rabbit, cow, horse, pig, dog, and non-human primates.

In some embodiments various combinations of membrane forming lipids and polymerizable lpids in according with the disclosure can be comprised within an NLP stabilized by scaffold proteins such as human derived apoE4, truncated versions of human derived apoE4 (e.g. apoE422k), human derived apoE3, truncated versions of human derived apoE3 (e.g. apoE322k), human derived apoE2, truncated versions of human derived apoE2 (e.g. apoE222k), human derived apoA1, truncated versions of human derived apoA1 (e.g. Δ49ApoA1, MSP1, MSP1T2, MSP1E3D1), mouse derived apoE4, truncated versions of mouse derived apoE4 (e.g. apoE422k), mouse derived apoE3, truncated versions of mouse derived apoE3 (e.g. apoE322k), mouse derived apoE2, truncated versions of mouse derived apoE2 (e.g. apoE222k), mouse derived apoA1, truncated versions of mouse derived apoA1 (e.g. Δ49ApoA1, MSP1, MSP1T2, MSP1E3D1), rat derived apoE4, truncated versions of rat derived apoE4 (e.g. apoE422k), rat derived apoE3, truncated versions of rat derived apoE3 (e.g. apoE322k), rat derived apoE2, truncated versions of rat derived apoE2 (e.g. apoE222k), rat derived apoA1, truncated versions of rat derived apoA1 (e.g. Δ49ApoA1, MSP1, MSP1T2, MSP1E3D1), lipophorins (e.g. *B. mori, M. sexta*), synthetic cyclic peptides that mimic the function of apolipoproteins.

In some embodiments various combinations of membrane forming lipids and polymerizable lpids in according with the disclosure can be comprised within an NLP stabilized by different scaffold proteins, such as 1,2-dimyristoyl-sn-glycero-3-phosphocholine and 1,2-bis(10,12-tricosadiynoyl)-sn-glycero-3-phosphocholine (ratio range 0.9:0.1 to 0.6:0.4) with human derived apoE4422k (lipid:scaffold protein range 40:1 to 200:1). 1,2-dilauroyl-sn-glycero-3-phosphocholine and 1,2-bis(10,12-tricosadiynoyl)-sn-glycero-3-phosphocholine (ratio range 0.9:0.1 to 0.6:0.4) with human derived apoE4422k (lipid:scaffold protein range 40:1-200:1), 1-palmitoyl-2-oleoyl-sn-glycero-3-phosphocholine and 1,2-bis(10,12-tricosadiynoyl)-sn-glycero-3-phosphocholine (ratio range 0.9:0.1 to 0.6:0.4) with human derived apoE4422k (lipid:scaffold protein range 40:1 to 200:1), egg phosphatidylcholine extracts and 1,2-bis(10,12-tricosadiynoyl)-sn-glycero-3-phosphocholine (ratio range 0.9:0.1 to 0.6:0.4) with human derived apoE4422k (lipid:scaffold protein range 40:1 to 200:1), 1,2-dierucoyl-sn-glycero-3-phosphocholine and 1,2-bis(10,12-tricosadiynoyl)-sn-glycero-3-phosphocholine (ratio range 0.9:0.1 to 0.6:0.4) with human derived apoE4422k (lipid:scaffold protein range 40:1 to 200:1), 1,2-dimyristoyl-sn-glycero-3-phosphocholine and 1,2-bis(10,12-tricosadiynoyl)-sn-glycero-3-phosphocholine (ratio range 0.9:0.1 to 0.6:0.4) with MSP1E3D1 (lipid:scaffold protein range 20:1 to 100:1). 1,2-dilauroyl-sn-glycero-3-phosphocholine and 1,2-bis(10,12-tricosadiynoyl)-sn-glycero-3-phosphocholine (ratio range 0.9:0.1-0.6:0.4) with MSP1E3D1 (lipid:scaffold protein range 20:1 to 100:1), 1-palmitoyl-2-oleoyl-sn-glycero-3-phosphocholine and 1,2-bis(10,12-tricosadiynoyl)-sn-glycero-3-phosphocholine (ratio range 0.9:0.1 to 0.6:0.4) with MSP1E3D1 (lipid:scaffold protein range 20:1 to 100:1), egg phosphatidylcholine extracts and 1,2-bis(10,12-tricosadiynoyl)-sn-glycero-3-phosphocholine (ratio range 0.9:0.1 to 0.6:0.4) with MSP1E3D1 (lipid:scaffold protein range 20:1 to 100:1), 1,2-dierucoyl-sn-glycero-3-phosphocholine and 1,2-bis(10,12-tricosadiynoyl)-sn-glycero-3-phosphocholine (ratio range 0.9:0.1-0.6:0.4) with MSP1E3D1 (lipid:scaffold protein range 20:1 to 100:1), 1,2-dimyristoyl-sn-glycero-3-phosphocholine and 1,2-bis(10,12-tricosadiynoyl)-sn-glycero-3-phosphocholine (ratio range 0.9:0.1 to 0.6:0.4) with rat derived apoE322k (lipid:scaffold protein range 40:1 to 200:1), 1,2-dilauroyl-sn-glycero-3-phosphocholine and 1,2-bis(10,12-tricosadiynoyl)-sn-glycero-3-phosphocholine (ratio range 0.9:0.1-0.6:0.4) with rat derived apoE322k (lipid:scaffold protein range 40:1 to 200:1), 1-palmitoyl-2-oleoyl-sn-glycero-3-phosphocholine and 1,2-bis(10,12-tricosadiynoyl)-sn-glycero-3-phosphocholine (ratio range 0.9:0.1 to 0.6:0.4) with rat derived apoE322k (lipid:scaffold protein range 40:1-200:1), egg phosphatidylcholine extracts and 1,2-bis(10,12-tricosadiynoyl)-sn-glycero-3-phosphocholine (ratio range 0.9:0.1 to 0.6:0.4) with rat derived apoE322k (lipid:scaffold protein range 40:1 to 200:1), 1,2-dierucoyl-sn-glycero-3-phosphocholine and 1,2-bis(10,12-tricosadiynoyl)-sn-glycero-3-phosphocholine (ratio range 0.9:0.1 to 0.6:0.4) with rat derived apoE322k (lipid:scaffold protein range 40:1 to 200:1).

In embodiments, herein described NLPs can be prepared with various methods resulting in the assembly of the lipid component formed by the membrane forming lipid and the polymerizable lipids with the scaffold protein.

In particular, in some embodiments the NLP lipid component and scaffold protein component can be contacted to form an admixture for a time and under conditions allowing assembling of the NLP according to methods known or identifiable by a skilled person upon reading of the present disclosure.

For example in some embodiments, NLPs herein described can be assembled by a dialysis method, which is a self-assembly process involving detergent solubilization of lipids followed by detergent removal as described for example in [19-21]. A dialysis method typically involves solubilizing the membrane lipid component including the polymerizable lipid, in a detergent, such as sodium cholate, at detergent concentrations above the critical micelle concentration. The resulting lipid/detergent solution is then incubated to allow for dissolution of the scaffold protein and sufficient interaction between the scaffold protein and lipid mixture (e.g. for about 30 min). After the incubation period, the detergent is removed (e.g. through dialysis or rinsing with detergent binding beads) and the scaffold protein of choice is added at an appropriate lipid to apolipoprotein ratio that will allow for self-assembly as will be understood by a skilled person upon reading of the present disclosure. In particular, the NLP typically self-assemble during the detergent removal process.

An example of a detergent commonly used to prepared apolipoprotein-lipid complexes is sodium cholate.

In some embodiments, NLPs herein described can be assembled by temperature cycling method, where an admixture of lipid component and scaffold protein component forming the NLPs that is subjected to a temperature transition cycle in presence of a detergent such as the one described in [22-24]. In the temperature cycle, the temperature of the admixture is raised above and below the gel crystalline transition temperature of the membrane forming lipids. In particular, in accordance with an exemplary procedure the lipid component including membrane forming lipid and polymerizable lipid can be added to the scaffold protein at the desired lipid to scaffold protein ratio in buffer. After thoroughly mixing the components, the solution is placed through a temperature cycle the transitions the temperature of the mixture above and below the phase transition temperature of the lipid constituents. For example during the temperature cycle, the solution is maintained above the transition temperature for about 15 mins and then below the transition temperature for about 15 mins. This process is continued for from about 2-24 hrs. This temperature cycle results in the spontaneous self-assembly of the NLPs.

In some embodiments, NLPs herein described can be assembled by an in vitro translation method, where self-assembly of the NLPs can be achieved while the apolipoprotein or other scaffold protein is being translated from mRNA as described for example in [25-28]. In this process, expression system lysates are mixed with the lipid component of the NLP and plasmid DNA encoding the scaffold protein. The reaction can then be allowed to proceed until assembly occurs during apolipoprotein expression (e.g. for approximately 4-24 hrs). The apolipoprotein typically contain an affinity tag (e.g. His-tag) for subsequent purification of the self-assembled NLP from the lysate.

In general, assembly of NLPs can be accomplished with a wide range of ratios of total membrane forming lipids to scaffold proteins. NLPs with lipid to scaffold molar ratios of about 20:1 up to about 240:1 have been successful synthesized. A typical assembly uses a lipid to protein molar ratio of about 100:1.

In some embodiments herein described in the various methods to allow assembly the components are used at the following ratios: polymerizable lipid to membrane forming lipid ratio ranges from about 0 to about 0.4, the bilayer forming lipid to functional amphipathic compound ratio ranges from about 0.25 to about 0.999, functional amphipathic compound to membrane forming lipid ratio ranges from about 0.01 to about 0.75 and the lipid apolipoprotein to total lipid ranges from about 20 to about 240.

In some embodiments, the methods and systems herein described are performed at predefined lipid protein ratio, assembly conditions and/or with the use of preselected protein component and amphipathic lipid so to increase the yield, control the size of the resulting NLP and/or provide an NLP of pre-determined dimensions so to include a predetermined functional molecules. In some embodiments, the molar ratio of lipid component to scaffold protein component is 20:1, 30:1, 40:1, 50:1, 60:1, 70:1, 80:1, 90:1, 100:1, 110:1, 120:1, 130:1, 140:1, 150:1, 160:1, 170:1, 180:1, 190:1, 200:1, 210:1, 220:1, 230:1, and 240:1. In NLPs herein described, the lipid to scaffold protein component ratio can be determined on a case by case basis in view of the experimental design as will be understood by a skilled person.

In some embodiments, following assembly, NLPs comprising polymerizable lipids can be exposed to conditions that promote polymerization of corresponding functional groups within the membrane lipid bilayer (e.g. UV, heat, additional conditions identifiable by a skilled person) to provide the cross-linked polymerizable lipid within the membrane lipid bilayer.

In some embodiments, the assembled NLP can be exposed to UV at 254 nm for 1 to 40 minutes. During the UV exposure process, free radicals are generated, which promote cross-linking between adjacent diacetylene groups within the polymerizable lipids. In some embodiments NLPs comprise at least 20 mol % polymerizable lipid and are subjected to a UV exposure time of about 10 minutes. In some of those embodiments the resulting cross-linked NLPs have higher stability compared to non-cross-linked NLPs as assessed through immersion in 100% serum solutions at 37° C., and monitored through size-exclusion liquid chromatography or other suitable techniques as will be understood by a skilled person.

In some embodiments, the assembled NLP can be contacted with one or more initiators crosslinking agent to perform chemical crosslinking of polymerizable lipids within the membrane lipid bilayer using lipid-based cross-linking approaches [29, 30]. In several embodiments cross-linking can be performed by UV exposure for 1-60 min of cross linkable groups such as diacetylene, methacrylate, acryloyl, sorbyl ester, diene, vinyl and isocyano groups. Several of the cross linkable groups can also be activated for cross-linking by incubation with 5-30 mol % (relative to lipid) of AIBN with heating to 30-80° C. for 2-24 hrs.

In some embodiments herein described following cross-linking, a nanolipoprotein particle herein described comprises, a membrane forming lipid, a polymerized lipid and a scaffold protein. In particular in embodiments herein described one or more membrane forming lipid and one or more cross-linked polymerizable lipid are arranged in a membrane lipid bilayer stabilized by the scaffold protein and by the one or more polymerized lipids. More particularly, in some embodiments of nanolipoprotein herein described van der waals forces between adjacent lipids and scaffold protein, as well as covalent bonds between the polymerized membrane lipid, stabilize the membrane lipid bilayer of the nanolipoprotein. The resulting membrane lipid bilayer is a cross-linked membrane lipid bilayer in the sense of the disclosure as will be understood by a skilled person.

In several embodiments herein described, following crosslinking a nanolipoprotein comprises a cross-linked membrane lipid bilayer confined in a discoidal structure by a scaffold protein, with the cross-linked membrane lipid bilayer comprising one or more membrane forming lipids, and one or more a cross-linked polymerizable lipid.

Composition of an NLP can be detected by various techniques known in the art, such as high performance liquid chromatography (HPLC) serum stability, mass spectrometry, NMR spectra and elemental analysis could be used to define the composition of the particles and additional techniques identifiable by a skilled person In several embodiments herein described, cross-linked NLPs show an increased stability with respect to other non-cross-linked NLPs. Stability can be quantitated based on the half life of intact NLP when incubated at 37° C. in 100% serum. Size exclusion chromatography can separate out intact NLPs from its dissociated components and was used to measure the half life of the NLP as will be understood by a skilled person.

In some embodiments NLPs assembled with a lipid to scaffold ratio ranging from 20-200, with a membrane forming lipid ranging from 95 to 75% mol % ratio and polymerizable lipid ranging from 10 to 40% mol % ratio, if cross-linked for at least 10 min at 254 nm UV are expected to result in formation of NLPs that are stable for 24 hrs or more in 100% sera.

In some embodiment, the membrane lipid bilayer of nanolipoproteins herein described comprises one or more functionalized amphipathic compounds which provide an additional component of the NLP herein described.

The term "functionalized amphipathic compounds" in the sense of the disclosure indicate compound having a hydrophobic portion and a hydrophilic portions in a configuration where the hydrophobic portion anchor is capable to anchor the compound to the lipid bilayer of the NLP and the hydrophilic portion (typically consisting or comprising a hydrophilic functional group) presented on the NLP bilayer face following NLP assembly.

The term "present" as used herein with reference to a compound or functional group indicates attachment performed to maintain the chemical reactivity of the compound or functional group as attached. Accordingly, a functional group presented on an amphipathic compound, is able to perform under the appropriate conditions the one or more chemical reactions that chemically characterize the functional group.

The use of functionalized amphipathic compounds enables attachment of various peptides or other biologics to the surfaces of the lipid of the NLP that allows some desired target features to be obtained, such as stability, affinity for a target molecule, and the like. Non-limiting examples of functional groups presented on functionalized lpids include: chelated Ni atoms, azide, anhydride, alkynes, thiols, halogens, carboxy, amino, hydroxyl, and phosphate groups, and the like.

In some embodiments, the functional group on the functionalized amphipathic compound can be a reactive chemical groups (e.g. azide, chelated nickel, alkyne, and additional reactive chemical group identifiable by a skilled person), a biologically active compound (e.g. DNA, peptide, carbohydrate, and additional biologically active group identifiable by a skilled person) or a small molecule (e.g. cellular targeting compound, adjuvant, drug, and additional small molecules identifiable by a skilled person). In some embodiments the functionalized amphipathic compound is a functionalized lipid compound. Functional groups that enhance the lipid solubility are referred to as hydrophobic or lipophilic functional groups. Functional groups that lack the ability to either ionize or form hydrogen bonds tend to impart a measure of lipid solubility to a drug molecule. The functional group can be attached to the lipid polar head through covalent or ionic bonds and "weak bonds" such as dipole-dipole interactions, the London dispersion force and hydrogen bonding, preferably covalent. Moreover, functionalization of the lipid can involve hydrophobic quantum dots embedded into the lipid bilayer. The following article is incorporated by reference in its entirety: R. A. Sperling, and W. J. Parak. "Surface modification, functionalization and bioconjugation of colloidal inorganic nanoparticles". Phil. Trans. R. Soc. A 28 Mar. 2010 vol. 368 no. 1915 1333-1383.

In some embodiments, functionalized amphipathic compounds can comprise one or more of 1,2-dipalmitoyl-sn-glycero-3-phosphoethanolamine-N-(6-((folate)amino) hexanoyl), 1,2-dipalmitoyl-sn-glycero-3-phosphoethanolamine-N-(6-azidohexanoyl), 1,2-dipalmitoyl-sn-glycero-3-phosphoethanolamine-N-(succinyl), 1,2-dioleoyl-sn-glycero-3-phosphoethanolamine-N-(succinyl), 1,2-dipalmitoyl-sn-glycero-3-phosphoethanolamine-N-(glutaryl), 1,2-dioleoyl-sn-glycero-3-phosphoethanolamine-N-(glutaryl), 1,2-dioleoyl-sn-glycero-3-phosphoethanolamine-N-(dodecanyl), 1,2-Dipalmitoyl-sn-Glycero-3-Phosphoetha-nolamine-N-(hexanoyl amine), 1,2-dipalmitoyl-sn-glycero-3-phosphoethanolamine-N-(dodecanylamine), 1,2-Dipalmitoyl-sn-Glycero-3-Phosphothioethanol, 1,2-dioleoyl-sn-glycero-3-phosphoethanolamine-N-[4-(p-maleimidomethyl)cyclohexane-carboxamide], 1,2-dioleoyl-sn-glycero-3-phosphoethanolamine-N-[4-(p-maleimidophenyl)butyramide], 1,2-dioleoyl-sn-glycero-3-phosphoethanolamine-N-[3-(2-pyridyldithio)propionate], 1,2-dioleoyl-sn-glycero-3-phosphoethanolamine-N-(biotinyl), 1,2-Dioleoyl-sn-Glycero-3-Phospho(Ethylene Glycol), 1,2-dioleoyl-sn-glycero-3-phosphoethanolamine-N-lactosyl, 1,2-distearoyl-sn-glycero-3-phosphoethanolamine-N-[dibenzocyclooctyl(polyethylene glycol)-2000], 1,2-di stearoyl-sn-glycero-3-phosphoethanolamine-N-[succinyl (polyethylene glycol)-2000], 1,2-di stearoyl-sn-glycero-3-phosphoethanolamine-N-[carboxy(polyethyleneglycol)-2000], 1,2-distearoyl-sn-glycero-3-phosphoethanolamine-N-[maleimide(polyethylene glycol)-2000], 1,2-di stearoyl-sn-glycero-3-phosphoethanolamine-N-[PDP(polyethylene glycol)-2000], 1,2-di stearoyl-sn-glycero-3-phosphoethanolamine-N-[amino(polyethylene glycol)-2000], 1,2-di stearoyl-sn-glycero-3-phosphoethanolamine-N-[biotinyl (polyethylene glycol)-2000], 1,2-distearoyl-sn-glycero-3-phosphoethanolamine-N-[cyanur(polyethylene glycol)-2000], 1,2-di stearoyl-sn-glycero-3-phosphoethanolamine-N-[folate(polyethylene glycol)-2000], cholesterol modified oligonucleotides, cholesterol-PEG2000-azide, cholesterol-PEG2000-Dibenzocyclooctyl, cholesterol-PEG2000-maleimide, cholesterol-PEG2000-N-hydroxysuccinimide esters, cholesterol-PEG2000-thiol, cholesterol-azide, cholesterol-Dibenzocyclooctyl, cholesterol-maleimide, cholesterol-N-hydroxysuccinimide esters, cholesterol-thiol, C18 modified oligonucleotides, C18-PEG2000-azide, C18-PEG2000-Dibenzocyclooctyl, C18-PEG2000-maleimide, C18-PEG2000-N-hydroxysuccinimide esters, C18-PEG2000-thiol, C18-azide, C18-Dibenzocyclooctyl, C18-maleimide, C18-N-hydroxysuccinimide esters, C18-thiol.

In some embodiments one or more functionalized amphipathic compounds are comprised together with non-functionalized membrane forming lipids in the lipid component of the NLP also comprising one or more polymerizable lipids. In some embodiments functionalized amphipathic compounds can be functionalized membrane forming lipid. In some embodiments, one or more functionalized membrane forming lipids are added or replace the membrane forming lipids in the lipid component of the NLP herein described also comprising one or more polymerizable lipids.

In particular, the ratio between functionalized membrane forming lipid and membrane forming lipids is dependent on the identity of the functionalized membrane forming lipid, and it can be as low as 1% or even lower and as high as 100% as NLPs have been successfully formed with 100% functionalized membrane forming lipid such as DOGS-NTA-Ni (1,2-di-(9Z-octadecenoyl)-sn-glycero-3-[(N-(5-amino-1-carboxypentyl)iminodiacetic acid)succinyl] (nickel salt)). This suggests that NLPs can be formed with any percentage of functionalized membrane forming lipid (from 0 to 100%), depending on the specific functionalized membrane forming lipid used.

In some embodiments, the ratio of functionalized amphipathic compounds can vary from 0.1 mol % to 95 mol % (relative to polymerizable lipid) depending on the functionalized amphipathic compounds. Functionalized amphipathic compounds that are lipids themselves, such as DOGS-NTA-Ni (1,2-di-(9Z-octadecenoyl)-sn-glycero-3-[(N-(5-amino-1-carboxypentyl)iminodiacetic acid)succinyl] (nickel salt)) can be used at 95 mol %, with polymerizable lipid comprising at least 5 mol %. A preferred molar ratio of DOGS-NTA-Ni:polymerizable lipid:membrane forming lipid is 35:20:45. In contrast, functional amphipathic compounds that are less lipid like, such as cholesterol modified oligonucleotides, a lower mol % (0.1-10 mol %) is needed for successful NLP assembly.

In some embodiments, the nanolipoprotein particles herein described can further comprise other functional molecules embedded in the membrane lipid bilayer (e.g. interacting with the membrane lipid bilayer components through van der waals forces), conjugated to a lipophilic anchor compound inserted into the membrane lipid bilayer (e.g. through hydrophobic-hydrophilic interactions) or conjugated through binding of a functional group with a corresponding functional group presented on functionalized membrane forming lipid of the membrane lipid bilayer. In some of those embodiments, the other functional molecules comprise small molecules and in particular cyclic or non-cyclic peptides and can be comprised in the NLP here described in an amount that varies from case to case, and that in general can range from 0.1-10 mol %.

In some embodiments, the nanolipoprotein particles herein described can further comprise one or more membrane proteins herein. The term "membrane protein" as used herein indicates any protein having a structure that is suitable for attachment to or association with a biological membrane or biomembrane (i.e. an enclosing or separating amphipathic layer that acts as a barrier within or around a cell). In particular, membrane proteins include proteins that contain large regions or structural domains that are hydrophobic (the regions that are embedded in or bound to the membrane); those proteins can be difficult to work with in aqueous systems, since when removed from their normal lipid bilayer environment those proteins tend to aggregate and become insoluble.

Exemplary methods to provide nanolipoprotein particles which are expected to be applicable to provide one or more NLPs presenting one or more membrane proteins, comprise the methods described in U.S. Patent Publication No. 2009/0192299 related to methods and systems for assembling, solubilizing and/or purifying a membrane associated protein in a nanolipoprotein particle, which comprise a temperature transition cycle performed in presence of a detergent, wherein during the temperature transition cycle the nanolipoprotein components are brought to a temperature above and below the gel to liquid crystallization transition temperature of the membrane forming lipid of the nanolipoprotein particle. In some embodiments, verification of inclusion of a membrane proteins can be performed using the methods and systems for monitoring production of a target protein in a nanolipoprotein particle described in U.S. Patent Publication No. 2009/0136937 filed on May 9, 2008 with Ser. No. 12/118,530 which is incorporated by reference in its entirety.

In particular, in several embodiments any one of the nanolipoprotein particle herein described further comprises an active target molecule, such as an immunogen, a drug, a contrast agent or another molecule of interest, comprised as a membrane protein or as an active target molecule attached to functionalized amphipathic compounds in the membrane lipid bilayer, in a configuration resulting having the active target molecule presented on the nanolipoprotein particle. The active target molecule can be a target protein having a hydrophobic region, and be presented on the nanolipoprotein particle attached to the membrane lipid bilayer through interaction of the target protein hydrophobic region with the membrane lipid bilayer. In addition or in the alternative the active target molecule can be an active target molecule presented on the nanolipoprotein particle attached to one or more functionalized membrane forming lipid through anchor compounds as described in U.S. Pat. No. 8,883,729 issued on Nov. 11, 2014 and in U.S. Pat. No. 8,889,623 issued on Nov. 18, 2014 each of which is incorporated by reference in its entirety.

In several embodiments, cross-linked NLPs herein described can be used in various applications wherein stability of NLPs is desired.

In some embodiments, cross-linked NLPs herein described can used in biomedical applications, including drug delivery [31-33] [34], in particular when improved pharmacokinetic is desired [35, 36], diagnostic imaging [37], and vaccine and immunomodulation applications [38-41]. In particular, some embodiments, the methods described in this application improve the stability under these conditions by three orders of magnitude with half-lives on the order of 24-48 hrs. Accordingly, nanoparticle-mediated drug delivery performed with NLPs herein described is expected to address several limitations of conventional drug delivery systems, including nonspecific biodistribution, low water solubility, poor oral bioavailability, and low therapeutic indices [42].

In some embodiments, methods to deliver one or more compounds such as a target molecule and/or/or an active agent to a target cell or tissue in an individual can comprise administering to the individaul one or more cross-linked NLPs herein described presenting the one or more compounds, the administering performed to allow contacting the one or more cross-linked NLPs presenting the one or more compounds with the target cell or tissue in the individual.

In particular, compounds that can be delivered with crosslinked NLPs herein described encompass compounds of various chemical nature and dimensions which can be presented on the NLPs through attachment to various moieties and components of the NLPs such as the lipid of the membrane lipid bilayer or target proteins embedded therein. In particular, one or more compounds can be wholly contained in the lipid bilayer, partially anchored in the lipid bilayer, or conjugated to the lipid bilayer surface of NLPs herein described as will be understood by a skilled person upon reading of the present disclosure.

The term "individual" as used herein includes a single biological organism can occur including but not limited to animals and in particular higher animals more particularly vertebrates such as mammals and in particular human beings.

In some embodiments, the delivery of a compound can be performed for medical imaging application (e.g. delivery of a contrast agent to a target tissue of the individual to be imaged). In some embodiments, the delivery of a compound with NLPs herein described can be performed to treat or prevent a condition in the individual.

The term "condition" indicates a physical status of the body of an individual (as a whole or as one or more of its parts e.g., body systems), that does not conform to a standard physical status associated with a state of complete physical, mental and social well-being for the individual. Conditions herein described comprise disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms in an individual.

The term "treatment" as used herein indicates any activity that is part of a medical care for, or deals with, a condition, medically or surgically. The terms "treating" and "treatment" refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a symptom or adverse physiological event in a susceptible individual, as well as modulation and/or amelioration of the status of a clinically symptomatic individual by inhibiting or causing regression of a disorder or disease.

The term "prevention" as used herein with reference to a condition indicates any activity which reduces the burden of mortality or morbidity from the condition in an individual.

In methods herein described, administering NLPs to an individual can be performed by topical or systemic administration. The wording "topical administration" as used herein relates to a route of administration wherein the active agent usually included in a NLP herein described within an appropriate formulation directly where its action is desired. Exemplary topical administration comprises epicutaneous administration, inhalational administration (e.g., in asthma medications), enema, eye drops (e.g., onto the conjunctiva), ear drops, intranasal route (e.g., decongestant nasal sprays), and vaginal administration, rectal administration and oral administration of non-absorbed agents.

The wording "systemic administration" as used herein indicates a route of administration by which an active agent is brought in contact with the body of the individual, so that the desired effect is systemic (i.e. non limited to the specific tissue where the infection and/or inflammation occurs). In particular, in embodiments herein described the administration of crosslinked NLPs can be performed by parenteral administration, a systemic route of administration where a substance is given by a route other than the digestive tract and includes but is not limited to intravenous administration, intra-arterial administration, intramuscular administration, subcutaneous administration, intradermal, administration, intraperitoneal administration, and intravesical infusion.

In some embodiments, administration is performed intravenously by introducing a liquid formulation including one or more NLPs herein described in a vein of an individual using intravenous access methods identifiable by a skilled person, including access through the skin into a peripheral vein. In some embodiments, administration of a NLP herein described is performed intraperitoneally, by injecting a NLP in the peritoneum of an individual, and in particular of animals or humans. Intraperitoneal administration is generally preferred when large amounts of blood replacement fluids are needed, or when low blood pressure or other problems prevent the use of a suitable blood vessel for intravenous injection.

In some embodiments, cross-linked NLPs herein described can used in in vitro drug screening applications, e.g. for incorporation and solubilization of membrane proteins, for high throughput screening of drug compounds [43, 44] as well as phage display selection [45].

In particular in some embodiments, methods and systems are described to screen a test compound (e.g. a test active agent) for one or more biological activities associated to an interaction of the test compound with a target compound or cell, the method comprising contacting a crosslinked NLPs herein described presenting the test compound, with the target compound or cell for a time and under conditions to allow detection of the one or more biological activities following the contacting, thus providing one or more detected biological activities for the test compound. In some embodiments the method further comprises selecting the test compound having a desired one or more detected biological activities. In some embodiments the test compound comprises one or more test compounds and the target compound or cell comprises one or more target compounds Biological activities that can be screened with methods and systems herein described comprise ability of the one or more test compounds to bind the one or more target compounds or cells, the affinity of test compounds for the one or more target compounds or cells, selectivity of the test compounds for the one or more target compounds or cells, ability of the test compounds to inhibit or stimulate the one or more target compounds or cells (e.g. acting as antagonists or agonists). In some embodiments, screening of the above biological activities can be performed to identify properties of the one or more test compounds associated to their use as drugs, such as metabolic stability (e.g. to increase the half-life of the drug), oral bioavailability (in connection with administration of the) or toxicity (e.g. to reduce the potential of side effects of the drug). In some embodiments, crosslinked NLPs herein described can used in sensor applications, such as on-chip immunoassays [46, 47], evaluation of enzyme kinetics [48] and to monitor lipid-membrane mediated biorecognition reactions [49].

In some embodiments, NLP composition can be customized through apolipoprotein and lipid choice [50, 51] and composition and self-assembly protocols optimized to solubilize membrane proteins,[52-58] protein pore complexes, [59] or hydrophobic drugs [60-62]. Thus, due to the versatility in assembly components, NLPs can be tailor-made for a variety of applications, including targeted drug delivery, antigen delivery,[20, 63] and immune stimulation [51] as will be understood by a skilled person.

In some embodiments, an NLP can be included in pharmaceutical compositions (e.g. a vaccine) together with an excipient or diluent. In particular, in some embodiments, pharmaceutical compositions are disclosed which contain NLP, in combination with one or more compatible and pharmaceutically acceptable vehicle, and in particular with pharmaceutically acceptable diluents or excipients.

The term "excipient" as used herein indicates an inactive substance used as a carrier for the active ingredients of a medication. Suitable excipients for the pharmaceutical compositions herein disclosed include any substance that enhances the ability of the body of an individual to absorb the NLP. Suitable excipients also include any substance that can be used to bulk up formulations with NLP to allow for convenient and accurate dosage. In addition to their use in the single-dosage quantity, excipients can be used in the manufacturing process to aid in the handling of NLP. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluent include any substance that can decrease the viscosity of a medicinal preparation.

In certain embodiments, compositions and, in particular, pharmaceutical compositions can be formulated for systemic administration, which includes parenteral administration and more particularly intravenous, intradermic, and intramuscular administration. In some embodiments, compositions and, in particular, pharmaceutical compositions can be formulated for non-parenteral administration and more particularly intranasal, intratracheal, vaginal, oral, and sublingual administration.

Exemplary compositions for parenteral administration include but are not limited to sterile aqueous solutions, injectable solutions or suspensions including NLP. In some embodiments, a composition for parenteral administration can be prepared at the time of use by dissolving a powdered composition, previously prepared in a freeze-dried lyophilized form, in a biologically compatible aqueous liquid (distilled water, physiological solution or other aqueous solution).

The term "lyophilization" (also known as freeze-drying or cryodesiccation) indicates a dehydration process typically used to preserve a perishable material or make the material more convenient for transport. Freeze-drying works by freezing the material and then reducing the surrounding pressure and adding enough heat to allow the frozen water in the material to sublime directly from the solid phase to gas.

If a freeze-dried substance is sealed to prevent the reabsorption of moisture, the substance may be stored at room temperature without refrigeration, and be protected against spoilage for many years. Preservation is possible because the greatly reduced water content inhibits the action of microorganisms and enzymes that would normally spoil or degrade the substance.

Lyophilization can also causes less damage to the substance than other dehydration methods using higher temperatures. Freeze-drying does not usually cause shrinkage or toughening of the material being dried. In addition, flavours and smells generally remain unchanged, making the process popular for preserving food. However, water is not the only chemical capable of sublimation, and the loss of other volatile compounds such as acetic acid (vinegar) and alcohols can yield undesirable results.

Freeze-dried products can be rehydrated (reconstituted) much more quickly and easily because the process leaves microscopic pores. The pores are created by the ice crystals that sublimate, leaving gaps or pores in their place. This is especially important when it comes to pharmaceutical uses. Lyophilization can also be used to increase the shelf life of some pharmaceuticals for many years.

In pharmaceutical applications freeze-drying is often used to increase the shelf life of products, such as vaccines and other injectables. By removing the water from the material and sealing the material in a vial, the material can be easily stored, shipped, and later reconstituted to its original form for injection In some embodiments, NLPs herein described and related components can be provided as a part of systems in accordance to various embodiments herein described.

In some embodiments, the systems herein described can be provided in the form of kits of parts. In a kit of parts, membrane forming lipid, polymerizable lipids, crosslinking agents, target molecule, active agent, target cell, target compounds and/or NLPs can be provided in various combinations one with another and with, one or more functionalized amphipathic compounds, one or more membrane protein, and/or scaffold proteins or fragments thereof. In the kits of parts the components can be comprised in the kit independently possibly included in a composition together with suitable vehicle carrier or auxiliary agents.

Additional components can also be included and comprise, reference standards, and additional components identifiable by a skilled person upon reading of the present disclosure.

In the kit of parts herein disclosed, the components of the kit can be provided, with suitable instructions and other necessary reagents, in order to perform the methods here disclosed. In some embodiments, the kit can contain the compositions in separate containers. Instructions, for example written or audio instructions, on paper or electronic support such as tapes or CD-ROMs, for carrying out the assay, can also be included in the kit. The kit can also contain, depending on the particular method used, other packaged reagents and materials (i.e. wash buffers and the like).

In some embodiments, kit of parts herein described comprise components selected to perform delivery and/or screening of compounds (e.g. drugs and/or contrast agents) according to methods herein described. In some embodiments kit of parts comprise components selected to perform sensor applications or other applications herein described.

Further details concerning the identification of the suitable carrier agent or auxiliary agent of the compositions, and generally manufacturing and packaging of the kit, can be identified by the person skilled in the art upon reading of the present disclosure.

EXAMPLES

The methods and system herein disclosed are further illustrated in the following examples, which are provided by way of illustration and are not intended to be limiting.

In particular, NLPs comprising various membrane forming lipids and photopolymerizable lipid, DiynePC were prepared and tested in vitro and in vivo.

The related experiments were carried out in both cell culture media containing 10% and 100% FBS to simulate in vitro (cell culture) and in vivo conditions, respectively. The primary parameters tested in terms of acyl chain composition were the length of the acyl chain (16-22 carbons) and the number of double bonds per chain (from 0 to 2). Since natural HDLs contain a complex mixture of different lipid types including cholesterol, the stability of NLPs assembled with cholesterol and/or natural derived lipid extracts (EggPC and SoyPC) was examined. In addition, the effects of crosslinking the NLP bilayer were also explored using photopolymerizable lipids. To further assess the effects of stability with regards to in vivo delivery applications, the effect of crosslinking on cellular uptake in vitro and particle stability in vivo was examined. The following materials and methods were used Materials:

1,2-dipalmitoleoyl-sn-glycero-3-phosphocholine (16:1), 1,2-dioleoyl-sn-glycero-3-phosphocholine (DOPC/18:1), 1,2-dieicosenoyl-sn-glycero-3-phosphocholine (20:1), 1,2-dierucoyl-sn-glycero-3-phosphocholine (22:1), 1,2-dimyristoyl-sn-glycero-3-phosphocholine (DMPC/14:0), 1,2-dipalmitoyl-sn-glycero-3-phosphocholine (DPPC/16:0), 1,2-dilinoleoyl-sn-glycero-3-phosphocholine (14:1), (SoyPC), (EggPC), cholesterol, and 1,2-bis(10,12-tricosadiynoyl)-sn-glycero-3-phosphocholine (DiynePC) were purchased from Avanti Polar Lipids (Alabaster, AL). All other reagents were ordered from Sigma-Aldrich (St. Louis, MO). RPMI-1640 was purchased from ATCC. Fetal bovine serum, Penicillin/Streptomycin, and Alexa Fluor 488 NHS Ester (AF488) were obtained from Invitrogen (Carlsbad, CA).

Protein Expression and Purification;

The Expression Clone for the 22 kDa N-terminal fragment of human apolipoprotein E4 (apoE422k, kindly provided by Dr. Karl Weisgraber) featuring a cleavable His-tag [64] was expressed and purified as previously described.[22, 65]

NLP Assemblies

NLPs were assembled according to a previously reported procedure,[22, 65] with slight modifications. For each new lipid or lipid mixture, a lipid to protein ratio was found in order to minimize excess protein following the reaction and to attempt to consolidate the NLPs into a single size population as determined by SEC. These ratios are given in Table 1 below. Briefly, lipids were either prepared or obtained in chloroform and aliquoted into glass vials. Chloroform was then removed using a stream of $N_2$ under agitation to form a thin lipid film. Lipids were solubilized in PBS buffer (137 mM sodium chloride, 2.7 mM potassium chloride, 10 mM phosphate buffer, pH 7.4) using 80 mM sodium cholate. After addition of the apoE422k (150 µM in final assembly volume), samples were incubated at 22° C. for at least 1 hour. Assemblies with DiynePC were heated to 37° C. for 30 minutes and then cooled to 22° C. for thirty minutes after the lipids were dried down in order to fully solubilize the solution. Assemblies were dialyzed overnight against PBS to remove cholate.

TABLE 1

| Lipid | Lipid:Protein | Reaction temperature |
|---|---|---|
| DPOPC | 120:1 | 22° C. |
| DOPC | 100:1 | 22° C. |
| DEIPC | 80:1 | 22° C. |
| DERPC | 80:1 | 22° C. |
| DLOPC | 90:1 | 22° C. |
| SoyPC | 80:1 | 22° C. |
| EggPC | 80:1 | 22° C. |
| 90% DOPC, 10% cholesterol | 80:1 | 22° C. |
| 20% DiynePC, 80% DOPC | 80:1 | Mix 37° C. for 30 minutes, 22° C. |

Labeling the NLPs with Alexa Fluor Dyes.

NLPs were labeled with either AF488 by incubating the NLPs with the reactive dye for at least 2 hrs (5:1 dye:NLP molar ratio). The reaction was performed in PBS buffer containing 5 mM sodium bicarbonate, pH 8.2. After completion of the reaction, 10 mM Tris pH 8.0 was added to quench any unreacted dye and incubated for 30 minutes. Free dye in the NLP solution was removed by using a dye-removal column kit, as directed (Thermo Fisher, Rockford, IL).

NLP Purification

Samples were subsequently analyzed and purified by SEC (Superdex 200, 10/300 GL column, GE Healthcare, Piscataway, NJ) in PBS buffer (0.5 mL/min flow rate). The exclusion limit of the column was determined with Blue Dextran 2000. SEC fractions (500 µl) were collected every 60 s. SEC fractions containing homogeneous NLP populations were concentrated using 50 kDa MWCO spin concentrators (Sartorius). A concentration for NLPs in solution was determined by using a Nanodrop ND-1000 spectrophotometer (ThermoScientific, Lafayette, CO) at an absorbance of 280 nm. The concentrated NLP samples were then stored at 4° C. until further use. In these experiments, the NLP concentration was calculated based on the apoE422k concentration by assuming that each NLP contained 6 apoE422k scaffold proteins.[19, 65]

Polymerization of NLPs Containing DiynePC

NLPs that contained DiynePC were treated with UV-C following purification. NLP solutions in polypropylene tubes were placed in a Stratalinker 2400 UV crosslinker (Stratagene, La Jolla, CA) and exposed to 254 nm light for the specified time.

SEC Analysis of NLP Stability in Complex Biological Fluids

NLP samples were incubated in FBS and 10% FBS in RPMI-1640 and subsequently analyzed by SEC (Superdex 200 PC 3.2/30 column, GE Healthcare) in PBS buffer. A flow rate of 0.1 ml/min was used to ensure no overlap in the elution of disassembled apoE422k and intact NLP. The NLPs labeled with AF488 were monitored using a RF-20 fluorescence detector (Shimadzu) set to excite at 497 nm and to measure fluorescence at 520 nm to avoid interfering absorbance from serum proteins and constituents. The raw chromatograph obtained from the fluorescence detector was further analyzed by fitting a series of Gaussian functions to the trace through code written in Python using the lmfit library. Peaks centered between 9 and 14 minutes were considered to be NLP populations, while free apoE422k was found to elute at approximately 17.5 minutes under these conditions. The NLP Gaussian functions were then integrated to assess NLP disassembly as a function of time. These peak areas, from independent samples incubated in media or serum for varying times, were then arranged into a time series, and exponential decay functions were fit to each combination of peak areas. For each fit, the function was normalized around time zero, and the half-life of the function was recorded. Extreme outliers were then discarded.

Particle Size Measurements Using Dynamic Light Scattering.

Purified NLP solutions were diluted to approximately 0.2 mg/ml. The size distribution of the particles was analyzed using a Zetatrac (Microtrac). Each sample was analyzed three times in sequence to obtain an average measurement. The analysis chamber was rinsed with DI water between samples.

Culture of Human Bladder Cancer Type II Carcinoma Cells

Human bladder cancer cells were obtained from ATCC (#5637). Cells were grown in T-75 vented tissue culture flasks in RPMI-1640 with 1% Penicillin/Streptomycin and 10% FBS. Cells were incubated at 37° C. and 5% $CO_2$ until confluent. Cells were then removed from the flasks using Trypsin and plated into 24 well plates for dosing experiments. Cells were allowed to grow to confluence prior to dosing experiments.

NLP Uptake into Human Bladder Cancer Cells.

Prior to dosing, cells were placed into new media for one hour prior to dosing with NLPs. Fluorescently labelled NLPs (2.5 micrograms) were then pipetted into the wells and the cells were returned to the incubator following the completion of dosing. To measure the uptake at various time points, cells were removed from the wells using trypsin, and then spun down at 4 k RPM for five minutes. The supernatant was discarded and the cells were resuspended in 0.5 ml of PBS using a pipette to disrupt the cell pellet. The cell suspension was analyzed using a FACScalibur (Becton Dickinson, Franklin Lakes, NJ). The mean fluorescence intensity was obtained for the population of cells.

Example 1: Determination of NLP Stability by Analytical Size Exclusion Chromatography The effect of adding a photopolymerizable lipid, DiynePC, to the NLP assembly to facilitate lipid cross-linking was evaluated. DiynePC is a phospholipid bearing reactive diacetylene groups on each acyl chain. When exposed to UV (254 nm) light, adjacent diacetylene moieties polymerize, resulting in intermolecular crosslinking within the lipid bilayer.

In a series of experiments illustrated herein, the ability of DiynePC to enhance NLP stability was assessed using DOPC-based (18:1 PC) NLPs, due to the relative stability of the DOPC NLPs as well as their documented low immunogenicity and toxicity [66] [34].

Analytical size exclusion chromatography (aSEC) was used to evaluate the stability of cross-linked and non cross-linked DOPC based NLPs. For these experiments, NLPs were labeled with AF488 via lysines on the apolipoprotein. Elution of the labeled scaffold protein through the analytical column was monitored by fluorescence detection (Excitation—497 nm, Emission—520 nm). This approach provided a spectrofluorometric signature unique to the apolipoprotein (and thus the NLP) that was negligibly perturbed by the presence of other constituents that typically preclude optical absorbance monitoring under these experimental conditions. The large difference in size (and hence retention time, tr) between the NLP and unbound apolipoproteins provides convenient interrogation of NLP integrity by analyzing the fraction of intact NLPs (tr ~9-14 min) versus unbound apolipoprotein released upon NLP dissociation (tr ~17.5 min). Representative aSEC chromatograms of intact and dissociated NLPs are shown in FIG. 1

The data reported in the illustration of FIG. 1 show that dissociation of the NLPs clearly results in a substantially reduced peak area at elution times associated with intact NLP, and the peak consistent with unbound E4 predominates. These analytical protocols were used to assess the solution half-life ($t_{1/2}$) of each NLP formulation under in vitro and in vivo conditions (10% FBS and 100% FBS at 37° C., respectively) according to an assay exemplified in Example 2.

Example 2: Assay to Assess Stability of NLPs In Vitro

To assess the stability of NLPs under conditions that mimic in vitro conditions, NLPs were incubated in media supplemented with 10% serum at 37° C. for various timepoints and the half-life of the NLP was measured based on the SEC profile. These conditions were selected as an in vitro mimic because most culture conditions involve cell media supplemented with 10% sera and incubation at 37° C. To assess the stability of NLPs under conditions that mimic in vivo conditions, NLPs were incubated in 100% serum at 37° C. for various timepoints and the half-life was measured based on the SEC profile. These conditions were selected as an in vivo mimic of intravenous administration of the NLP. Since >50% of the blood is sera, these conditions actually represent the most extreme in vivo condition.

In particular 100% serum condition closely mimics the environment the platform would encounter if used in medical applications.

Figure 2:
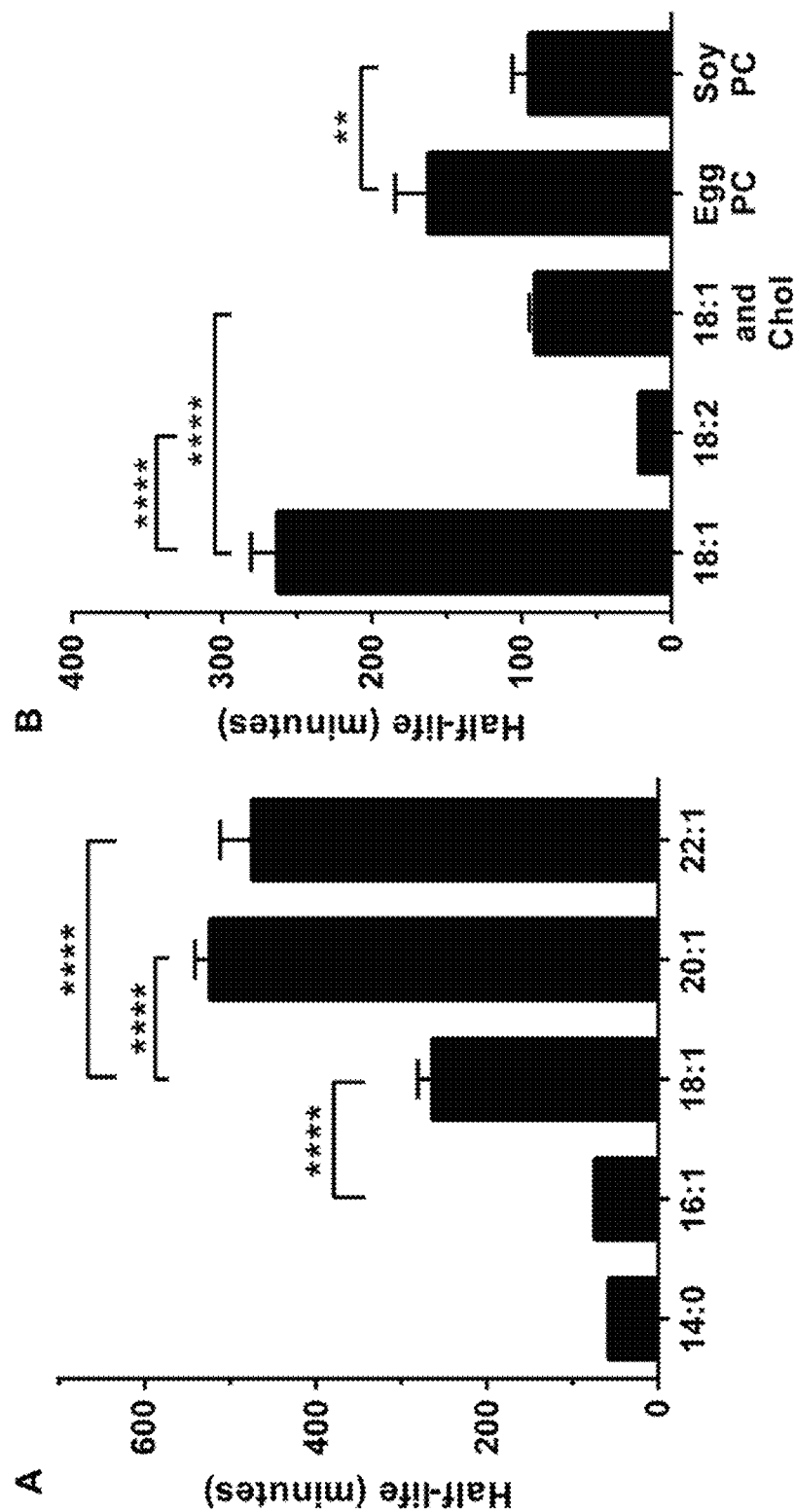
FIG. 2 shows results of experiments measuring half-lives in cell media with 10% FBS at 37° C. for NLPs with different lipid formulations.

Example 3: Effect of Chain Length, Acyl Chain Double Bonds and Natural Derived Lipid Extracts on NLP Stability in Cell Culture Media Containing 10% FBS To assess the effect of chain length on NLP stability, NLPs were formed with mono-unsaturated lipids (16:1, 18:1, 20:1 and 22:1 PC) of varying length and incubated in 10% serum at 37° C. for various time points prior to aSEC analysis. Interestingly, the NLP $t_{1/2}$ increased with an increase in acyl chain length from 16:1 (74±1 minutes) to 20:1 (523±18 minutes, $P=7.9\times10^{-40}$); however, a further increase in acyl chain length (22:1 PC) provided no significant increase in NLP $t_{1/2}$ (FIG. 2A, P=0.69).

Lipids with shorter acyl chains (14:1 PC) formed NLPs that were very unstable even in PBS at 4° C. and it was not possible to quantify the $t_{1/2}$ of these particles. In addition, while NLPs were reliably assembled using 14:0 PC (DMPC) [34], lipid solubility was a significant obstacle in NLP formation with longer saturated acyl chains. 16:0 PC and 18:0 PC both required higher cholate concentrations (60 mM) and elevated temperatures (up to 41° C. and 48° C., respectively) to achieve clear lipid solutions in PBS. Furthermore, even when elevated temperatures were used during dialysis to prevent lipid precipitation, the assembly products resembled large protein/lipid aggregates rather than NLPs, as evidenced by a significantly reduced $t_r$ corresponding to the column void volume.

To examine the effect of lipid chain unsaturation on NLP stability, a lipid with two double bonds per acyl chain (18:2 PC) was used to synthesize NLPs. In these experiments, 18:2 PC NLPs were found to be far less stable in media with 10% serum than 18:1 PC NLPs (FIG. 2B).

In order to more accurately mimic the lipid composition of natural HDLs, the stability of NLPs assembled with natural derived lipid extracts (EggPC and SoyPC) and a cholesterol/18:1 PC mixture (10% cholesterol and 90% 18:1 PC) was assessed. As shown in FIG. 2B, EggPC and SoyPC yielded particles with lower stability than 18:1 PC NLPs (162±21 minutes, P=0.0000013; 95±11 minutes, $P=2.9\times10^{-16}$). Interestingly, the SoyPC composition is more heavily dominated by 18:2 PC lipids than EggPC (60% vs. 20%, respectively) (per the manufacturer, Avanti), which may explain the lower stability of the SoyPC NLPs.

In 10% FBS, the lipid acyl chain structure was found to have a significant impact on NLP stability where an increase in acyl chain length provided an increase in stability up to a chain length of 22:1. In contrast, a decrease in NLP stability was observed when a single double bond was present in the acyl chain and a further decrease was observed when two double bounds were present in the acyl chain. It has previously been reported that poly-cis unsaturated lipids form thinner and more elastic membranes than mono-unsaturated lipids.[67] According to the polymer brush model [67], these unsaturations have the effect of reducing the persistence length [68] of the acyl chain, which in turn may lead to increased inter-lipid repulsion. These differences in mechanical properties, and the possibility of increased inter-lipid repulsion due to double bonds in the acyl chain, could be responsible for the decrease in NLP stability.

When the stability of NLPs assembled with lipid extracts was evaluated, a significant decrease was observed in the stability of the SoyPC NLPs relative to the EggPC NLPs, which was likely due to the higher amount of the 18:2 NLPs in the SoyPC extract. Similarly, addition of cholesterol during 18:1 PC NLP assembly resulted in decreased particle stability in 10% serum. These results are consistent with a previous study describing the relative lysis tension of giant unilamellar vesicles (GUVs) consisting of various lipid mixtures, indicating that 18:1 PC GUVs are less stable when prepared with 17% cholesterol.[69]

However, the contribution of cholesterol can be dependent on both the lipid structure and scaffold protein as others have synthesized rHDLs with cholesterol,[70].

Example 4: Effect of Composition Chain Length, Unsaturation on NLP Stability in 100% FBS The experimental procedures illustrated in Example 3 were performed in 100% FBS to determine stability of NLPs having various compositions chain length and unsaturation of the lipid component in 100% FBS.

Surprisingly, these same trends in NLP stability observed at 10% FBS conditions were not observed when the experiments were performed in 100% sera and all particle formulations were found to decompose within minutes.

Figure 3:
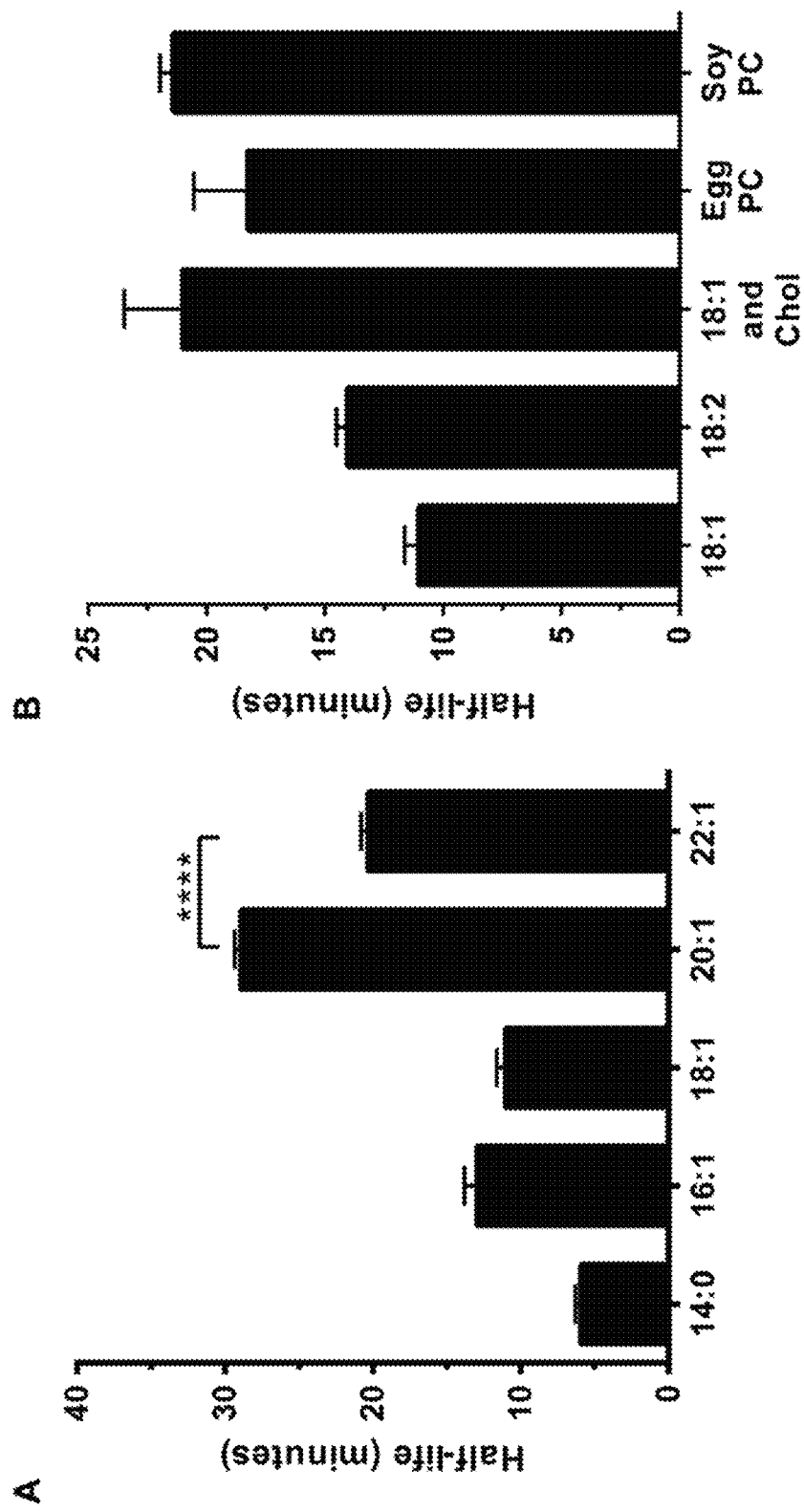
FIG. 3 shows diagrams illustrating results of experiments measuring half-lives in 100% FBS at 37° C. for NLPs with different lipid formulations.

In particular, when the stability of the NLPs in 100% sera were analyzed, a drastic reduction in NLP half-lives was observed regardless of lipid composition as illustrated in FIG. 3A and FIG. 3B, which is consistent with previous reports [34]. NLPs prepared with monounsaturated lipids exhibited half-lives ranging from 10-30 minutes (FIG. 3A), which was significantly lower than the maximum $t_{1/2}$ of 500 minutes observed in 10% serum (11±1 minutes versus 290±21 minutes for 18:1, p<0.001) Consistent with the stability results at lower serum concentrations, the 20:1 acyl chain structure displayed the greatest stability with a particle half-life of approximately 30 minutes (29±1 versus 20±1 for 22:1, p<0.0001).

The difference in stability between 10% FBS and 100% FBS suggests that components within the serum are responsible for the loss of stability, and an increase in the number of these components, such as serum proteins, electrolytes, serum lipids, and metabolites, significantly increases the rate at which particle dissociation occurs. These findings are in stark contrast to the previous studies where HDL mimics were reported to have in vivo circulation half-lives greater than 10 hrs. These previous studies evaluated the circulation times of only one component of the HDL mimetic, the apolipoprotein, and stability of the intact particle was not assessed. The results illustrated in the present disclosure suggest that care should be taken when assessing the stability of NLPs and other HDL mimetics when only one component of the complex is analyzed. In particular, it is apparent from the results of the disclosure studies that only track particle components may not yield results that are accurate as no information on particle integrity is collected. This may generate false positives for particles with consequences on the reliability of the data and related intended use. For example, particle prepared for drug delivery purposes and tested only tracking particle components may in fact be unable to be used for these purposes as the particles are actually too unstable.

Example 5: Effect of Polymerizable Lipids on NLP Stability in 100% FBS

Due to the low inherent stability of the NLP in 100% serum, the effect of incorporating lipids with photo-polymerizable groups in the acyl chain on NLP stability (X-NLPs) was evaluated.

In particular, the effect of adding a photopolymerizable lipid, DiynePC, to the NLP assembly to facilitate lipid cross-linking [12, 71] were evaluated. As also indicated in Example 1, DiynePC is a phospholipid bearing reactive diacetylene groups on each acyl chain. When exposed to UV (254 nm) light, adjacent diacetylene moieties polymerize, resulting in intermolecular crosslinking within the lipid bilayer.

Figure 4:
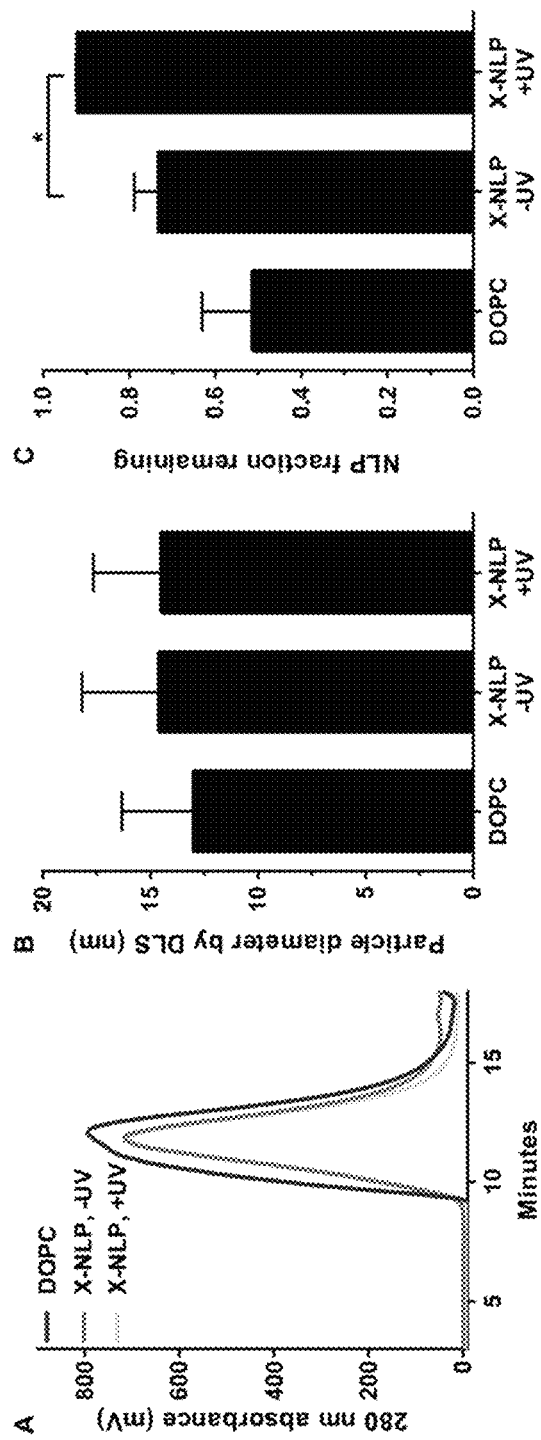
FIG. 4 shows diagrams illustrating results of experiments directed to perform characterization of NLPs synthesized with DiynePC.

In experiments exemplified in this disclosure, the ability of DiynePC to enhance NLP stability was assessed using DOPC-based (18:1 PC) NLPs, due to the relative stability of the DOPC NLPs (FIG. 2A Example 3) as well as their documented low immunogenicity and toxicity [34]. Thus through crosslinking these lipids, covalent bonds were introduced in the internal structure of the NLP, which should create a more stable particle compared to particles that only relied on the non-covalent interactions of the constituent lipid and protein In particular, DOPC-based NLPs were assembled with increasing concentrations of DiynePC, and assessed for NLP formation, size, and stability. For initial assessment, NLPs were assembled with 20 mol % DiynePC and 80 mol % DOPC. Interestingly, the cross-linked and non-cross-linked DiynePC NLPs exhibited a NLP SEC retention profile that was comparable to DOPC NLPs (FIG. 4A). In addition, general size and polydispersity of the DiynePC-bearing NLPs (non-cross-linked and cross-linked) were consistent with 100% DOPC NLPs, as assessed by aSEC (FIG. 4A) and dynamic light scattering (FIG. 4B).

In preliminary experiments to demonstrate that addition of DiynePC has an effect on NLP stability before and after crosslinking, DOPC NLPs, DiynePC (80 mol %) NLPs not exposed to UV and DiynePC (20 mol %) NLPs exposed to UV for ten minutes were incubated in 100% serum for 10 minutes and the fraction of the NLP peak remaining relative to the peak prior to incubation in the serum was measured by aSEC (FIG. 4C). The addition of 20 mol % DiynePC did not lead to a significant increase in NLP stability relative to DOPC NLPs (p=0.16)(FIG. 4C). In contrast, the DiynePC NLPs that had been exposed to UV were more stable than DOPC (p=0.040) at this short time scale (FIG. 4C). Longer time scales will be discussed below.

Figure 5:
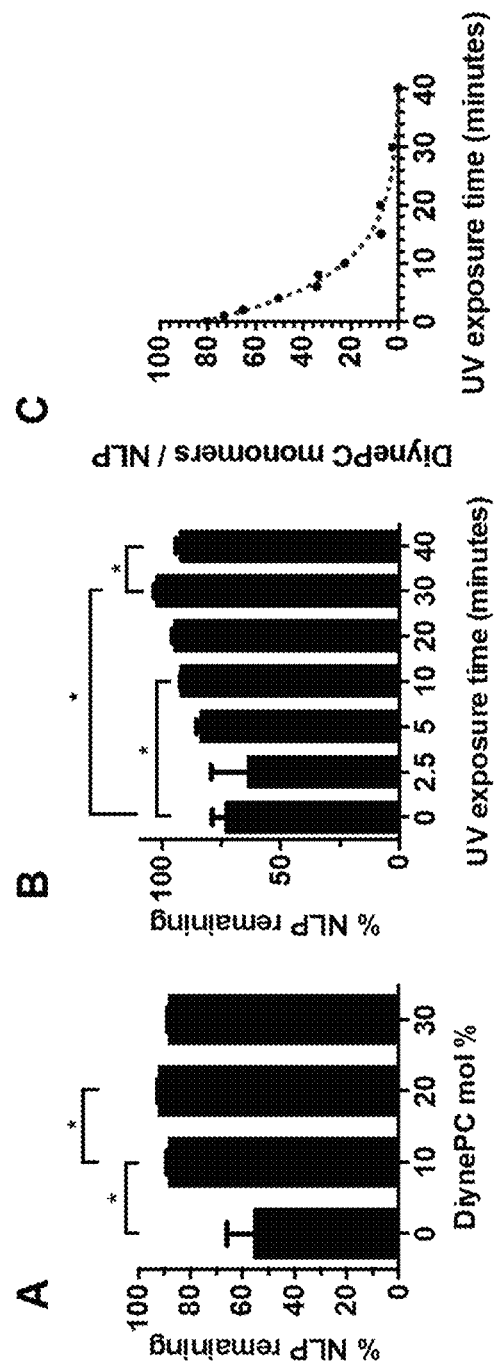
FIG. 5 shows diagrams illustrating results of experiments directed to measure stability of particles formulated with DiynePC.

To better assess the relationship between mol % DiynePC and NLP stability. NLPs were assembled with 10, 20, 30 and 40 mol % DiynePC and incubated in 100% serum at 37° C. for 10 minutes. The fraction of the NLP peak that remained after this 10 minute incubation period is shown in FIG. 5A. Interestingly, a consistent and stable increase in stability (NLPs remaining) was observed with an increase in DiynePC concentration from 10% to 30 mol %, with a significant difference between 0% and 20% (p=0.04). As such, 20 mol % DiynePC was chosen for all subsequent experiments.

To evaluate the effect of UV irradiation time on DiynePC NLP stability, DiynePC NLPs (20 mol %) were assembled and exposed to UV for different lengths of time. The fraction of the NLP area was then measured after a 10 minute incubation in serum (FIG. 5B). In these experiments, the NLP fraction remaining increased gradually up to exposure times of 30 minutes and then decreased when the exposure time was increased further (p=0.0047) (FIG. 5B). These results support the conclusion that shorter irradiation times yield fewer DiynePC-DiynePC crosslinks, whereas longer irradiation times may have compromised the integrity of the NLP. Based on these results, all subsequent experiments were conducted with NLPs consisting of 20% DiynePC, and irradiation times of 10 minutes, as this exposure time yielded the first significant difference over the non-exposed group (p=0.045) (herein referred to as X-NLPs).

To provide a quantitative measure of the degree of DiynePC crosslinking, the decrease in free (uncrosslinked) DiynePC was measured as a function of UV exposure time using reverse phase HPLC and a evaporative light scattering detector. The amount of free DiynePC was measured after each time point by integrating the chromatogram peak area corresponding to DiynePC. Using these data and the known lipid:protein ratio for each NLP formulation, the expected number of DiynePC monomers remaining in a single NLP as a function of UV exposure was calculated. Increased exposure time decreased the amount of free DiynePC, and this trend followed an exponential decay model ($R^2$ of 0.992) (FIG. 5C). By 40 minutes, less than 0.4% of the free DiynePC was detected, suggesting complete intermolecular crosslinking of the DiynePC monomers.

Figure 6:
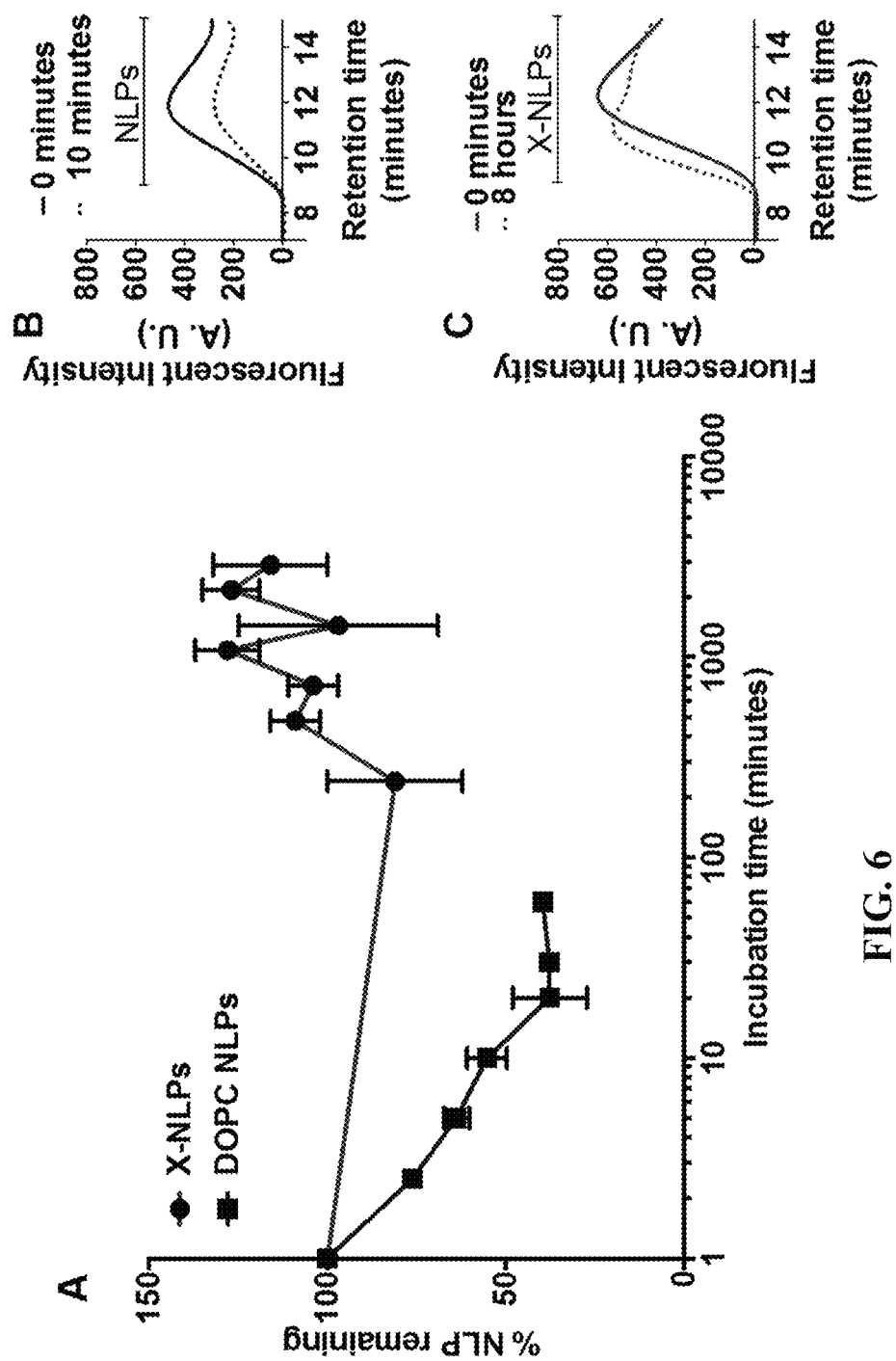
FIG. 6 shows long-term stability in 100% FBS at 37° C. of X-NLPs. (* $p<0.05$).

To assess the long-term stability of the cross-linked 20% DiynePC NLPs in 100% serum, 20% DiynePC NLPs were incubated in 100% serum at 37° C. and analyzed over a 48 hour period. Over the course of 48 hours, no apparent loss in NLP integrity was observed. This was significantly better than the DOPC NLPs, which dissociated within 1 hour (FIG. 6). To better illustrate how the DiynePC and DOPC NLP populations change during exposure to serum, the raw Size Exclusion Chromatography (SEC) traces have also been included here. FIG. 5B shows that after 10 minutes of incubation in serum, the signal due to DOPC NLPs has been reduced compared to zero minutes in serum. Conversely, after eight hours in serum, signal due from the DiynePC NLPs has not been reduced, though the peak center has shifted. These results clearly demonstrate that crosslinking the bilayer core significantly enhanced the overall NLP stability.

Example 6: Uptake of NLPs and Polymerized NLPs by into 5637 Human Bladder Cancer Type II Carcinoma Cells In Vitro As previously discussed, NLPs are an attractive platform for drug delivery, and efficient delivery of therapeutics via the NLP platform requires efficient cellular uptake of the NLP. While the fact that NLPs are rapidly taken up by mouse macrophage has been demonstrate [51], experiments were performed to show that maximizing NLP stability will further increase cellular uptake of intact NLPs by minimizing NLP dissociation in the culture media. Apolipoproteins such as E4 possess a binding site that targets the extracellular LDL receptor, a receptor commonly overexpressed by a variety of cancer cell types. Therefore, experiments wee designed to test inherent cancer cell targeting abilities of NLPs. In particular, to explore the applicability of targeted NLP-based drug delivery in a cancer model, uptake of NLP and X-NLP constructs by human bladder cancer type-II carcinoma cells (5637) was assessed, as these cells represent a viable target for chemotherapeutic delivery.

To monitor cellular uptake, DOPC NLPs and X-NLPs were covalently labeled with Alexa Fluor 488 (see materials and methods) and incubated with cells. 0, 2, 4, 6 and 8 hours after incubation, the cells were trypsinized and NLP and X-NLP uptake was quantified by flow cytometry.

In particular to monitor cellular uptake, DOPC NLPs and cross-linked 20% DiynePC:80% DOPC NLPs were covalently labeled with Alexa Fluor 488 and incubated with cells. 0, 2, 4, 6 and 8 hours after incubation, the cells were trypsinized and NLP and 20% DiynePC:80% DOPC NLPs uptake was quantified by flow cytometry.

Figure 7:
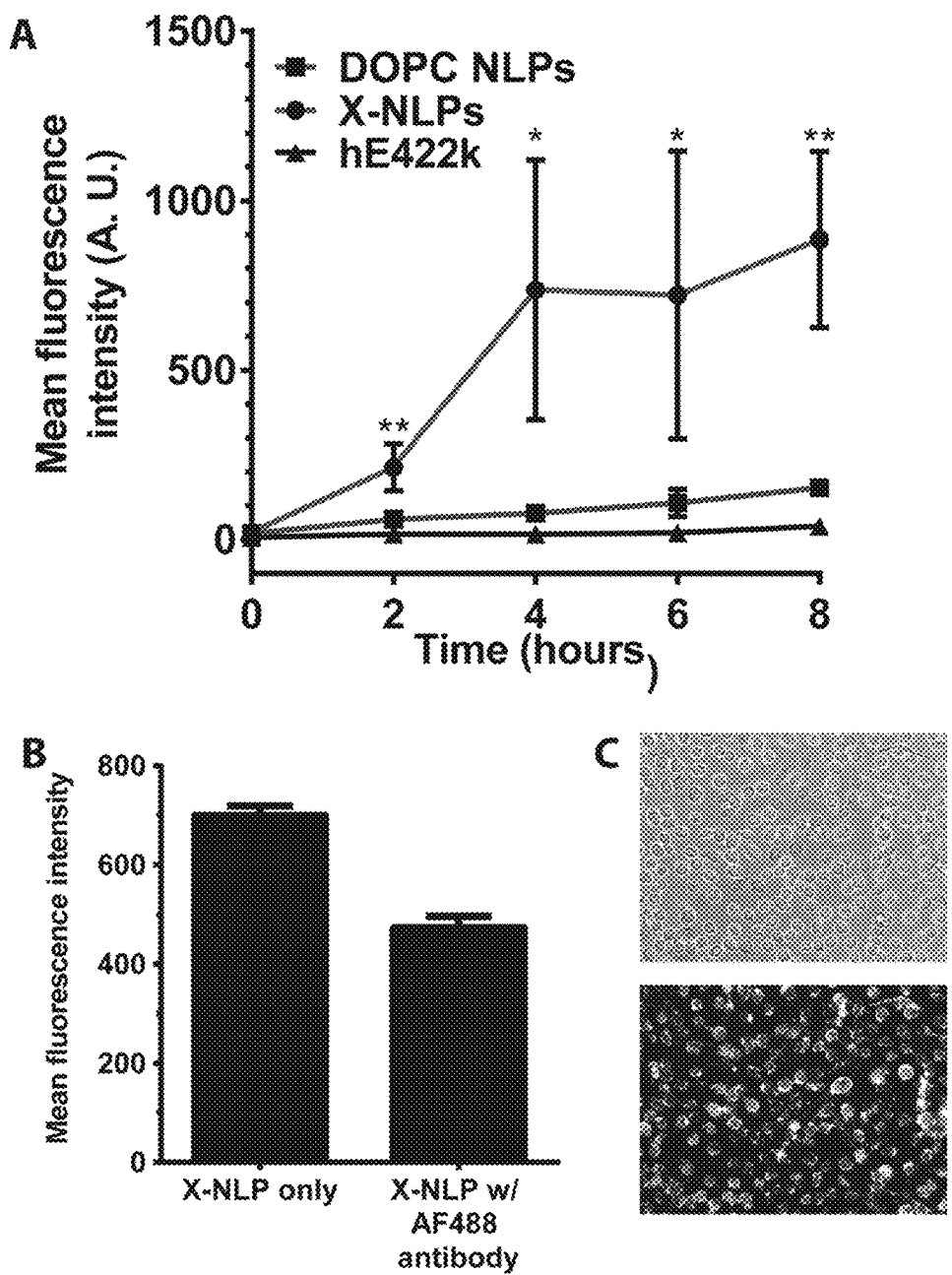
FIG. 7 shows data illustrating the result of experiments directed to measure NLPs uptake from 5637 cells. 5637 cells were incubated with fluorescently labeled DOPC, cross-linked NLPs and scaffold protein alone (ApoE422k). At various time points, the cells were trypsinized and the fluorescence of individual cells was measured by flow cytometry (FIG. 7A). Significantly higher cellular uptake was observed for the cross-linked NLPs (black line) vs DOPC:NLPs (dark gray line), due to increased NLP stability and no uptake of ApoE422k alone (light gray line) was observed (* $p<0.05$, ** $p<0.01$). Cells that were dosed with fluorescently-labeled and crosslinked DiynePC particles were treated with an anti-fluorophore antibody that quenches fluorescence and were subsequently analyzed by flow cytometry (FIG. 7B). Additionally, micrographs of cells dosed with the same particles, obtained with a fluorescence microscope, following treatment with a separate fluorescence quencher are shown in FIG. 7C. In both FIG. 7B and FIG. 7C the persistence of fluorescence following addition of the quenchers indicates that the NLPs have been internalized by the cells.

As shown in FIG. 7A, 20% DiynePC:80% DOPC NLPs uptake was significantly higher than NLP uptake at every time point tested. When apolipoproteins are not bound to an HDL (or NLP), the LDL binding site is not exposed, meaning that free E422k apolipoprotein cannot enter the cells through active transport. Thus, to test if uptake is mediated by the LDL binding domain on the E422k protein, these experiments were repeated with labeled E422k protein that was not associated with lipid or NLPs and, as expected, only a very small increase in MFI of the cells was observed over time (FIG. 7).

These combined results support the conclusion that as the NLPs incubate with the cells in cell culture media at 37° C. over the course of several hours, the DOPC NLPs begin to degrade and the effective E422k concentration that can be taken up by the cells decreases. In contrast, since the 20% DiynePC:80% DOPC NLPs are highly stable, the effective E422k concentration that can be taken up by the cells remains constant; hence greater uptake of 20% DiynePC: 80% DOPC NLPs.

To confirm that the DiynePC NLPs are internalized, two experiments were performed. In the first, cells dosed with the fluorescent particles were treated with an antibody that binds to the fluorophore, effectively quenching it. These cells were analyzed by flow cytometer (FIG. 7B). In the second experiment, cells dosed with the fluorescent particles were treated with a different fluorescence quencher and imaged using a fluorescence microscope (FIG. 7C). In both cases, fluorescence was reduced, but not eliminated. Since both quenchers cannot permeate across the cellular membrane, remaining fluorescence must be within the cell, indicating that the particles are internalized.

These combined results support the conclusion that as the NLPs incubate with the cells in cell culture media at 37° C. over the course of several hours, the DOPC NLPs begin to degrade and the effective E422k concentration that can be taken up by the cells decreases. In contrast, since the X-NLPs are highly stable, the effective E422k concentration that can be taken up by the cells remains constant; hence greater uptake of X-NLPs.

Figure 8:
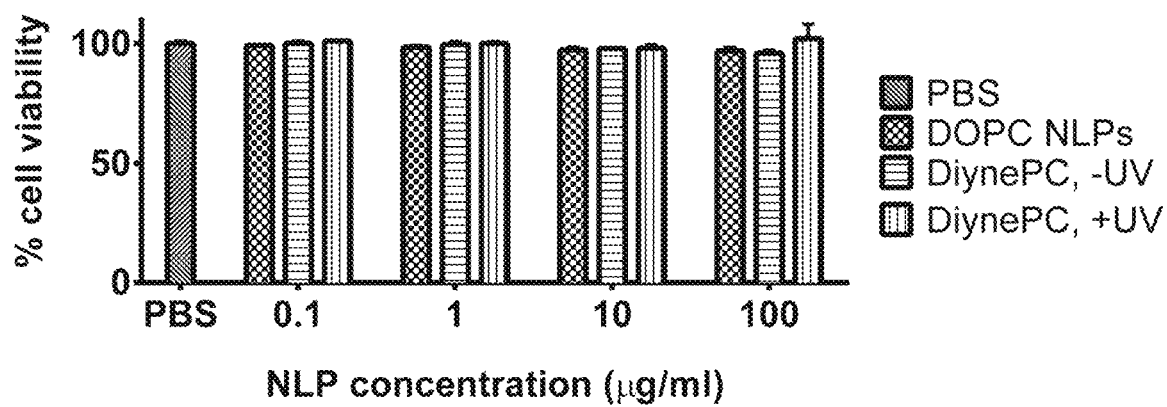
FIG. 8 shows results of experiments directed to assess toxicity of DiynePC NLP formulations compared to DOPC NLPS on human bladder cancer cells in culture (ATCC 5637). The results in FIG. 8 are expressed as the percentage of the cells that remain viable after being dosed with one of three NLP formulations at the specified concentrations. Cells that were dosed with PBS were considered 100% viable, and lysed cells were taken to be 0% viable. No cytotoxicity was observed through this range of NLP concentrations.

To demonstrate that NLPs prepared with DiynePC lipids are well tolerated by cells, cytotoxicity assays were conducted in human bladder cancer cells (ATCC). Cells were dosed with DOPC NLPs, NLPs with DiynePC (no UV exposure), or NLPs with DiynePC (10 minutes of UV exposure) (X-NLPs) at concentrations ranging from 0-100 micrograms per milliliter of complete media. At all concentrations tested, DiynePC formulations (crosslinked or non-crosslinked) had no higher toxicity than the DOPC formulation, and all three formulations were observed to have no substantial effect on cell viability (FIG. 8).

Example 7: Stability of NLPs and Polymerized NLPs In Vivo

To determine if the improved stability in 100% sera described above translates to improved bioavailability of NLPs in vivo, the in vivo stability of only intact NLPs after i.v. administration.

In particular, mice were injected with fluorescently labeled cross-linked 20% DiynePC:80% DOPC NLPs, NLPs or PBS as a vehicle control via the intravenous (i.v.) route. After 10 minutes, blood was collected and spun down to obtain serum, which was subsequently analyzed by aSEC to evaluate NLP integrity and serum concentration. Since a loss of NLP from the blood can result from several processes including degradation of the NLP, removal from the blood stream and uptake by cells in the blood, the 10 min time point was selected because this should be sufficient time for the non-cross-linked NLPs to begin degrading in the serum and yet short enough such that clearance of NLPs from the blood stream and/or uptake by cells in the blood is incomplete.

Figure 9:
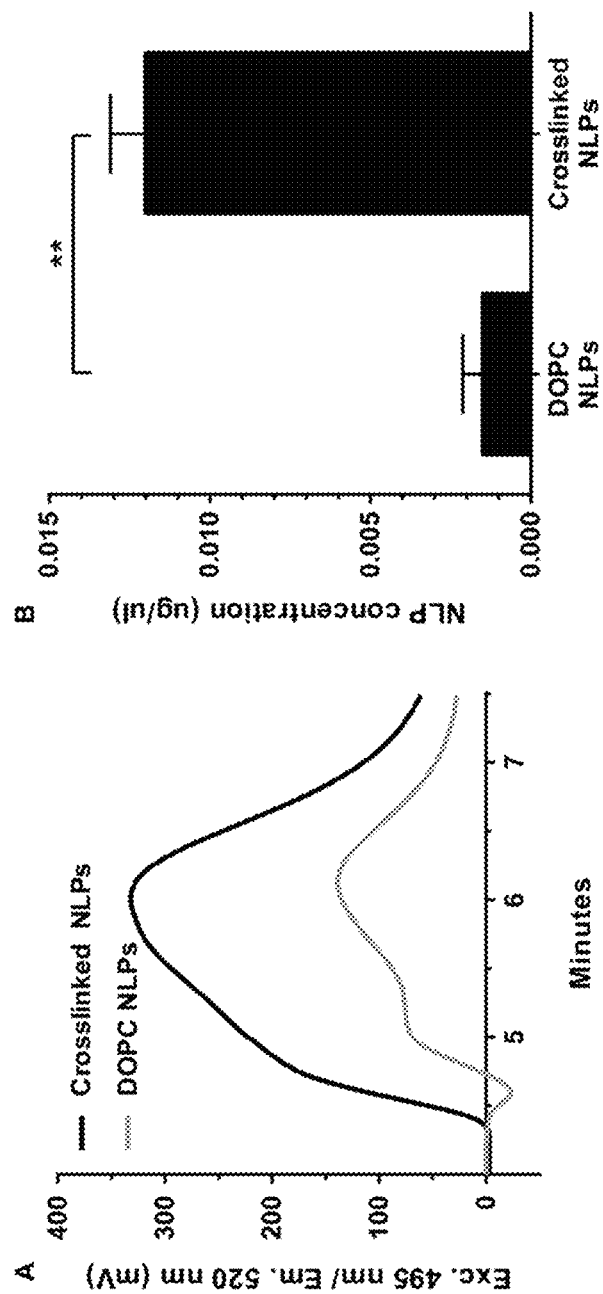
FIG. 9 shows results of experiments directed to measure stability of NLPs in vivo.

Serum from mice injected with DOPC NLPs exhibited a clear fluorescence signal above background (FIG. 9A). However, for mice injected with 20% DiynePC:80% DOPC NLPs, a significantly larger fluorescence signal in the region associated with the 20% DiynePC:80% DOPC NLPs was observed (FIG. 9A).

To determine the actual serum NLP concentration, standards were run and the NLP and 20% DiynePC:80% DOPC NLP peak area were used to measure the amount of NLP and 20% DiynePC:80% DOPC NLP in the injected sample. When this analysis was performed, a significantly higher serum concentration (0.012±0.001 µg/µl versus 0.0015±0.0006 µg/µl, p=0.0013) was observed in the mice receiving the 20% DiynePC:80% DOPC NLPs (FIG. 9B). These results suggest that the increased stability observed in our in vitro model systems translate to increase stability in vivo.

The above results show that the blood concentration of intact particle was 8 times higher for X-NLPs vs NLPs 10 minutes after i.v. administration.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure. Those skilled in the art will recognize how to adapt the features of the exemplified NLPs and related uses to additional NLPs formed by other membrane forming lipids, polymerizable lipids scaffold proteins and possibly functionalized amphipathic compounds and membrane proteins according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

REFERENCES

1. Georger, J. H., et al., *Helical and Tubular Microstructures Formed by Polymerizable Phosphatidylcholines*. J Am Chem Soc, 1987. 109(20): p. 6169-6175.
2. Morigaki, K., et al., *Surface Functionalization of a Polymeric Lipid Bilayer for Coupling a Model Biological Membrane with Molecules, Cells, and Microstructures*. Langmuir, 2013. 29(8): p. 2722-2730.
3. Regen, S. L., et al., *Polymerized Phosphatidyl Choline Vesicles-Stabilized and Controllable Time-Release Carriers*. Biochemical and Biophysical Research Communications, 1981. 101(1): p. 131-136.
4. Bolikal, D. and S. L. Regen, *Degree of Polymerization of a Vesicle Membrane*. Macromolecules, 1984. 17(6): p. 1287-1289.
5. Lei, J. T. and D. F. Obrien, *2-Dimensional Polymerization of Lipid Bilayers—Rate of Polymerization of Acryloyl and Methacryloyl Lipids*. Macromolecules, 1994. 27(6): p. 1381-1388.
6. Sells, T. D. and D. F. Obrien, *2-Dimensional Polymerization of Lipid Bilayers—Degree of Polymerization of Acryloyl Lipids*. Macromolecules, 1994. 27(1): p. 226-233.
7. Lamparski, H. and D. F. Obrien, *2-Dimensional Polymerization of Lipid Bilayers—Degree of Polymerization of Sorbyl Lipids*. Macromolecules, 1995. 28(6): p. 1786-1794.
8. Tsuchida, E., et al., *Polymerization of Unsaturated Phospholipids as Large Unilamellar Liposomes at Low-Temperature*. Macromolecules, 1992. 25(1): p. 207-212.
9. Ohno, H., Y. Ogata, and E. Tsuchida, *Polymerization of Liposomes Composed of Diene-Containing Lipids by Uv and Radical Initiators—Evidence for the Different Chemical Environment of Diene Groups on 1-Acyl and 2-Acyl Chains*. Macromolecules, 1987. 20(5): p. 929-933.
10. Serrano, J., et al., *Polymerized Surfactant Vesicles—Determinations of Rates and Degrees of Polymerization in Vesicles Prepared from Styrene-Containing Surfactants*. Macromolecules, 1985. 18(10): p. 1999-2005.
11. Lieser, G., B. Tieke, and G. Wegner, *Structure, Phase-Transitions and Polymerizability of Multilayers of Some Diacetylene Monocarboxylic Acids*. Thin Solid Films, 1980. 68(1): p. 77-90.
12. Johnston, D. S., et al., *Phospholipid polymers—synthesis and spectral characteristics*. Biochim Biophys Acta, 1980. 602(1): p. 57-69.
13. Kim, J. M., et al., *Immobilized polydiacetylene vesicles on solid substrates for use as chemosensors*. Advanced Materials, 2003. 15(13): p. 1118-1121.

14. Hayward, J. A. and D. Chapman, *Biomembrane surfaces as models for polymer design: the potential for haemocompatibility*. Biomaterials, 1984. 5(3): p. 135-42.
15. Regen, S. L., et al., *Polymerized phosphatidyl choline vesicles. Stabilized and controllable time-release carriers*. Biochem Biophys Res Commun, 1981. 101(1): p. 131-6.
16. Yavlovich, A., et al., *A novel class of photo-triggerable liposomes containing DPPC:DC8,9PC as vehicles for delivery of doxorubcin to cells*. Biochimica Et Biophysica Acta-Biomembranes, 2011. 1808(1): p. 117-126.
17. Tieke, B., G. Lieser, and G. Wegner, *Polymerization of diacetylenes in multilayers*. Journal of Polymer Science: Polymer Chemistry Edition, 1979. 17(6): p. 1631-1644.
18. Baughman, R. H., *Solid-state polymerization of diacetylenes*. Journal of Applied Physics, 1972. 43(11): p. 4362-4370.
19. Blanchette, C. D., et al., *Kinetic Analysis of His-Tagged Protein Binding to Nickel-Chelating Nanolipoprotein Particles*. Bioconjugate Chemistry, 2010. 21(7): p. 1321-1330.
20. Fischer, N. O., et al., *Colocalized Delivery of Adjuvant and Antigen Using Nanolipoprotein Particles Enhances the Immune Response to Recombinant Antigens*. Journal of the American Chemical Society, 2013. 135(6): p. 2044-2047.
21. Shih, A. Y., et al., *Disassembly of nanodiscs with cholate*. Nano Letters, 2007. 7(6): p. 1692-1696.
22. Chromy, B. A., et al., *Different apolipoproteins impact nanolipoprotein particle formation*. Journal of the American Chemical Society, 2007. 129(46): p. 14348-14354.
23. Blanchette, C. D., et al., *Characterization and Purification of Polydisperse Reconstituted Lipoproteins and Nanolipoprotein Particles*. International Journal of Molecular Sciences, 2009. 10(7): p. 2958-2971.
24. CHROMY, B. A., *NANOLIPOPROTEIN PARTICLES AND RELATED METHODS AND SYSTEMS FOR PROTEIN CAPTURE, SOLUBILIZATION, AND/OR PURIFICATION* in US 2009-0192299 A1 2009: US.
25. Cappuccio, J. A., et al., *Cell-free Co-expression of Functional Membrane Proteins and Apolipoprotein, Forming Soluble Nanolipoprotein Particles*. Molecular & Cellular Proteomics, 2008. 7(11): p. 2246-2253.
26. Gao, T. J., et al., *Characterizing diffusion dynamics of a membrane protein associated with nanolipoproteins using fluorescence correlation spectroscopy*. Protein Science, 2011. 20(2): p. 437-447.
27. Katzen, F., et al., *Insertion of membrane proteins into discoidal membranes using a cell-free protein expression approach*. Journal of Proteome Research, 2008. 7(8): p. 3535-3542.
28. Coleman, M. A., *METHODS AND SYSTEMS FOR PRODUCING NANOLIPOPROTEIN PARTICLES*, in US 2011-0059549 A1 2008: US.
29. Okazaki, T., et al., *Polymerized lipid bilayers on a solid substrate: Morphologies and obstruction of lateral diffusion*. Langmuir, 2008. 25(1): p. 345-351.
30. Okazaki, T., Y. Tatsu, and K. Morigaki, *Phase separation of lipid microdomains controlled by polymerized lipid bilayer matrices*. Langmuir, 2009. 26(6): p. 4126-4129.
31. Tufteland, M., G. Ren, and R. Ryan, *Nanodisks derived from amphotericin B lipid complex*. Journal of Pharmaceutical Sciences, 2008. 97(10): p. 4425-4432.
32. Yuan, Y., et al., *Delivery of hydrophilic drug doxorubicin hydrochloride-targeted liver using apoAI as carrier*. J Drug Target, 2013. 21(4): p. 367-374.
33. Ding, Y., et al., *A biomimetic nanovector-mediated targeted cholesterol-conjugated siRNA delivery for tumor gene therapy*. Biomaterials, 2012. 33(34): p. 8893-8905.
34. Fischer, N. O., et al., *Evaluation of Nanolipoprotein Particles (NLPs) as an In Vivo Delivery Platform*. PLoS ONE, 2014. 9(3): p. e93342.
35. Allen, T. M. and P. R. Cullis, *Drug delivery systems: entering the mainstream*. Science, 2004. 303(5665): p. 1818-22.
36. Sparreboom, A., et al., *Comparative preclinical and clinical pharmacokinetics of a cremophor-free, nanoparticle albumin-bound paclitaxel (ABI-007) and paclitaxel formulated in Cremophor (Taxol)*. Clin Cancer Res, 2005. 11(11): p. 4136-43.
37. Frias, J. C., et al., *Properties of a versatile nanoparticle platform contrast agent to image and characterize atherosclerotic plaques by magnetic resonance imaging*. Nano Lett, 2006. 6(10): p. 2220-2224.
38. Fischer, N. O., et al., *Conjugation to nickel-chelating nanolipoprotein particles increases the potency and efficacy of subunit vaccines to prevent West Nile encephalitis*. Bioconjug Chem, 2010. 21(6): p. 1018-22.
39. Fischer, N. O., et al., *Colocalized delivery of adjuvant and antigen using nanolipoprotein particles enhances the immune response to recombinant antigens*. J Am Chem Soc, 2013. 135(6): p. 2044-7.
40. Weilhammer, D. R., et al., *The use of nanolipoprotein particles to enhance the immunostimulatory properties of innate immune agonists against lethal influenza challenge*. Biomaterials, 2013. 34(38): p. 10305-18.
41. Bhattacharya, P., et al., *Nanodisc-Incorporated Hemagglutinin Provides Protective Immunity against Influenza Virus Infection*. Journal of Virology, 2010. 84(1): p. 361-371.
42. Cho, K., et al., *Therapeutic nanoparticles for drug delivery in cancer*. Clinical cancer research, 2008. 14(5): p. 1310-1316.
43. Tark, S. H., et al., *Nanomechanical detection of cholera toxin using microcantilevers functionalized with ganglioside nanodiscs*. Nanotechnology, 2010. 21(43).
44. Das, A., et al., *Screening of Type I and II Drug Binding to Human Cytochrome P450-3A4 in Nanodiscs by Localized Surface Plasmon Resonance Spectroscopy*. Analytical Chemistry, 2009. 81(10): p. 3754-3759.
45. Pavlidou, M., et al., *Nanodiscs Allow Phage Display Selection for Ligands to Non-Linear Epitopes on Membrane Proteins*. PLoS One, 2013. 8(9).
46. Yang, T. and J. Y. Chen, *Identification and cellular localization of human PFTAIRE1* Gene, 2001. 267(2): p. 165-172.
47. Yang, T. L., et al., *Investigations of bivalent antibody binding on fluid-supported phospholipid membranes: The effect of hapten density*. Journal of the American Chemical Society, 2003. 125(16): p. 4779-4784.
48. Mao, H. B., T. L. Yang, and P. S. Cremer, *Design and characterization of immobilized enzymes in microfluidic systems*. Analytical Chemistry, 2002. 74(2): p. 379-385.
49. Jonsson, M. P., et al., *Supported lipid bilayer formation and lipid-membrane-mediated biorecognition reactions studied with a new nanoplasmonic sensor template*. Nano Letters, 2007. 7(11): p. 3462-3468.
50. Miyazaki, M., et al., *Effect of phospholipid composition on discoidal HDL formation*. Biochimica et Biophysica Acta (BBA)-Biomembranes, 2013. 1828(5): p. 1340-1346.
51. Weilhammer, D. R., et al., *The use of nanolipoprotein particles to enhance the immunostimulatory properties of*

*innate immune agonists against lethal influenza challenge.* Biomaterials, 2013. 34(38): p. 10305-10318.
52. Cappuccio, J. A., et al., *Cell-free co-expression of functional membrane proteins and apolipoprotein, forming soluble nanolipoprotein particles.* Molecular & Cellular Proteomics, 2008. 7(11): p. 2246-2253.
53. Cappuccio, J. A., et al., *Cell-free expression for nanolipoprotein particles: building a high-throughput membrane protein solubility platform,* in *High throughput protein expression and purification.* 2009, Springer. p. 273-295.
54. Blanchette, C. D., et al., *Atomic force microscopy differentiates discrete size distributions between membrane protein containing and empty nanolipoprotein particles.* Biochimica et Biophysica Acta (BBA)-Biomembranes, 2009. 1788(3): p. 724-731.
55. Wadsäter, M., et al., *Monitoring shifts in the conformation equilibrium of the membrane protein cytochrome P450 reductase (POR) in nanodiscs.* Journal of Biological Chemistry, 2012. 287(41): p. 34596-34603.
56. Justesen, B. H., et al., *Isolation of monodisperse nanodisc-reconstituted membrane proteins using free flow electrophoresis.* Analytical chemistry, 2013. 85(7): p. 3497-3500.
57. Baylon, J. L., et al., *Characterizing the membrane-bound state of cytochrome P450 3A4: structure, depth of insertion, and orientation.* Journal of the American Chemical Society, 2013. 135(23): p. 8542-8551.
58. Gao, T., et al., *Characterization of De Novo Synthesized GPCRs Supported in Nanolipoprotein Discs.* PLoS ONE, 2012. 7(9): p. e44911.
59. Akkaladevi, N., et al., *Assembly of anthrax toxin pore: Lethal-factor complexes into lipid nanodiscs.* Protein Science, 2013. 22(4): p. 492-501.
60. Tufteland, M., et al., *Peptide stabilized amphotericin B nanodisks.* Peptides, 2007. 28(4): p. 741-746.
61. Jia, J., et al., *Preparation, characterizations, and in vitro metabolic processes of paclitaxel-loaded discoidal recombinant high-density lipoproteins.* Journal of Pharmaceutical Sciences, 2012. 101(8): p. 2900-2908.
62. Wang, J., et al., *Tumor targeting effects of a novel modified paclitaxel-loaded discoidal mimic high density lipoproteins.* Drug delivery, 2013. 20(8): p. 356-363.
63. Fischer, N. O., et al., *Conjugation to Nickel-Chelating Nanolipoprotein Particles Increases the Potency and Efficacy of Subunit Vaccines to Prevent West Nile Encephalitis.* Bioconjugate Chemistry, 2010. 21(6): p. 1018-1022.
64. Rensen, P. C. N., et al., *Recombinant lipoproteins: lipoprotein-like lipid particles for drug targeting.* Advanced Drug Delivery Reviews, 2001. 47(2-3): p. 251-276.
65. Blanchette, C. D., et al., *Quantifying size distributions of nanolipoprotein particles with single-particle analysis and molecular dynamic simulations.* Journal of Lipid Research, 2008. 49(7): p. 1420-1430.
66. Fischer, N. O., et al., *Evaluation of Nanolipoprotein Particles (NLPs) as an In Vivo Delivery Platform.* Plos One, 2014. 9(3).
67. Rawicz, W., et al., *Effect of Chain Length and Unsaturation on Elasticity of Lipid Bilayers.* Biophysical Journal, 79(1): p. 328-339.
68. Rabinovich, A. L. and P. O. Ripatti, *On the conformational, physical properties and functions of polyunsaturated acyl chains.* Biochim Biophys Acta, 1991. 1085(1): p. 53-62.
69. Portet, T. and R. Dimova, *A new method for measuring edge tensions and stability of lipid bilayers: effect of membrane composition.* Biophysical journal, 2010. 99(10): p. 3264-3273.
70. Sparks, D. L., et al., *Effect of cholesterol on the charge and structure of apolipoprotein A-I in recombinant high density lipoprotein particles.* Journal of Biological Chemistry, 1993. 268(31): p. 23250-7.
71. Sadownik, A., J. Stefely, and S. L. Regen, *Polymerized liposomes formed under extremely mild conditions.* Journal of the American Chemical Society, 1986. 108(24): p. 7789-7791.

The invention claimed is:
1. A nanolipoprotein particle comprising:
a membrane forming lipid, a polymerized lipid and a scaffold protein,
the membrane forming lipid and the polymerized lipid arranged in a membrane forming lipid discoidal bilayer stabilized by the scaffold protein and by the polymerized lipid,
wherein the polymerized lipid is formed by crosslinking polymerizable lipids within the membrane forming lipid discoidal bilayer in a molar concentration of about 5 to about 40 mol %.
2. The nanolipoprotein particle of claim 1, wherein the polymerized lipid is in a molar concentration of about 10 to about 40 mol %.
3. The nanolipoprotein particle of claim 1, wherein a total lipid to scaffold protein molar percent ratio ranges from 20:1 to 240:1.
4. The nanolipoprotein particle of claim 1, wherein the membrane forming lipid is in amount from 95 to 60% and the polymerized lipid is in an amount from 5 to 40% with respect to a total lipid concentration.
5. The nanolipoprotein particle of claim 1, wherein the membrane forming lipid and polymerized lipid are in a molar percent ratio membrane forming lipid: polymerized lipids ranging from 95:5 to 60:40.
6. The nanolipoprotein particle of claim 1, wherein the polymerizable lipids comprise lipids of Formula (I)

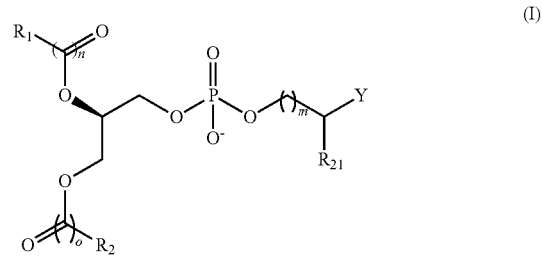

wherein
R1 and R2 are independently selected from C7-C29 branched or straight, substituted or unsubstituted aliphatic carbon chain, at least one of R1 and R2 present at least one polymerizable functional group;

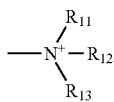

(V)

in which $R_{11}$, $R_{12}$ and $R_{13}$ are independently H or a C1-C4 branched or straight aliphatic carbon chain;

$R_{21}$ is H, OH, or a carboxy group m=0-3; and n and o are independently 0 and 1.

7. The nanolipoprotein particle of claim 6, wherein R1, and R2 present at least two polymerizable functional groups for polymerization with corresponding functional groups within the membrane lipid bilayer.

8. The nanolipoprotein particle of claim 1, wherein the polymerizable lipids comprise lipids of Formula (VI)

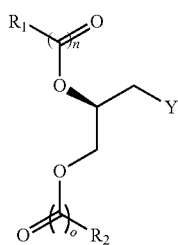

(VI)

wherein $R_1$, $R_2$ are independently a C7-C29 branched or straight, substituted or unsubstituted aliphatic carbon chain;

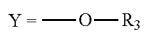 (VII)

 (VIII)

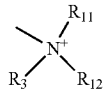 (IX)

in which $R_{11}$, $R_{12}$ are independently H or a C1-C4 branched or straight aliphatic carbon chain and R3 is a C7-C29 branched or straight, substituted or unsubstituted aliphatic carbon chain, n and o are independently 0 and 1;

and wherein at least one of $R_1$, $R_2$ and $R_3$ comprise at least one polymerizable functional group.

9. The nanolipoprotein particle of claim 8, wherein at $R_1$, $R_2$ and $R_3$ present at least two polymerizable functional groups for polymerization with corresponding functional groups within the membrane lipid bilayer.

10. The nanolipoprotein particle of claim 1, wherein the polymerizable lipids comprise lipids of Formula (X)

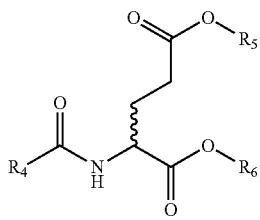

(X)

wherein $R_4$, $R_5$ and $R_6$ are independently C7-C29 branched or straight, substituted or unsubstituted aliphatic carbon chain, at least one of $R_4$, $R_5$ and $R_6$ contains at least one polymerizable functional group, and at least one of $R_4$, $R_5$ and $R_6$ contains at least one amino nitrogen.

11. The nanolipoprotein particle of claim 10, wherein at least one of $R_2$, $R_3$ and $R_4$ contains 1-6 units of an ethyleneoxy group —$(CH_2CH_2O)$—.

12. The nanolipoprotein particle of claim 6, wherein the at least one polymerizable functional group in the polymerizable lipids of Formula (I) is selected from diacetylene groups, methacrylate groups, acryloyl groups, sorbyl ester groups, diene groups, styrene groups, vinyl groups and isocyano groups.

13. The nanolipoprotein particle of claim 1, wherein the nanolipoprotein particle further comprises one or more functionalized amphipathic compound.

14. The nanolipoprotein particle of claim 13, wherein the one or more functionalized amphipathic compounds comprise one or more functionalized membrane forming lipids.

15. The nanolipoprotein particle of claim 14, wherein the one or more functionalized membrane forming lipids is present in 0.1 mol % to 95 mol % relative to polymerized lipid in the membrane lipid bilayer.

16. The nanolipoprotein particle of claim 1, further comprising one or more membrane proteins attached to the membrane lipid bilayer through interaction of the target protein hydrophobic region with the membrane lipid bilayer.

17. The nanolipoprotein particle of claim 1, further comprising one or more functional molecules selected from a functional molecule embedded in the membrane lipid bilayer, a functional molecule conjugated to a lipophilic anchor compound inserted into the membrane lipid bilayer and a functional molecule conjugated through binding of a functional group with a corresponding functional group presented on functionalized membrane forming lipid of the membrane lipid bilayer.

18. The nanolipoprotein particle of claim 17, wherein the one or more functional molecule comprises drug or cellular targeting compound.

19. The nanolipoprotein particle of claim 18, wherein the drug or cellular targeting compound are in an amount ranging from 0.1-10 mol %.

20. A nanolipoprotein particle comprising a cross-linked membrane lipid bilayer confined in a discoidal configuration by a scaffold protein, the cross-linked membrane lipid bilayer comprising one or more polymerized lipids and one or more membrane forming lipids.

21. The nanolipoprotein particle of claim 20, wherein the one or more polymerized lipids comprise lipids of Formula (I)

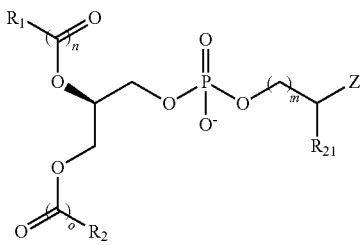
(I)

wherein
R₁ and R₂ are independently selected from C7-C29 branched or straight, substituted or unsubstituted aliphatic carbon chain, at least one of R₁ and R₂ present at least one polymerizable functional group;

$Z = $ —S—R₁₁, (II)

—O—R₁₁ or (IV)

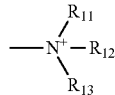 (V)

in which R₁₁, R₁₂ and R₁₃ are independently H or a C1-C4 branched or straight aliphatic carbon chain;
R₂₁ is H, OH, or a carboxy group
m=0-3; and
n and o are independently 0 and;
and wherein the at least one polymerizable functional group binds a corresponding polymerizable functional group in the membrane lipid bilayer providing a polymerized lipid within the membrane lipid bilayer.

22. The nanolipoprotein particle of claim 21, wherein at least two polymerizable functional group binds a corresponding polymerizable functional group in the membrane lipid bilayer thus providing a polymerized lipid within the membrane lipid bilayer.

23. The nanolipoprotein particle of claim 20, wherein the one or more polymerized lipids comprise a lipid of Formula (VI)

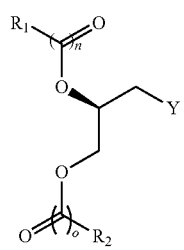 (VI)

wherein
R₁, R₂ are independently a C7-C29 branched or straight, substituted or unsubstituted aliphatic carbon chain;

Y = —O—R₃ (VII)

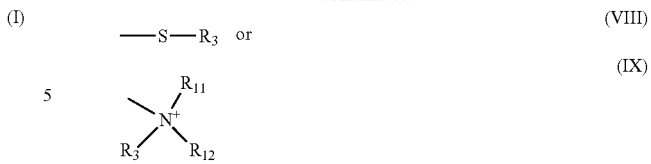

in which R₁₁, R₁₂ are independently H or a C1-C4 branched or straight aliphatic carbon chain and R₃ is a C7-C29 branched or straight, substituted or unsubstituted aliphatic carbon chain,
n and o are independently 0 and 1;
and wherein at least one of R₁, R₂ and R₃ comprise at least one polymerizable functional group binding a corresponding polymerizable functional group in the membrane lipid bilayer thus providing a polymerized lipid within the membrane lipid bilayer.

24. The nanolipoprotein particle of claim 23, wherein at least two polymerizable functional group binds a corresponding polymerizable functional group in the membrane lipid bilayer thus providing a polymerized lipid within the membrane lipid bilayer.

25. The nanolipoprotein particle of claim 20, wherein the one or more polymerizable lipids comprise a lipid of Formula (X)

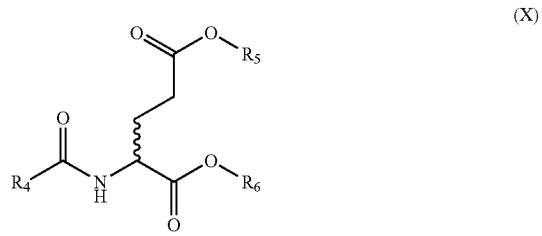 (X)

wherein
R₄, R₅ and R₆ are independently C7-C29 branched or straight, substituted or unsubstituted aliphatic carbon chain, at least one of R₄, R₅ and R₆ contains at least one amino nitrogen and at least one of R₄, R₅ and R₆ contains at least one polymerizable functional group binding a corresponding polymerizable functional group in the membrane lipid bilayer thus providing a polymerized lipid within the membrane lipid bilayer.

26. The nanolipoprotein particle of claim 25, wherein at least two polymerizable functional group binds a corresponding polymerizable functional group in the membrane lipid bilayer thus providing a polymerized lipid within the membrane lipid bilayer.

27. The nanolipoprotein particle of claim 25, wherein at least one of R₄, R₅ and R₆ contains 1-6 units of an ethyleneoxy group —(CH₂CH₂O)—.

28. The nanolipoprotein particle of claim 20, wherein the polymerizable functional group is selected from diacetylene groups, methacrylate groups, acryloyl groups, sorbyl ester groups, diene groups, styrene groups, vinyl groups and isocyano groups.

29. The nanolipoprotein particle of claim 20, wherein the nanolipoprotein particle further comprises one or more functionalized amphipathic compound.

30. The nanolipoprotein particle of claim 29, wherein the one or more functionalized amphipathic compound comprise one or more functionalized membrane forming lipids.

31. The nanolipoprotein particle of claim 30, wherein the one or more functionalized membrane forming lipids is present in 0.1 mol % to 95 mol % relative to polymerized lipid in the membrane lipid bilayer.

32. The nanolipoprotein particle of claim 20, further comprising one or more membrane proteins attached to the membrane lipid bilayer through interaction of the target protein hydrophobic region with the membrane lipid bilayer.

33. The nanolipoprotein particle of claim 20, further comprising one or more functional molecules selected from a functional molecule embedded in the membrane lipid bilayer, a functional molecule conjugated to a lipophilic anchor compound inserted into the membrane lipid bilayer and a functional molecule conjugated through binding of a functional group with a corresponding functional group presented on functionalized membrane forming lipid of the membrane lipid bilayer.

34. The nanolipoprotein particle of claim 33, wherein the one or more functional molecule comprises drug or cellular targeting compound.

35. The nanolipoprotein particle of claim 34, wherein the drug or cellular targeting compound are in an amount ranging from 0.1-10 mol %.

36. A nanolipoprotein particle comprising:

a membrane forming lipid, a polymerized lipid and a scaffold protein, the membrane forming lipid and the polymerized lipid arranged in a membrane forming lipid discoidal bilayer stabilized by the scaffold protein and by the polymerized lipid, wherein the polymerized lipid is formed by crosslinking polymerizable lipids, and wherein the polymerized lipid is in a molar concentration of about 10 to about 30 mol % and a total lipid to scaffold protein molar percent ratio ranges from 20:1 to 240:1.

* * * * *